United States Patent
Meyerson et al.

(10) Patent No.: US 10,590,473 B2
(45) Date of Patent: Mar. 17, 2020

(54) RAPID QUANTITATIVE DETECTION OF SINGLE NUCLEOTIDE POLYMORPHISMS OR SOMATIC VARIANTS AND METHODS TO IDENTIFY MALIGNANT NEOPLASMS

(71) Applicants: THE BROAD INSTITUTE, INC., Cambridge, MA (US); DANA-FARBER CANCER INSTITUTE, INC., Boston, MA (US); THE GENERAL HOSPITAL CORPORATION, Boston, MA (US)

(72) Inventors: Matthew Meyerson, Boston, MA (US); Ganesh M. Shankar, Boston, MA (US); Joshua M. Francis, Cambridge, MA (US); Daniel P. Cahill, Boston, MA (US); Mikael L. Rinne, Boston, MA (US)

(73) Assignees: THE BROAD INSTITUTE, INC., Cambridge, MA (US); DANA-FARBER CANCER INSTITUTE, INC., Boston, MA (US); THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 15/538,382

(22) PCT Filed: Dec. 22, 2015

(86) PCT No.: PCT/US2015/067524
§ 371 (c)(1),
(2) Date: Jun. 21, 2017

(87) PCT Pub. No.: WO2016/106391
PCT Pub. Date: Jun. 30, 2016

(65) Prior Publication Data
US 2017/0369939 A1    Dec. 28, 2017

Related U.S. Application Data

(60) Provisional application No. 62/095,386, filed on Dec. 22, 2014.

(51) Int. Cl.
*C12Q 1/68*    (2018.01)
*C12Q 1/6853*    (2018.01)
*C12Q 1/6827*    (2018.01)

(52) U.S. Cl.
CPC ........ *C12Q 1/6853* (2013.01); *C12Q 1/6827* (2013.01); *C12Q 2525/107* (2013.01); *C12Q 2531/113* (2013.01); *C12Q 2545/114* (2013.01)

(58) Field of Classification Search
None
See application file for complete search history.

(56) References Cited

U.S. PATENT DOCUMENTS

| | | |
|---|---|---|
| 2007/0178445 A1 | 8/2007 | Eshleman et al. |
| 2012/0202207 A1 | 8/2012 | Vogelstein et al. |
| 2013/0102653 A1 | 4/2013 | Griewank et al. |

FOREIGN PATENT DOCUMENTS

WO    2014029669 A1    2/2014

OTHER PUBLICATIONS

Rachakonda, et al., "TERT promoter mutations in bladder cancer affect patient survival and disease recurrence through modification by a common polymorphism," Proc. Natl. Acad. Sci. USA, Oct. 22, 2013, vol. 110, No. 43, pp. 17426-17431, Especially abstract.
Yuen et al., "Histone H3.3 mutations: a variant path to cancer," Cancer Cell, Nov. 11, 2013, vol. 24, No. 5, pp. 567-574, Especially abstract.
International Search Report and Written Opinion from corresponding PCT/US2015/067524, dated Mar. 4, 2016 (11 pages).

*Primary Examiner* — James Martinell
(74) *Attorney, Agent, or Firm* — Melissa Hunter-Ensor; Leslie Serunian; Greenberg Traurig, LLP

(57) ABSTRACT

Provided are systems, kits, and methods for the quantitative detection of single nucleotide polymorphisms or variants to identify malignant neoplasms. The methods include use of modified oligonucleotide blockers with peptide nucleic acid backbones that hybridize to and block logarithmic amplification of the wild-type alleles of a target, and incorporation of locked nucleic acids into probes that are complementary to a mutant allele of the target sequence to increase specificity. The methods include detection of variants in sequences with high GC content and/or low complexity, such as the TERT promoter, IDH1, BRAF, NRAS, GNAQ, GNA11 and H3F3 A gene variants. The methods include sensitive detection and staging of cancers with low cellularity, and can be used intraoperatively such as for glioma, or to detect cell-free circulating tumor DNA, such as for melanoma.

23 Claims, 28 Drawing Sheets
Specification includes a Sequence Listing.

Fig. 3A-B

IDH1 sequencing

TERT promoter sequencing

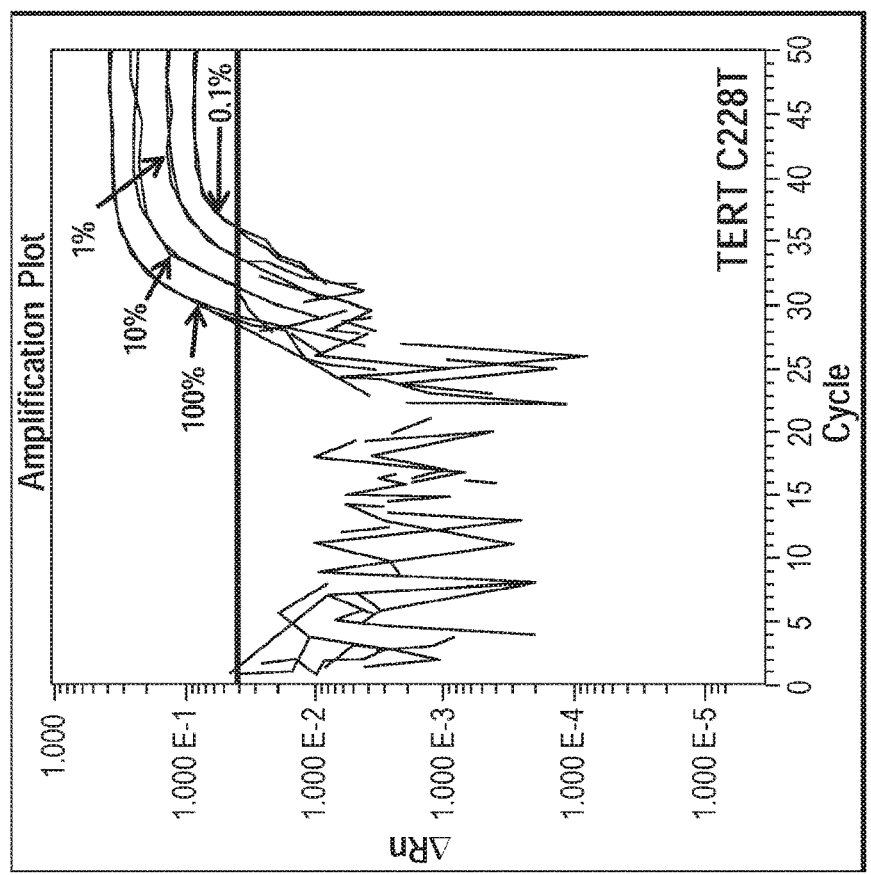
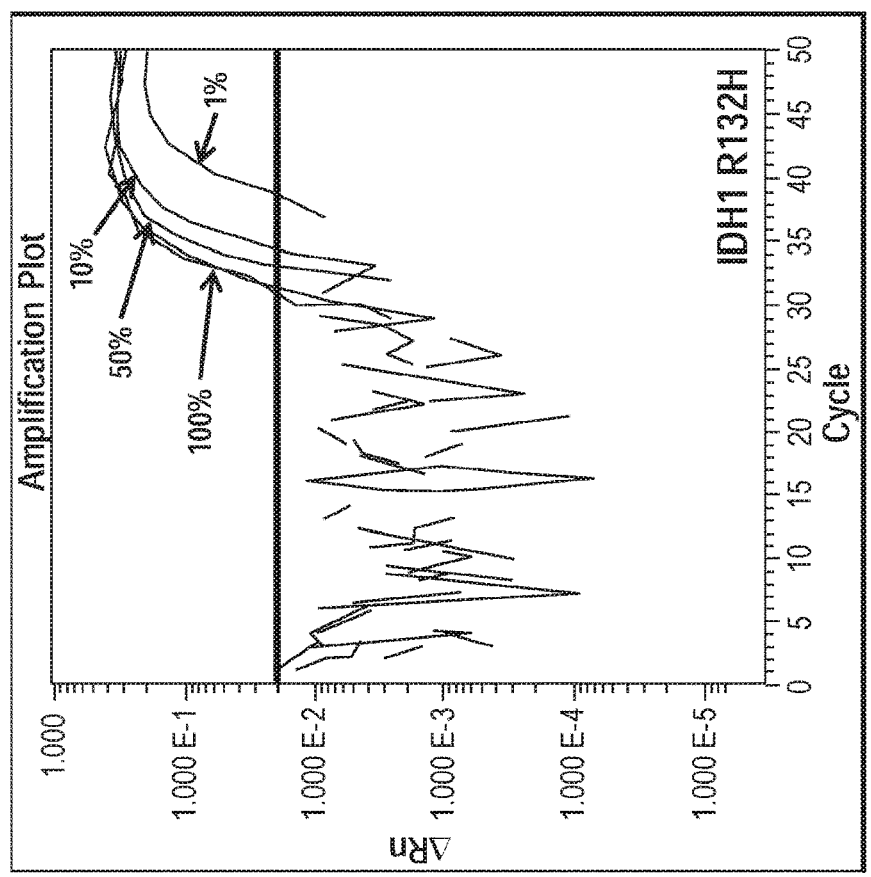
Fig. 7A
Fig. 7B

| Gene | sSNV | Forward Primer | | Reverse Primer | |
|---|---|---|---|---|---|
| | | Sequence | Vendor | Sequence | Vendor |
| IDH1 | R132H | 5'-CGGGCTTGTGAGTGGATGGGTAAAACCT-3' | IDT | 5'-CATTATTGCCAACATGACTTACTTGATCCCC-3' | IDT |
| TERT | C228T | 5'-CACGTGCGCAGCAGGACGCAG-3' | IDT | 5'-CTTCACCTTCCAGCTCCGCCTC-3' | IDT |
| TERT | C250T | 5'-CACGTGCGCAGCAGGACGCAG-3' | IDT | 5'-CTTCACCTTCCAGCTCCGCCTC-3' | IDT |

| Gene | sSNV | Taqman Probe | | PNA Blocker | |
|---|---|---|---|---|---|
| | | Sequence | Vendor | Sequence | Vendor |
| IDH1 | R132H | 5'-FAM-AGG+T+C+A+T+CAT+GC-Dab-3' | Exiqon | 5'-AGGTCGTCATGC-3' | PNA Bio |
| TERT | C228T | 5'-FAM-CCCAGCCCC+T+TCCGGGCCC-Dab-3' | Exiqon | 5'-CCCAGCCCCCTCCGGGCCC-3' | PNA Bio |
| TERT | C250T | 5'-FAM-CCGACCCC+T+TCCGGGTCCC-Dab-3' | Exiqon | 5'-CCGACCCCTCCGGGTCCC-3' | PNA Bio |

*Fig. 13*

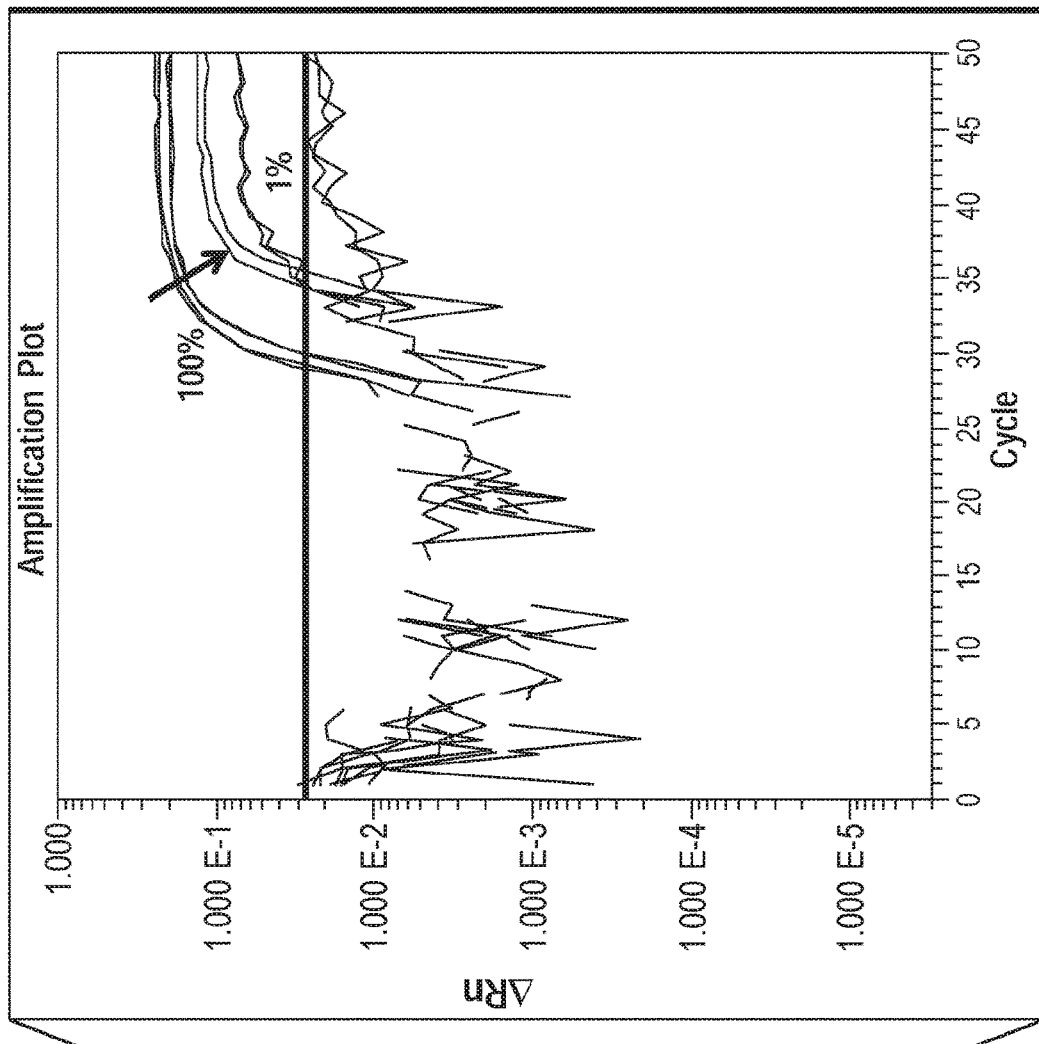
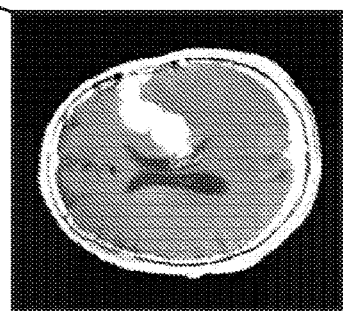
Fig. 16

Cell free circulating DNA sample acquisition to date

| Primary Tumor | Number of Patients | Number of patients with multiple time points | Number of samples analyzed |
|---|---|---|---|
| Melanoma | 5 | 2 | 7 |
| SCLC | 1 | 0 | 1 |
| NSCLC | 5 | 0 | 5 |
| Breast | 1 | 0 | 0 |
| Ovarian | 1 | 0 | 0 |

*Fig. 17*

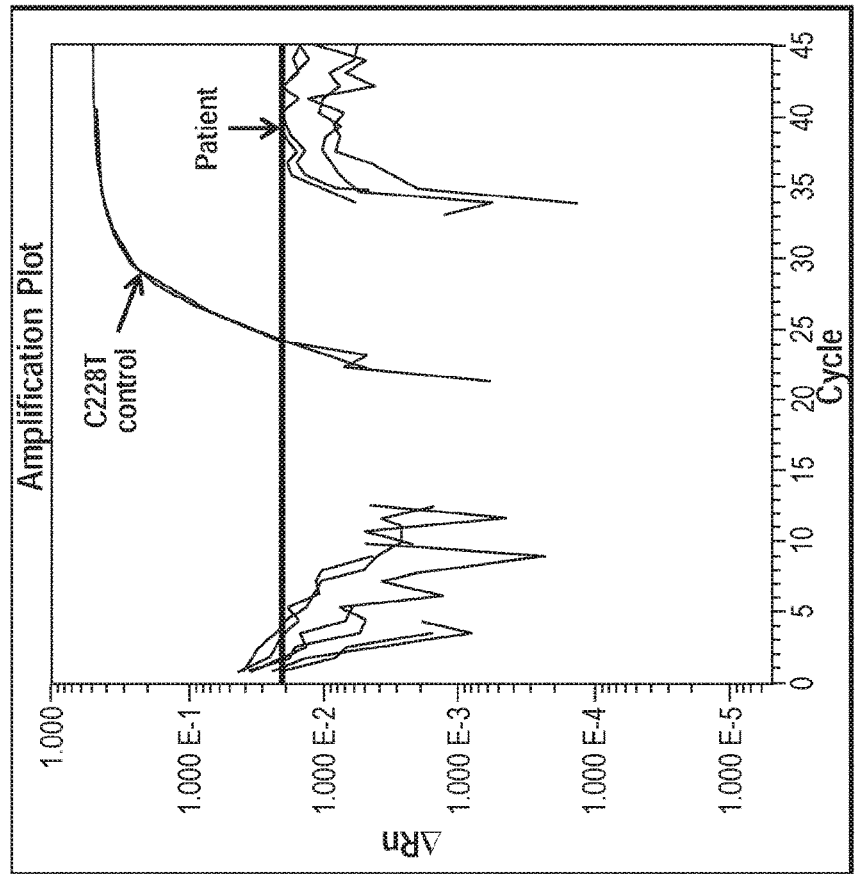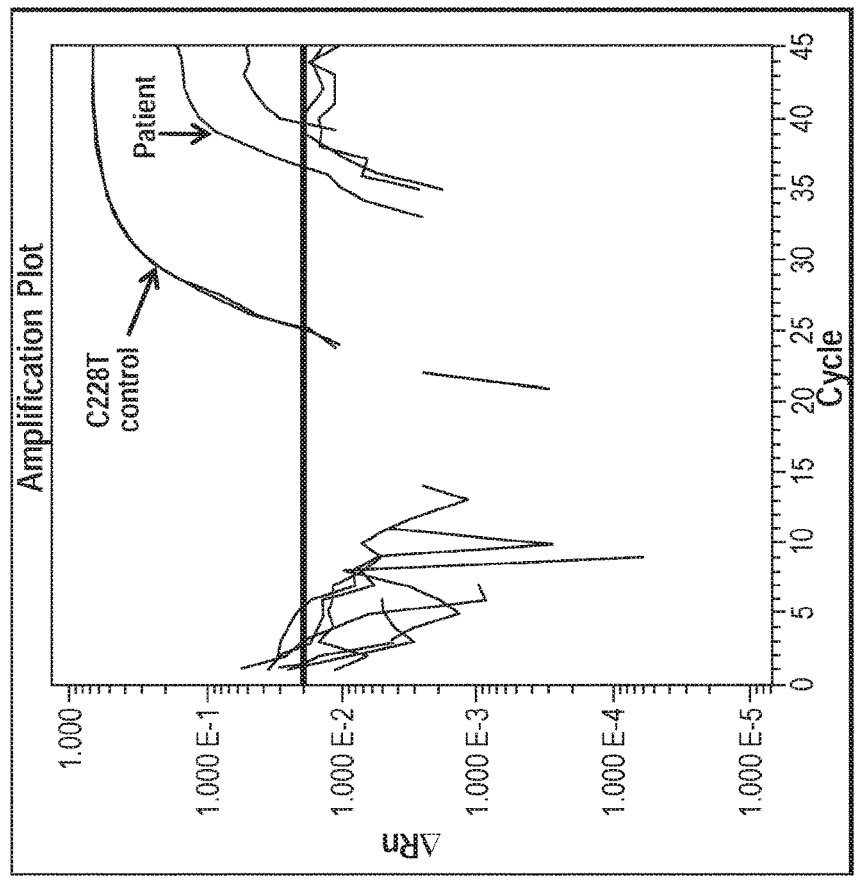
Fig. 19

SEQUENCE LISTING

<160> NUMBER OF SEQ ID NOS: 102

<210> SEQ ID NO 1
<211> LENGTH: 5
<212> TYPE: DNA
<213> ORGANISM: Artificial Sequence
<220> FEATURE:
<223> OTHER INFORMATION: synthetic sequence

<400> SEQUENCE: 1 ccttc                                                                  5

<210> SEQ ID NO 2
<211> LENGTH: 5
<212> TYPE: DNA
<213> ORGANISM: Artificial Sequence
<220> FEATURE:
<223> OTHER INFORMATION: synthetic sequence

<400> SEQUENCE: 2 ccctc                                                                  5

<210> SEQ ID NO 3
<211> LENGTH: 19
<212> TYPE: DNA
<213> ORGANISM: Artificial Sequence
<220> FEATURE:
<223> OTHER INFORMATION: synthetic sequence

<400> SEQUENCE: 3 cccagccct tccgggccc                                                   19

<210> SEQ ID NO 4
<211> LENGTH: 19
<212> TYPE: DNA
<213> ORGANISM: Artificial Sequence
<220> FEATURE:
<223> OTHER INFORMATION: synthetic sequence

<400> SEQUENCE: 4
cccagccccc tccgggccc                                                  19

<210> SEQ ID NO 5
<211> LENGTH: 5
<212> TYPE: DNA
<213> ORGANISM: Artificial Sequence
<220> FEATURE:
<223> OTHER INFORMATION: synthetic sequence

<400> SEQUENCE: 5 cttcc                                                                  5

<210> SEQ ID NO 6
<211> LENGTH: 5
<212> TYPE: DNA
<213> ORGANISM: Artificial Sequence
<220> FEATURE:
<223> OTHER INFORMATION: synthetic sequence

<400> SEQUENCE: 6 ctccc                                                                  5

<210> SEQ ID NO 7
<211> LENGTH: 19
<212> TYPE: DNA
<213> ORGANISM: Artificial Sequence
<220> FEATURE:
<223> OTHER INFORMATION: synthetic sequence

<400> SEQUENCE: 7
ccgacccctt ccgggtccc                                                  19

<210> SEQ ID NO 8
<211> LENGTH: 19
<212> TYPE: DNA
<213> ORGANISM: Artificial Sequence
<220> FEATURE:
<223> OTHER INFORMATION: synthetic sequence

<400> SEQUENCE: 8 ccgaccccptc ccgggtccc                                                 19

<210> SEQ ID NO 9
<211> LENGTH: 21
<212> TYPE: DNA
<213> ORGANISM: Artificial Sequence
<220> FEATURE:
<223> OTHER INFORMATION: synthetic sequence

<400> SEQUENCE: 9
cacgtgcgca gcaggacgca g                                               21

<210> SEQ ID NO 10
<211> LENGTH: 22
<212> TYPE: DNA
<213> ORGANISM: Artificial Sequence
<220> FEATURE:

<223> OTHER INFORMATION: synthetic sequence

<400> SEQUENCE: 10
cttcaccttc cagctccgcc tc                                      22

<210> SEQ ID NO 11
<211> LENGTH: 19
<212> TYPE: DNA
<213> ORGANISM: Artificial Sequence
<220> FEATURE:
<223> OTHER INFORMATION: synthetic sequence

<400> SEQUENCE: 11
cccagccccc tccgggccc                                          19

<210> SEQ ID NO 12
<211> LENGTH: 19
<212> TYPE: DNA
<213> ORGANISM: Artificial Sequence
<220> FEATURE:
<223> OTHER INFORMATION: synthetic sequence

<400> SEQUENCE: 12
ccgacccctc ccgggtccc                                          19

<210> SEQ ID NO 13
<211> LENGTH: 19
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (10)..(11)
<223> OTHER INFORMATION: LNA nucleotide

<400> SEQUENCE: 13
cccagcccct tccgggccc                                          19

<210> SEQ ID NO 14
<211> LENGTH: 19
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (9)..(10)
<223> OTHER INFORMATION: LNA nucleotide

<400> SEQUENCE: 14
ccgacccctt ccgggtccc                                          19

<210> SEQ ID NO 15
<211> LENGTH: 19
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: fluorescein
<220> FEATURE:
<221> NAME/KEY: misc_feature
<222> LOCATION: (10)..(11)
<223> OTHER INFORMATION: LNA nucleotide
<220> FEATURE:
<221> NAME/KEY: misc_feature

```
<222> LOCATION: (19)..(19)
<223> OTHER INFORMATION: diaminobenzidine

<400> SEQUENCE: 15
cccagcccct tccgggccc                                                19

<210> SEQ ID NO 16
<211> LENGTH: 19
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: fluorescein
<220> FEATURE:
<221> NAME/KEY: misc_feature
<222> LOCATION: (9)..(10)
<223> OTHER INFORMATION: LNA nucleotide
<220> FEATURE:
<221> NAME/KEY: misc_feature
<222> LOCATION: (19)..(19)
<223> OTHER INFORMATION: diaminobenzidine

<400> SEQUENCE: 16
ccgacccctt ccgggtccc                                                19

<210> SEQ ID NO 17
<211> LENGTH: 5
<212> TYPE: DNA
<213> ORGANISM: Artificial Sequence
<220> FEATURE:
<223> OTHER INFORMATION: synthetic sequence

<400> SEQUENCE: 17 gtcat                                                                5

<210> SEQ ID NO 18
<211> LENGTH: 5
<212> TYPE: DNA
<213> ORGANISM: Artificial Sequence
<220> FEATURE:
<223> OTHER INFORMATION: synthetic sequence

<400> SEQUENCE: 18 gtcgt                                                                5

<210> SEQ ID NO 19
<211> LENGTH: 12
<212> TYPE: DNA
<213> ORGANISM: Artificial Sequence
<220> FEATURE:
<223> OTHER INFORMATION: synthetic sequence

<400> SEQUENCE: 19
aggtcatcat gc                                                       12

<210> SEQ ID NO 20
<211> LENGTH: 12
<212> TYPE: DNA
<213> ORGANISM: Artificial Sequence
<220> FEATURE:
<223> OTHER INFORMATION: synthetic sequence

<400> SEQUENCE: 20
aggtcgtcat gc                                                       12
```

```
<210> SEQ ID NO 21
<211> LENGTH: 5
<212> TYPE: DNA
<213> ORGANISM: Artificial Sequence
<220> FEATURE:
<223> OTHER INFORMATION: synthetic sequence

<400> SEQUENCE: 21 gttgt                                                                      5

<210> SEQ ID NO 22
<211> LENGTH: 12
<212> TYPE: DNA
<213> ORGANISM: Artificial Sequence
<220> FEATURE:
<223> OTHER INFORMATION: synthetic sequence

<400> SEQUENCE: 22
aggttgtcat gc                                                             12

<210> SEQ ID NO 23
<211> LENGTH: 5
<212> TYPE: DNA
<213> ORGANISM: Artificial Sequence
<220> FEATURE:
<223> OTHER INFORMATION: synthetic sequence

<400> SEQUENCE: 23 gtggt                                                                      5

<210> SEQ ID NO 24
<211> LENGTH: 12
<212> TYPE: DNA
<213> ORGANISM: Artificial Sequence
<220> FEATURE:
<223> OTHER INFORMATION: synthetic sequence

<400> SEQUENCE: 24
aggtggtcat gc                                                             12

<210> SEQ ID NO 25
<211> LENGTH: 5
<212> TYPE: DNA
<213> ORGANISM: Artificial Sequence
<220> FEATURE:
<223> OTHER INFORMATION: synthetic sequence

<400> SEQUENCE: 25 gtagt                                                                      5

<210> SEQ ID NO 26
<211> LENGTH: 12
<212> TYPE: DNA
<213> ORGANISM: Artificial Sequence
<220> FEATURE:
<223> OTHER INFORMATION: synthetic sequence

<400> SEQUENCE: 26
aggtagtcat gc                                                             12

<210> SEQ ID NO 27
<211> LENGTH: 5
<212> TYPE: DNA
<213> ORGANISM: Artificial Sequence
<220> FEATURE:
<223> OTHER INFORMATION: synthetic sequence
```

```
<400> SEQUENCE: 27 gtctt                                                                    5

<210> SEQ ID NO 28
<211> LENGTH: 5
<212> TYPE: DNA
<213> ORGANISM: Artificial Sequence
<220> FEATURE:
<223> OTHER INFORMATION: synthetic sequence

<400> SEQUENCE: 28 gtctt                                                                    5

<210> SEQ ID NO 29
<211> LENGTH: 28
<212> TYPE: DNA
<213> ORGANISM: Artificial Sequence
<220> FEATURE:
<223> OTHER INFORMATION: synthetic sequence

<400> SEQUENCE: 29
ccggcttgtg agtggatggg taaaacct                                           28

<210> SEQ ID NO 30
<211> LENGTH: 31
<212> TYPE: DNA
<213> ORGANISM: Artificial Sequence
<220> FEATURE:
<223> OTHER INFORMATION: synthetic sequence

<400> SEQUENCE: 30
cattattgcc aacatgactt acttgatccc c                                       31

<210> SEQ ID NO 31
<211> LENGTH: 12
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (4)..(8)
<223> OTHER INFORMATION: LNA nucleotide
<220> FEATURE:
<221> NAME/KEY: misc_feature
<222> LOCATION: (11)..(11)
<223> OTHER INFORMATION: LNA nucleotide

<400> SEQUENCE: 31
aggtcatcat gc                                                           12

<210> SEQ ID NO 32
<211> LENGTH: 12
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (4)..(9)
<223> OTHER INFORMATION: LNA nucleotide

<400> SEQUENCE: 32
aggttgtcat gc                                                           12

<210> SEQ ID NO 33
```

```
<211> LENGTH: 12
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (5)..(8)
<223> OTHER INFORMATION: LNA nucleotide
<220> FEATURE:
<221> NAME/KEY: misc_feature
<222> LOCATION: (11)..(11)
<223> OTHER INFORMATION: LNA nucleotide

<400> SEQUENCE: 33
aggtggtcat gc                                                           12

<210> SEQ ID NO 34
<211> LENGTH: 12
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (5)..(8)
<223> OTHER INFORMATION: LNA nucleotide
<220> FEATURE:
<221> NAME/KEY: misc_feature
<222> LOCATION: (10)..(11)
<223> OTHER INFORMATION: LNA nucleotide

<400> SEQUENCE: 34
aggtagtcat gc                                                           12

<210> SEQ ID NO 35
<211> LENGTH: 12
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (4)..(8)
<223> OTHER INFORMATION: LNA nucleotide
<220> FEATURE:
<221> NAME/KEY: misc_feature
<222> LOCATION: (11)..(11)
<223> OTHER INFORMATION: LNA nucleotide

<400> SEQUENCE: 35
aggtcttcat gc                                                           12

<210> SEQ ID NO 36
<211> LENGTH: 12
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: fluorescein
<220> FEATURE:
<221> NAME/KEY: misc_feature
<222> LOCATION: (4)..(8)
<223> OTHER INFORMATION: LNA nucleotide
<220> FEATURE:
<221> NAME/KEY: misc_feature
<222> LOCATION: (11)..(11)
<223> OTHER INFORMATION: LNA nucleotide
<220> FEATURE:
<221> NAME/KEY: misc_feature
```

```
<222> LOCATION: (12)..(12)
<223> OTHER INFORMATION: diaminobenzidine

<400> SEQUENCE: 36
aggtcatcat gc                                                        12

<210> SEQ ID NO 37
<211> LENGTH: 12
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: fluorescent moiety
<220> FEATURE:
<221> NAME/KEY: misc_feature
<222> LOCATION: (4)..(9)
<223> OTHER INFORMATION: LNA nucleotide
<220> FEATURE:
<221> NAME/KEY: misc_feature
<222> LOCATION: (12)..(12)
<223> OTHER INFORMATION: diaminobenzidine

<400> SEQUENCE: 37
aggttgtcat gc                                                        12

<210> SEQ ID NO 38
<211> LENGTH: 12
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: fluorescent moiety
<220> FEATURE:
<221> NAME/KEY: misc_feature
<222> LOCATION: (5)..(8)
<223> OTHER INFORMATION: LNA nucleotide
<220> FEATURE:
<221> NAME/KEY: misc_feature
<222> LOCATION: (11)..(11)
<223> OTHER INFORMATION: LNA nucleotide
<220> FEATURE:
<221> NAME/KEY: misc_feature
<222> LOCATION: (12)..(12)
<223> OTHER INFORMATION: diaminobenzidine

<400> SEQUENCE: 38
aggtggtcat gc                                                        12

<210> SEQ ID NO 39
<211> LENGTH: 12
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: fluorescent moiety
<220> FEATURE:
<221> NAME/KEY: misc_feature
<222> LOCATION: (5)..(8)
<223> OTHER INFORMATION: LNA nucleotide
<220> FEATURE:
<221> NAME/KEY: misc_feature
<222> LOCATION: (10)..(11)
<223> OTHER INFORMATION: LNA nucleotide
<220> FEATURE:
```

```
<221> NAME/KEY: misc_feature
<222> LOCATION: (12)..(12)
<223> OTHER INFORMATION: diaminobenzidine

<400> SEQUENCE: 39
aggtagtcat gc                                                              12

<210> SEQ ID NO 40
<211> LENGTH: 12
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: fluorescent moiety
<220> FEATURE:
<221> NAME/KEY: misc_feature
<222> LOCATION: (4)..(8)
<223> OTHER INFORMATION: LNA nucleotide
<220> FEATURE:
<221> NAME/KEY: misc_feature
<222> LOCATION: (11)..(11)
<223> OTHER INFORMATION: LNA nucleotide
<220> FEATURE:
<221> NAME/KEY: misc_feature
<222> LOCATION: (12)..(12)
<223> OTHER INFORMATION: diaminobenzidine

<400> SEQUENCE: 40
aggtcttcat gc                                                              12

<210> SEQ ID NO 41
<211> LENGTH: 5
<212> TYPE: DNA
<213> ORGANISM: Artificial Sequence
<220> FEATURE:
<223> OTHER INFORMATION: synthetic sequence

<400> SEQUENCE: 41 tcact                                                                       5

<210> SEQ ID NO 42
<211> LENGTH: 5
<212> TYPE: DNA
<213> ORGANISM: Artificial Sequence
<220> FEATURE:
<223> OTHER INFORMATION: synthetic sequence

<400> SEQUENCE: 42 tctct                                                                       5

<210> SEQ ID NO 43
<211> LENGTH: 21
<212> TYPE: DNA
<213> ORGANISM: Artificial Sequence
<220> FEATURE:
<223> OTHER INFORMATION: synthetic sequence

<400> SEQUENCE: 43
acagggcatg gagagtgggt c                                                    21

<210> SEQ ID NO 44
<211> LENGTH: 23
<212> TYPE: DNA
<213> ORGANISM: Artificial Sequence
<220> FEATURE:
<223> OTHER INFORMATION: synthetic sequence
```

<400> SEQUENCE: 44
caaactgatg ggacccactc cat                                         23

<210> SEQ ID NO 45
<211> LENGTH: 24
<212> TYPE: DNA
<213> ORGANISM: Artificial Sequence
<220> FEATURE:
<223> OTHER INFORMATION: synthetic sequence

<400> SEQUENCE: 45
catcgagatt tcactgtagc taga                                        24

<210> SEQ ID NO 46
<211> LENGTH: 15
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (3)..(4)
<223> OTHER INFORMATION: LNA nucleotide
<220> FEATURE:
<221> NAME/KEY: misc_feature
<222> LOCATION: (5)..(6)
<223> OTHER INFORMATION: LNA nucleotide
<220> FEATURE:
<221> NAME/KEY: misc_feature
<222> LOCATION: (6)..(7)
<223> OTHER INFORMATION: LNA nucleotide
<220> FEATURE:
<221> NAME/KEY: misc_feature
<222> LOCATION: (7)..(8)
<223> OTHER INFORMATION: LNA nucleotide
<220> FEATURE:
<221> NAME/KEY: misc_feature
<222> LOCATION: (8)..(9)
<223> OTHER INFORMATION: LNA nucleotide
<220> FEATURE:
<221> NAME/KEY: misc_feature
<222> LOCATION: (10)..(11)
<223> OTHER INFORMATION: LNA nucleotide
<220> FEATURE:
<221> NAME/KEY: misc_feature
<222> LOCATION: (12)..(13)
<223> OTHER INFORMATION: LNA nucleotide
<220> FEATURE:
<221> NAME/KEY: misc_feature
<222> LOCATION: (14)..(15)
<223> OTHER INFORMATION: LNA nucleotide

<400> SEQUENCE: 46
agatttctct gtagc                                                  15

<210> SEQ ID NO 47
<211> LENGTH: 15
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5-FAM
<220> FEATURE:
<221> NAME/KEY: misc_feature
<222> LOCATION: (3)..(4)
<223> OTHER INFORMATION: LNA nucleotide
<220> FEATURE:
<221> NAME/KEY: misc_feature
<222> LOCATION: (5)..(6)

```
<223> OTHER INFORMATION: LNA nucleotide
<220> FEATURE:
<221> NAME/KEY: misc_feature
<222> LOCATION: (6)..(7)
<223> OTHER INFORMATION: LNA nucleotide
<220> FEATURE:
<221> NAME/KEY: misc_feature
<222> LOCATION: (7)..(8)
<223> OTHER INFORMATION: LNA nucleotide
<220> FEATURE:
<221> NAME/KEY: misc_feature
<222> LOCATION: (8)..(9)
<223> OTHER INFORMATION: LNA nucleotide
<220> FEATURE:
<221> NAME/KEY: misc_feature
<222> LOCATION: (10)..(11)
<223> OTHER INFORMATION: LNA nucleotide
<220> FEATURE:
<221> NAME/KEY: misc_feature
<222> LOCATION: (12)..(13)
<223> OTHER INFORMATION: LNA nucleotide
<220> FEATURE:
<221> NAME/KEY: misc_feature
<222> LOCATION: (14)..(15)
<223> OTHER INFORMATION: LNA nucleotide
<220> FEATURE:
<221> NAME/KEY: misc_feature
<222> LOCATION: (15)..(15)
<223> OTHER INFORMATION: Dab-3

<400> SEQUENCE: 47
agatttctct gtagc                                              15

<210> SEQ ID NO 48
<211> LENGTH: 15
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5-MAXN
<220> FEATURE:
<221> NAME/KEY: misc_feature
<222> LOCATION: (3)..(4)
<223> OTHER INFORMATION: LNA nucleotide
<220> FEATURE:
<221> NAME/KEY: misc_feature
<222> LOCATION: (5)..(6)
<223> OTHER INFORMATION: LNA nucleotide
<220> FEATURE:
<221> NAME/KEY: misc_feature
<222> LOCATION: (6)..(7)
<223> OTHER INFORMATION: LNA nucleotide
<220> FEATURE:
<221> NAME/KEY: misc_feature
<222> LOCATION: (7)..(8)
<223> OTHER INFORMATION: LNA nucleotide
<220> FEATURE:
<221> NAME/KEY: misc_feature
<222> LOCATION: (8)..(9)
<223> OTHER INFORMATION: LNA nucleotide
<220> FEATURE:
<221> NAME/KEY: misc_feature
<222> LOCATION: (10)..(11)
<223> OTHER INFORMATION: LNA nucleotide
<220> FEATURE:
<221> NAME/KEY: misc_feature
<222> LOCATION: (12)..(13)
<223> OTHER INFORMATION: LNA nucleotide
<220> FEATURE:
<221> NAME/KEY: misc_feature
<222> LOCATION: (14)..(15)
<223> OTHER INFORMATION: LNA nucleotide
<220> FEATURE:
<221> NAME/KEY: misc_feature
```

```
<222> LOCATION: (15)..(15)
<223> OTHER INFORMATION: Dab-3

<400> SEQUENCE: 48
agatttctct gtagc                                              15

<210> SEQ ID NO 49
<211> LENGTH: 5
<212> TYPE: DNA
<213> ORGANISM: Artificial Sequence
<220> FEATURE:
<223> OTHER INFORMATION: synthetic sequence

<400> SEQUENCE: 49 acaag                                                          5

<210> SEQ ID NO 50
<211> LENGTH: 5
<212> TYPE: DNA
<213> ORGANISM: Artificial Sequence
<220> FEATURE:
<223> OTHER INFORMATION: synthetic sequence

<400> SEQUENCE: 50 acgag                                                          5

<210> SEQ ID NO 51
<211> LENGTH: 5
<212> TYPE: DNA
<213> ORGANISM: Artificial Sequence
<220> FEATURE:
<223> OTHER INFORMATION: synthetic sequence

<400> SEQUENCE: 51 aaaag                                                          5

<210> SEQ ID NO 52
<211> LENGTH: 24
<212> TYPE: DNA
<213> ORGANISM: Artificial Sequence
<220> FEATURE:
<223> OTHER INFORMATION: synthetic sequence

<400> SEQUENCE: 52
agtggttata gatggtgaaa cctg                                    24

<210> SEQ ID NO 53
<211> LENGTH: 20
<212> TYPE: DNA
<213> ORGANISM: Artificial Sequence
<220> FEATURE:
<223> OTHER INFORMATION: synthetic sequence

<400> SEQUENCE: 53
acagaggaag ccttcgcctg                                         20

<210> SEQ ID NO 54
<211> LENGTH: 20
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (20)..(20)
<223> OTHER INFORMATION: 3-KK
```

```
<400> SEQUENCE: 54
cagctggaca agaagagtac                                              20

<210> SEQ ID NO 55
<211> LENGTH: 16
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (5)..(5)
<223> OTHER INFORMATION: LNA nucleotide
<220> FEATURE:
<221> NAME/KEY: misc_feature
<222> LOCATION: (7)..(8)
<223> OTHER INFORMATION: LNA nucleotide
<220> FEATURE:
<221> NAME/KEY: misc_feature
<222> LOCATION: (10)..(10)
<223> OTHER INFORMATION: LNA nucleotide
<220> FEATURE:
<221> NAME/KEY: misc_feature
<222> LOCATION: (12)..(12)
<223> OTHER INFORMATION: LNA nucleotide

<400> SEQUENCE: 55
ctggacgaga agagta                                                  16

<210> SEQ ID NO 56
<211> LENGTH: 19
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (4)..(4)
<223> OTHER INFORMATION: LNA nucleotide
<220> FEATURE:
<221> NAME/KEY: misc_feature
<222> LOCATION: (9)..(11)
<223> OTHER INFORMATION: LNA nucleotide
<220> FEATURE:
<221> NAME/KEY: misc_feature
<222> LOCATION: (15)..(15)
<223> OTHER INFORMATION: LNA nucleotide
<220> FEATURE:
<221> NAME/KEY: misc_feature
<222> LOCATION: (17)..(17)
<223> OTHER INFORMATION: LNA nucleotide

<400> SEQUENCE: 56
cagctggaaa agaagagta                                               19

<210> SEQ ID NO 57
<211> LENGTH: 16
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5-FAM
<220> FEATURE:
<221> NAME/KEY: misc_feature
<222> LOCATION: (4)..(5)
<223> OTHER INFORMATION: LNA nucleotide
<220> FEATURE:
<221> NAME/KEY: misc_feature
<222> LOCATION: (6)..(7)
<223> OTHER INFORMATION: LNA nucleotide
```

```
<220> FEATURE:
<221> NAME/KEY: misc_feature
<222> LOCATION: (7)..(8)
<223> OTHER INFORMATION: LNA nucleotide
<220> FEATURE:
<221> NAME/KEY: misc_feature
<222> LOCATION: (9)..(10)
<223> OTHER INFORMATION: LNA nucleotide
<220> FEATURE:
<221> NAME/KEY: misc_feature
<222> LOCATION: (11)..(12)
<223> OTHER INFORMATION: LNA nucleotide
<220> FEATURE:
<221> NAME/KEY: misc_feature
<222> LOCATION: (16)..(16)
<223> OTHER INFORMATION: Dab-3

<400> SEQUENCE: 57
ctggacgaga agagta                                                     16

<210> SEQ ID NO 58
<211> LENGTH: 19
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5-FAM
<220> FEATURE:
<221> NAME/KEY: misc_feature
<222> LOCATION: (3)..(5)
<223> OTHER INFORMATION: LNA nucleotide
<220> FEATURE:
<221> NAME/KEY: misc_feature
<222> LOCATION: (9)..(10)
<223> OTHER INFORMATION: LNA nucleotide
<220> FEATURE:
<221> NAME/KEY: misc_feature
<222> LOCATION: (10)..(11)
<223> OTHER INFORMATION: LNA nucleotide
<220> FEATURE:
<221> NAME/KEY: misc_feature
<222> LOCATION: (11)..(12)
<223> OTHER INFORMATION: LNA nucleotide
<220> FEATURE:
<221> NAME/KEY: misc_feature
<222> LOCATION: (14)..(15)
<223> OTHER INFORMATION: LNA nucleotide
<220> FEATURE:
<221> NAME/KEY: misc_feature
<222> LOCATION: (16)..(17)
<223> OTHER INFORMATION: LNA nucleotide
<220> FEATURE:
<221> NAME/KEY: misc_feature
<222> LOCATION: (19)..(19)
<223> OTHER INFORMATION: Dab-3

<400> SEQUENCE: 58
cagctggaaa agaagagta                                                  19

<210> SEQ ID NO 59
<211> LENGTH: 16
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5-MAXN
<220> FEATURE:
<221> NAME/KEY: misc_feature
<222> LOCATION: (4)..(5)
```

```
<223> OTHER INFORMATION: LNA nucleotide
<220> FEATURE:
<221> NAME/KEY: misc_feature
<222> LOCATION: (6)..(7)
<223> OTHER INFORMATION: LNA nucleotide
<220> FEATURE:
<221> NAME/KEY: misc_feature
<222> LOCATION: (7)..(8)
<223> OTHER INFORMATION: LNA nucleotide
<220> FEATURE:
<221> NAME/KEY: misc_feature
<222> LOCATION: (9)..(10)
<223> OTHER INFORMATION: LNA nucleotide
<220> FEATURE:
<221> NAME/KEY: misc_feature
<222> LOCATION: (11)..(12)
<223> OTHER INFORMATION: LNA nucleotide
<220> FEATURE:
<221> NAME/KEY: misc_feature
<222> LOCATION: (16)..(16)
<223> OTHER INFORMATION: Dab-3

<400> SEQUENCE: 59
ctggacgaga agagta                                                     16

<210> SEQ ID NO 60
<211> LENGTH: 19
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5-MAXN
<220> FEATURE:
<221> NAME/KEY: misc_feature
<222> LOCATION: (3)..(4)
<223> OTHER INFORMATION: LNA nucleotide
<220> FEATURE:
<221> NAME/KEY: misc_feature
<222> LOCATION: (8)..(9)
<223> OTHER INFORMATION: LNA nucleotide
<220> FEATURE:
<221> NAME/KEY: misc_feature
<222> LOCATION: (9)..(10)
<223> OTHER INFORMATION: LNA nucleotide
<220> FEATURE:
<221> NAME/KEY: misc_feature
<222> LOCATION: (10)..(11)
<223> OTHER INFORMATION: LNA nucleotide
<220> FEATURE:
<221> NAME/KEY: misc_feature
<222> LOCATION: (14)..(15)
<223> OTHER INFORMATION: LNA nucleotide
<220> FEATURE:
<221> NAME/KEY: misc_feature
<222> LOCATION: (16)..(17)
<223> OTHER INFORMATION: LNA nucleotide
<220> FEATURE:
<221> NAME/KEY: misc_feature
<222> LOCATION: (19)..(19)
<223> OTHER INFORMATION: Dab-3

<400> SEQUENCE: 60
cagctggaaa agaagagta                                                  19

<210> SEQ ID NO 61
<211> LENGTH: 5
<212> TYPE: DNA
<213> ORGANISM: Artificial Sequence
<220> FEATURE:
<223> OTHER INFORMATION: synthetic sequence

<400> SEQUENCE: 61
```

```
tcgag                                                            5

<210> SEQ ID NO 62
<211> LENGTH: 5
<212> TYPE: DNA
<213> ORGANISM: Artificial Sequence
<220> FEATURE:
<223> OTHER INFORMATION: synthetic sequence

<400> SEQUENCE: 62 tcaag                                                            5

<210> SEQ ID NO 63
<211> LENGTH: 5
<212> TYPE: DNA
<213> ORGANISM: Artificial Sequence
<220> FEATURE:
<223> OTHER INFORMATION: synthetic sequence

<400> SEQUENCE: 63 ccaaa                                                            5

<210> SEQ ID NO 64
<211> LENGTH: 5
<212> TYPE: DNA
<213> ORGANISM: Artificial Sequence
<220> FEATURE:
<223> OTHER INFORMATION: synthetic sequence

<400> SEQUENCE: 64 cctaa                                                            5

<210> SEQ ID NO 65
<211> LENGTH: 5
<212> TYPE: DNA
<213> ORGANISM: Artificial Sequence
<220> FEATURE:
<223> OTHER INFORMATION: synthetic sequence

<400> SEQUENCE: 65 cccaa                                                            5

<210> SEQ ID NO 66
<211> LENGTH: 21
<212> TYPE: DNA
<213> ORGANISM: Artificial Sequence
<220> FEATURE:
<223> OTHER INFORMATION: synthetic sequence

<400> SEQUENCE: 66
ttggaccgcg tagctgaccc t                                         21

<210> SEQ ID NO 67
<211> LENGTH: 25
<212> TYPE: DNA
<213> ORGANISM: Artificial Sequence
<220> FEATURE:
<223> OTHER INFORMATION: synthetic sequence

<400> SEQUENCE: 67
ccctaagttt gtaagtagtg ctata                                     25

<210> SEQ ID NO 68
<211> LENGTH: 23
<212> TYPE: DNA
```

```
<213> ORGANISM: Artificial Sequence
<220> FEATURE:
<223> OTHER INFORMATION: synthetic sequence

<400> SEQUENCE: 68
gctgggaaat aggtttcatg gac                                          23

<210> SEQ ID NO 69
<211> LENGTH: 24
<212> TYPE: DNA
<213> ORGANISM: Artificial Sequence
<220> FEATURE:
<223> OTHER INFORMATION: synthetic sequence

<400> SEQUENCE: 69
tcactaagcg ctactagaaa catg                                         24

<210> SEQ ID NO 70
<211> LENGTH: 18
<212> TYPE: DNA
<213> ORGANISM: Artificial Sequence
<220> FEATURE:
<223> OTHER INFORMATION: synthetic sequence

<400> SEQUENCE: 70
ttagagttcg agtcccca                                                18

<210> SEQ ID NO 71
<211> LENGTH: 18
<212> TYPE: DNA
<213> ORGANISM: Artificial Sequence
<220> FEATURE:
<223> OTHER INFORMATION: synthetic sequence

<400> SEQUENCE: 71
ggggccaaag gtcagaga                                                18

<210> SEQ ID NO 72
<211> LENGTH: 17
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (6)..(6)
<223> OTHER INFORMATION: LNA nucleotide
<220> FEATURE:
<221> NAME/KEY: misc_feature
<222> LOCATION: (8)..(9)
<223> OTHER INFORMATION: LNA nucleotide
<220> FEATURE:
<221> NAME/KEY: misc_feature
<222> LOCATION: (12)..(12)
<223> OTHER INFORMATION: LNA nucleotide

<400> SEQUENCE: 72
agagttcaag tccccac                                                 17

<210> SEQ ID NO 73
<211> LENGTH: 18
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (8)..(9)
<223> OTHER INFORMATION: LNA nucleotide
```

<400> SEQUENCE: 73
aggggcctaa ggtcagag                                           18

<210> SEQ ID NO 74
<211> LENGTH: 17
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (6)..(7)
<223> OTHER INFORMATION: LNA nucleotide

<400> SEQUENCE: 74
gggcccaagg tcagaga                                            17

<210> SEQ ID NO 75
<211> LENGTH: 17
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5-FAM
<220> FEATURE:
<221> NAME/KEY: misc_feature
<222> LOCATION: (5)..(6)
<223> OTHER INFORMATION: LNA nucleotide
<220> FEATURE:
<221> NAME/KEY: misc_feature
<222> LOCATION: (7)..(8)
<223> OTHER INFORMATION: LNA nucleotide
<220> FEATURE:
<221> NAME/KEY: misc_feature
<222> LOCATION: (8)..(9)
<223> OTHER INFORMATION: LNA nucleotide
<220> FEATURE:
<221> NAME/KEY: misc_feature
<222> LOCATION: (11)..(12)
<223> OTHER INFORMATION: LNA nucleotide
<220> FEATURE:
<221> NAME/KEY: misc_feature
<222> LOCATION: (17)..(17)
<223> OTHER INFORMATION: Dab-3

<400> SEQUENCE: 75
agagttcaag tccccac                                            17

<210> SEQ ID NO 76
<211> LENGTH: 18
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5-FAM
<220> FEATURE:
<221> NAME/KEY: misc_feature
<222> LOCATION: (7)..(8)
<223> OTHER INFORMATION: LNA nucleotide
<220> FEATURE:
<221> NAME/KEY: misc_feature
<222> LOCATION: (8)..(9)
<223> OTHER INFORMATION: LNA nucleotide
<220> FEATURE:
<221> NAME/KEY: misc_feature
<222> LOCATION: (18)..(18)

<223> OTHER INFORMATION: Dab-3

<400> SEQUENCE: 76
aggggcctaa ggtcagag                                                    18

<210> SEQ ID NO 77
<211> LENGTH: 17
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5-FAM
<220> FEATURE:
<221> NAME/KEY: misc_feature
<222> LOCATION: (5)..(6)
<223> OTHER INFORMATION: LNA nucleotide
<220> FEATURE:
<221> NAME/KEY: misc_feature
<222> LOCATION: (6)..(7)
<223> OTHER INFORMATION: LNA nucleotide
<220> FEATURE:
<221> NAME/KEY: misc_feature
<222> LOCATION: (17)..(17)
<223> OTHER INFORMATION: Dab-3

<400> SEQUENCE: 77
gggcccaagg tcagaga                                                     17

<210> SEQ ID NO 78
<211> LENGTH: 17
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5-MAXN
<220> FEATURE:
<221> NAME/KEY: misc_feature
<222> LOCATION: (5)..(6)
<223> OTHER INFORMATION: LNA nucleotide
<220> FEATURE:
<221> NAME/KEY: misc_feature
<222> LOCATION: (7)..(8)
<223> OTHER INFORMATION: LNA nucleotide
<220> FEATURE:
<221> NAME/KEY: misc_feature
<222> LOCATION: (8)..(9)
<223> OTHER INFORMATION: LNA nucleotide
<220> FEATURE:
<221> NAME/KEY: misc_feature
<222> LOCATION: (11)..(12)
<223> OTHER INFORMATION: LNA nucleotide
<220> FEATURE:
<221> NAME/KEY: misc_feature
<222> LOCATION: (17)..(17)
<223> OTHER INFORMATION: Dab-3

<400> SEQUENCE: 78
agagttcaag tccccac                                                     17

<210> SEQ ID NO 79
<211> LENGTH: 18
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature

```
<222> LOCATION: (1)..(1)
<223> OTHER INFORMATION: 5-MAXN
<220> FEATURE:
<221> NAME/KEY: misc_feature
<222> LOCATION: (7)..(8)
<223> OTHER INFORMATION: LNA nucleotide
<220> FEATURE:
<221> NAME/KEY: misc_feature
<222> LOCATION: (8)..(9)
<223> OTHER INFORMATION: LNA nucleotide
<220> FEATURE:
<221> NAME/KEY: misc_feature
<222> LOCATION: (18)..(18)
<223> OTHER INFORMATION: Dab-3

<400> SEQUENCE: 79
aggggcctaa ggtcagag                                                   18

<210> SEQ ID NO 80
<211> LENGTH: 17
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5-MAXN
<220> FEATURE:
<221> NAME/KEY: misc_feature
<222> LOCATION: (5)..(6)
<223> OTHER INFORMATION: LNA nucleotide
<220> FEATURE:
<221> NAME/KEY: misc_feature
<222> LOCATION: (6)..(7)
<223> OTHER INFORMATION: LNA nucleotide
<220> FEATURE:
<221> NAME/KEY: misc_feature
<222> LOCATION: (17)..(17)
<223> OTHER INFORMATION: Dab-3

<400> SEQUENCE: 80
gggcccaagg tcagaga                                                    17

<210> SEQ ID NO 81
<211> LENGTH: 5
<212> TYPE: DNA
<213> ORGANISM: Artificial Sequence
<220> FEATURE:
<223> OTHER INFORMATION: synthetic sequence

<400> SEQUENCE: 81 ccagc                                                                  5

<210> SEQ ID NO 82
<211> LENGTH: 5
<212> TYPE: DNA
<213> ORGANISM: Artificial Sequence
<220> FEATURE:
<223> OTHER INFORMATION: synthetic sequence

<400> SEQUENCE: 82 cctgc                                                                  5

<210> SEQ ID NO 83
<211> LENGTH: 20
<212> TYPE: DNA
<213> ORGANISM: Artificial Sequence
<220> FEATURE:
<223> OTHER INFORMATION: synthetic sequence
```

```
<400> SEQUENCE: 83
gcagattggg ccttggggcg                                              20

<210> SEQ ID NO 84
<211> LENGTH: 21
<212> TYPE: DNA
<213> ORGANISM: Artificial Sequence
<220> FEATURE:
<223> OTHER INFORMATION: synthetic sequence

<400> SEQUENCE: 84
tcgctgaggg cgacgagaaa c                                            21

<210> SEQ ID NO 85
<211> LENGTH: 17
<212> TYPE: DNA
<213> ORGANISM: Artificial Sequence
<220> FEATURE:
<223> OTHER INFORMATION: synthetic sequence

<400> SEQUENCE: 85
gggccagcgg tcggagc                                                 17

<210> SEQ ID NO 86
<211> LENGTH: 14
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (4)..(4)
<223> OTHER INFORMATION: LNA nucleotide
<220> FEATURE:
<221> NAME/KEY: misc_feature
<222> LOCATION: (6)..(7)
<223> OTHER INFORMATION: LNA nucleotide

<400> SEQUENCE: 86
gggcctgcgg tcgg                                                    14

<210> SEQ ID NO 87
<211> LENGTH: 14
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5-FAM
<220> FEATURE:
<221> NAME/KEY: misc_feature
<222> LOCATION: (3)..(4)
<223> OTHER INFORMATION: LNA nucleotide
<220> FEATURE:
<221> NAME/KEY: misc_feature
<222> LOCATION: (5)..(6)
<223> OTHER INFORMATION: LNA nucleotide
<220> FEATURE:
<221> NAME/KEY: misc_feature
<222> LOCATION: (6)..(7)
<223> OTHER INFORMATION: LNA nucleotide
<220> FEATURE:
<221> NAME/KEY: misc_feature
<222> LOCATION: (14)..(14)
<223> OTHER INFORMATION: Dab-3

<400> SEQUENCE: 87
gggcctgcgg tcgg                                                    14
```

```
<210> SEQ ID NO 88
<211> LENGTH: 14
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5-MAXN
<220> FEATURE:
<221> NAME/KEY: misc_feature
<222> LOCATION: (3)..(4)
<223> OTHER INFORMATION: LNA nucleotide
<220> FEATURE:
<221> NAME/KEY: misc_feature
<222> LOCATION: (5)..(6)
<223> OTHER INFORMATION: LNA nucleotide
<220> FEATURE:
<221> NAME/KEY: misc_feature
<222> LOCATION: (6)..(7)
<223> OTHER INFORMATION: LNA nucleotide
<220> FEATURE:
<221> NAME/KEY: misc_feature
<222> LOCATION: (14)..(14)
<223> OTHER INFORMATION: Dab-3

<400> SEQUENCE: 88
gggcctgcgg tcgg                                                  14

<210> SEQ ID NO 89
<211> LENGTH: 5
<212> TYPE: DNA
<213> ORGANISM: Artificial Sequence
<220> FEATURE:
<223> OTHER INFORMATION: synthetic sequence

<400> SEQUENCE: 89 caaga                                                             5

<210> SEQ ID NO 90
<211> LENGTH: 5
<212> TYPE: DNA
<213> ORGANISM: Artificial Sequence
<220> FEATURE:
<223> OTHER INFORMATION: synthetic sequence

<400> SEQUENCE: 90 catga                                                             5

<210> SEQ ID NO 91
<211> LENGTH: 5
<212> TYPE: DNA
<213> ORGANISM: Artificial Sequence
<220> FEATURE:
<223> OTHER INFORMATION: synthetic sequence

<400> SEQUENCE: 91 agggg                                                             5

<210> SEQ ID NO 92
<211> LENGTH: 5
<212> TYPE: DNA
<213> ORGANISM: Artificial Sequence
<220> FEATURE:
<223> OTHER INFORMATION: synthetic sequence

<400> SEQUENCE: 92
``` aaggg                                                                 5

<210> SEQ ID NO 93
<211> LENGTH: 20
<212> TYPE: DNA
<213> ORGANISM: Artificial Sequence
<220> FEATURE:
<223> OTHER INFORMATION: synthetic sequence

<400> SEQUENCE: 93
ctgcccgcaa atcgaccggt                                                20

<210> SEQ ID NO 94
<211> LENGTH: 25
<212> TYPE: DNA
<213> ORGANISM: Artificial Sequence
<220> FEATURE:
<223> OTHER INFORMATION: synthetic sequence

<400> SEQUENCE: 94
ggatacatac aagagagact ttgtc                                          25

<210> SEQ ID NO 95
<211> LENGTH: 20
<212> TYPE: DNA
<213> ORGANISM: Artificial Sequence
<220> FEATURE:
<223> OTHER INFORMATION: synthetic sequence

<400> SEQUENCE: 95
gccgctcgca agagtgcgcc                                                20

<210> SEQ ID NO 96
<211> LENGTH: 19
<212> TYPE: DNA
<213> ORGANISM: Artificial Sequence
<220> FEATURE:
<223> OTHER INFORMATION: synthetic sequence

<400> SEQUENCE: 96
ttcttcaccc ctccagtag                                                 19

<210> SEQ ID NO 97
<211> LENGTH: 14
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (8)..(10)
<223> OTHER INFORMATION: LNA nucleotide

<400> SEQUENCE: 97
cgctcgcatg agtg                                                      14

<210> SEQ ID NO 98
<211> LENGTH: 17
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (5)..(5)
<223> OTHER INFORMATION: LNA nucleotide
<220> FEATURE:
<221> NAME/KEY: misc_feature

```
<222> LOCATION: (8)..(9)
<223> OTHER INFORMATION: LNA nucleotide
<220> FEATURE:
<221> NAME/KEY: misc_feature
<222> LOCATION: (11)..(11)
<223> OTHER INFORMATION: LNA nucleotide

<400> SEQUENCE: 98
tactggaagg gtgaaga                                                    17

<210> SEQ ID NO 99
<211> LENGTH: 14
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5-FAM
<220> FEATURE:
<221> NAME/KEY: misc_feature
<222> LOCATION: (7)..(8)
<223> OTHER INFORMATION: LNA nucleotide
<220> FEATURE:
<221> NAME/KEY: misc_feature
<222> LOCATION: (8)..(9)
<223> OTHER INFORMATION: LNA nucleotide
<220> FEATURE:
<221> NAME/KEY: misc_feature
<222> LOCATION: (9)..(10)
<223> OTHER INFORMATION: LNA nucleotide
<220> FEATURE:
<221> NAME/KEY: misc_feature
<222> LOCATION: (14)..(14)
<223> OTHER INFORMATION: Dab-3

<400> SEQUENCE: 99
cgctcgcatg agtg                                                       14

<210> SEQ ID NO 100
<211> LENGTH: 17
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5-FAM
<220> FEATURE:
<221> NAME/KEY: misc_feature
<222> LOCATION: (4)..(5)
<223> OTHER INFORMATION: LNA nucleotide
<220> FEATURE:
<221> NAME/KEY: misc_feature
<222> LOCATION: (7)..(8)
<223> OTHER INFORMATION: LNA nucleotide
<220> FEATURE:
<221> NAME/KEY: misc_feature
<222> LOCATION: (8)..(9)
<223> OTHER INFORMATION: LNA nucleotide
<220> FEATURE:
<221> NAME/KEY: misc_feature
<222> LOCATION: (10)..(11)
<223> OTHER INFORMATION: LNA nucleotide
<220> FEATURE:
<221> NAME/KEY: misc_feature
<222> LOCATION: (17)..(17)
<223> OTHER INFORMATION: Dab-3

<400> SEQUENCE: 100
tactggaagg gtgaaga                                                    17
```

```
<210> SEQ ID NO 101
<211> LENGTH: 14
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5-MAXN
<220> FEATURE:
<221> NAME/KEY: misc_feature
<222> LOCATION: (7)..(8)
<223> OTHER INFORMATION: LNA nucleotide
<220> FEATURE:
<221> NAME/KEY: misc_feature
<222> LOCATION: (8)..(9)
<223> OTHER INFORMATION: LNA nucleotide
<220> FEATURE:
<221> NAME/KEY: misc_feature
<222> LOCATION: (9)..(10)
<223> OTHER INFORMATION: LNA nucleotide
<220> FEATURE:
<221> NAME/KEY: misc_feature
<222> LOCATION: (14)..(14)
<223> OTHER INFORMATION: Dab-3

<400> SEQUENCE: 101
cgctcgcatg agtg                                                      14

<210> SEQ ID NO 102
<211> LENGTH: 17
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5-MAXN
<220> FEATURE:
<221> NAME/KEY: misc_feature
<222> LOCATION: (7)..(8)
<223> OTHER INFORMATION: LNA nucleotide
<220> FEATURE:
<221> NAME/KEY: misc_feature
<222> LOCATION: (8)..(9)
<223> OTHER INFORMATION: LNA nucleotide
<220> FEATURE:
<221> NAME/KEY: misc_feature
<222> LOCATION: (10)..(11)
<223> OTHER INFORMATION: LNA nucleotide
<220> FEATURE:
<221> NAME/KEY: misc_feature
<222> LOCATION: (17)..(17)
<223> OTHER INFORMATION: Dab-3

<400> SEQUENCE: 102
tactggaagg gtgaaga                                                   17
```

RAPID QUANTITATIVE DETECTION OF SINGLE NUCLEOTIDE POLYMORPHISMS OR SOMATIC VARIANTS AND METHODS TO IDENTIFY MALIGNANT NEOPLASMS

CROSS-REFERENCE TO RELATED APPLICATIONS

This application is a U.S. national stage application, pursuant to 35 U.S.C. § 371, of PCT International Application No.: PCT/US2015/067524, filed Dec. 22, 2015, designating the United States and published in English, which claims priority to U.S. Provisional Application No. 62/095,386, filed Dec. 22, 2014, the contents of which are incorporated herein by reference in their entireties.

STATEMENT REGARDING FEDERALLY SPONSORED RESEARCH

This invention was made with Government support under Grant No. TCGA and Grant No. CA143867 awarded by the National Institutes of Health. The Government has certain rights in this invention.

FIELD

The present disclosure relates to the field of rapid, simultaneous, and quantitative detection of genomic mutations. More specifically, the disclosure relates to the detection of single nucleotide variants in genomic sequences which may have low complexity and/or high GC content, and to the diagnosis, staging and treatment of cancers and conditions associated with the single nucleotide variants.

SEQUENCE LISTING

The instant application contains a Sequence Listing, which has been submitted electronically, in ASCII format and is hereby incorporated by reference in its entirety. Said ASCII copy, created on Dec. 22, 2015, is named "576597_BDC-001PC_sequence_listing.txt" and is 32,768 bytes in size.

BACKGROUND

Recent large-scale genomic analyses have revealed highly recurrent somatic single nucleotide variants (sSNVs) occurring within the majority of the common cancer subtypes. Incorporating molecular-based classifications with conventional tissue-based pathologic diagnosis will continue to guide decision-making for treatment.

For example, in glioma the recurrent somatic R132H mutation in Isocitrate Dehydrogenase 1 (IDH1) is detected in 75% of grade II and III astrocytomas and two separate mutations in the promoter region of Telomerase Reverse Transcriptase (TERT) are detected in 83% of primary glioblastoma (GBM, grade IV astrocytoma) (P. J. Killela et al., *Proc. Natl. Acad. Sci. U.S.A.* 110, 6021-6026 (2013), C. Koelsche et al., *Acta Neuropathol. (Berl.).* 126, 907-915 (2013), N. Nonoguchi et al., *Acta Neuropathol. (Berl.).* 126, 931-937 (2013). Oligodendrogliomas are highly chemotherapy-sensitive gliomas characterized by loss of heterozygosity of chromosome 1p and 19q, but recent studies have found that 80% of these are also defined by concurrent mutations in IDH1 and TERT promoter (P. J. Killela et al., *Proc. Natl. Acad. Sci. U.S.A.* 110, 6021-6026 (2013), N. Sabha et al., *Neuro-Oncol.* (2014), doi:10.1093/neuonc/not299., H. Arita et al., *Acta Neuropathol. (Berl.).* 126, 267-276 (2013)). The classification of glioma by these recurrent mutations in IDH1 and TERT promoter closely mirrors conventional histopathology, but serves as a stronger predictor of response to adjuvant therapy and overall survival than conventional pathology (P. J. Killela et al., *Oncotarget* (2014), A. K.-Y. Chan et al., *Mod. Pathol. Off J. U.S. Can. Acad. Pathol. Inc* (2014), doi:10.1038/modpathol.2014.94). This latter point is critical for appropriate clinical trial design and patient stratification.

World Health Organization (WHO) grade II diffuse gliomas are a group of slow-growing primary central nervous system tumors, including oligodendrogliomas, astrocytomas and oligoastrocytomas. Grade II diffuse gliomas are clinically indolent lesions for which progression free and overall patient survival positively correlates with maximal upfront resection (Smith J S, et al., J Clin Oncol Off J Am Soc Clin Oncol 2008; 26(8):1338-45; Yordanova Y N, et al., J Neurosurg 2011; 115(2):232-9; Jakola A S, et al., JAMA 2012; 308(18):1881-8; Potts M B, et al., J Neurosurg 2012; 116(2):365-72; Beiko J, et al., Neuro-Oncol 2014; 16(1):81-91). The initial surgical procedure can therefore be both diagnostic and therapeutic, but accurate intraoperative diagnosis is essential in determining whether to continue with more aggressive surgical resection. However, as a consequence of the tumor location, infiltrative growth, low cellularity and often small stereotactic biopsy specimens, frozen intraoperative pathological assessment of low-cellularity diffuse gliomas can be challenging (Glantz M J, et al., Neurology 1991; 41(11):1741-4; Jackson R J, Fuller G N, Abi-Said D, et al.; 3(3):193-200; Regragui A, et al., Neurochirurgie 2003; 49(2-3 Pt 1): 67-72). This diagnostic dilemma often requires clarification by final pathologic analysis several days after the diagnostic biopsy, including immunohistochemistry (IHC) for Ki67, TP53, IDH1 R132H or even targeted sequencing. Once the diagnosis is firmly established, patients may then require a second neurosurgical procedure for definitive resection.

Recent studies have demonstrated that diffuse gliomas harbor characteristic recurrent somatic mutations in IDH1 (present in >80% of diffuse astrocytomas, oligodendrogliomas, oligoastrocytomas and secondary glioblastoma (GBM); Yan H, et al., N Engl J Med 2009; 360(8):765-73) and the TERT promoter (similarly present in up to 80% of oligodendrogliomas and primary GBM; Arita H, et al., Acta Neuropathol (Berl) 2013; 126(2):267-76; Killela P J, et al., Proc Natl Acad Sci USA 2013; 110(15):6021-6; Nonoguchi N, et al., Acta Neuropathol (Berl) 2013; 126(6):931-7). An intraoperative assay that could rapidly and accurately identify these recurrent molecular features could augment "frozen section" histopathologic analysis, improve intraoperative diagnosis and accelerate real-time decision-making in the management of grade II diffuse gliomas.

Melanoma is a highly prevalent neoplasm that is also characterized by recurrent missense sSNVs leading to activating mutations in either B-Raf or NRAS (E. Hodis et al., *Cell.* 150, 251-263 (2012)). Benign nevi have also been found to harbor BRAF V600E, which reduces the specificity of the alteration for distinguishing these nevi from malignant pathologies (J. M. Taube, S. Begum, C. Shi, J. R. Eshleman, W. H. Westra, *Am. J. Surg. Pathol.* 33, 568-571 (2009)). However, recent whole genome analyses have revealed that primary melanoma and basal cell cancer are uniquely characterized by recurrent mutations in the promoter region of TERT (F. W. Huang et al., *Science.* 339, 957-959 (2013), S. Horn et al., *Science.* 339, 959-961 (2013), J. Vinagre et al.,

*Nat. Commun.* 4, 2185 (2013)), and, thus, more specifically discriminates true neoplastic pathology from benign lesions.

Somatic single nucleotide variants targeting the Q61 codon of NRAS occurs in 10-25% of cutaneous melanoma (Tsao, H., et al. (2012); Genes Dev., 26:1131-1155). Patients undergoing therapies targeting mutant BRAF have been found to develop resistance through mechanisms that result in mutations to NRAS Q61 codon (Van Allen E, et al. (2014); Can Disc., 4:94). Furthermore, patients with NRAS-mutant melanoma have a better response to immunotherapy than those with mutant BRAF (Johnson, D B, et al. (2015); Cancer Immunol Res., 3(3):288-295) therefore monitoring the blood for evidence of these alterations can have great prognostic value.

Diffuse intrinsic pontine gliomas (DIPG) are diffusely infiltrative malignant glial neoplasms that arise in the brainstem during childhood (Panditharatna E., et al. (2015); Cancer Genet. 208, 367-373). These tumors are highly aggressive and ultimately fatal. Though there is a growing consensus toward obtaining biopsies of patients with suspected DIPG (Walker, D. A. et. al. (2013); Neuro-oncology 4, 462-468), concerns remain regarding the risks of routine brainstem biopsies in children. A large percentage of pediatric high-grade gliomas have recently been found to harbor recurrent mutations in H3F3A, including more than 70% of diffuse intrinsic pontine glioma, one-third of pediatric glioblastoma and nearly 20% of pediatric anaplastic astrocytoma (Schwartzentruber, J. et al. (2012); Nature 482, 226-231, Wu, G. et al. (2012); Nat. Genet. 44, 251-253). Improving the diagnostic success rate for diffuse gliomas while decreasing the risks associated with biopsy of critical brain structures, as in cases of suspected DIPG, could significantly improve the management of diffuse gliomas in adults and children. The detection of genomic alterations that define diffuse gliomas, including DIPGs, from small volumes of Cerebrospinal Fluid (CSF), would allow for minimally invasive diagnosis and monitoring of response to cancer-directed therapies using CSF specimens obtained by lumbar punctures.

Uveal melanomas are malignancies originating within the melanocytes of the eye involving the iris, ciliary body or choroid. Patients with uveal melanoma have an approximately 50% likelihood of developing metastases and of those, the median survival rate is 2 to 15 months (Augsburger J., et al. (2009); Am J. Opthalmol, 148:119-127, and van den Bosch, T., et al. (2010); Dermatol Res Pract, 2010: 360136). In upwards of 80% of uveal melanomas, somatic single nucleotide variants in GNAQ or GNA11 are found to occur and have been shown to lead to the activation of the MAPK pathway (Chen X., et al., (2014); Oncogene, 33:4724-4734, Van Raamsdonk C D, et al (2010); N Engl J Med, 363:2191-2199, Van Raamsdonk C D, et al. (2009); Nature 457:599-602). Inhibition of the MAPK pathway shows promise in leading to improved progression free survival (Carvajal R D, et al. (2014); Jama 311:2397-2405, however predicting response is hindered by the location of the tumor. Improved diagnostic success would be achieved through monitoring the blood of patients with uveal melanoma by the detection of alterations to GNAQ and GNA11.

Timely and accurate diagnosis of cancer subtypes is critical for appropriately stratifying patients for real-time intraoperative decision-making. For instance, a "frozen section" during neurosurgical resection of malignant gliomas can facilitate intraoperative decision-making, however, the concordance between frozen and permanent histopathology has been reported to be ~90% (A. Regragui, et al., *Neurochirurgie.* 49, 67-72 (2003)) due to secondary to small or unrepresentative sample size, low tumor purity and disruption of histologic architecture (M. J. Glantz et al., *Neurology.* 41, 1741-1744 (1991), R. J. Jackson et al., *Neuro-Oncol.* 3, 193-200 (2001), T. P. Plesec, *R. A. Prayson, Arch. Pathol. Lab. Med.* 131, 1532-1540 (2007), B. Y. S. Kim et al., *J. Neurooncol.* (2014), doi:10.1007/s11060-014-1451-0). Molecular based cancer diagnostic assays are also important for clustering patients of similar prognoses for clinical trial design (I. K. Mellinghoff et al., *N. Engl. J. Med.* 353, 2012-2024 (2005)) and can guide targeted therapies in the management of malignant neoplasms.

There is a need for translation of this genomic knowledge to provide sensitive and rapid molecular-based pathologic determinations in a timeframe that can impact surgical decision-making and to facilitate non-invasive monitoring of disease progression and treatment response.

SUMMARY

Here, we report the development of compositions and methods that detect cancer-specific mutations in specimens. In some aspects, the specimens are cancer patient biopsies with low tumor density, e.g., infiltrating gliomas. In some aspects the single nucleotide variant is a somatic alteration in a chromosomal sequence compared to wild type. In some aspects, the somatic nucleotide alteration is associated with a cancerous alteration in a cell. In some aspects, the somatic nucleotide alteration is present in at least one cell in a tumor sample. In some aspects, the somatic nucleotide alteration is present in only a subset of cancer cells in a tumor sample. In some aspects, the disclosed aspects are distinguished from current less sensitive techniques for detecting low abundance sequences in a complex mixture by including the following features: (1) optimization to overcome the low complexity and high GC content of a target site, (2) inclusion of modified oligonucleotides with peptide nucleic acid (PNA) backbones to block logarithmic amplification of wild-type alleles, (3) incorporation of locked nucleic acids (LNA) into mutant allele detection probes to increase specificity, and (4) designed so that multiple assays can be used to profile multiple genes at the same time under the same cycling parameters. In some aspects, the target site comprising low sequence complexity and/or high GC content is at least one region of the TERT promoter. In one aspect, the disclosed aspects provide a quantitative polymerase chain reaction (qPCR) based assay, able to perform rapid amplification-based genotyping of cells from a subject. In one aspect, the genotyping comprises determination of the presence or absence of at least one somatic alteration in a target sequence in at least one cell from a patient sample. In one aspect, the somatic gene alteration is present in the IDH1 coding region. In one aspect, the somatic gene alteration is present in the TERT promoter. In one aspect, somatic gene alterations are present in both the IDH1 coding region and TERT promoter. In one aspect, the somatic gene alterations comprise recurrent mutations. In one aspect, the methods provided herein are used to identify these recurrent mutations within 45 minutes of obtaining a biopsy specimen, a time frame that parallels frozen section analysis. In one aspect, the methods provided herein have a sensitivity of 0.1% allelic fraction of tumor sSNVs ("single nucleotide variants") in a complex mixture comprising wild type and mutant sequences in a target site. In one aspect, the sSNVs comprise one or more somatic gene alterations in one or both of a TERT promoter and an IDH1 coding region. In one aspect, the presence or absence of one or more specific sSNVs predicts final pathology in 90% of archived gliomas.

As disclosed herein, the described techniques optionally provide means of intraoperative molecular characterization, whereby the methods could supplement, replace or assist pathologic analysis of low cellularity diffuse gliomas, distinguishing them from non-neoplastic processes by providing cancer-specific genomic information, and could help both accelerate and solidify the decision to pursue resection within the time frame of the current operative procedure, thus eliminating the potential risks and costs associated with re-operation, and ultimately improving the approach to patients with diffuse gliomas. The methods provided herein could be used for real-time intraoperative diagnosis. In some embodiments, the intraoperative diagnosis can be used to confirm a diagnosis. In another embodiment, intraoperative diagnosis allows for intraoperative therapy. In yet another embodiment, the intraoperative therapy may comprise resection, thermal ablation therapy, laser microsurgery, or targeted therapy at the time of operation.

Given the sensitivity of these methods, the disclosed platform can be extended to detect mutant TERT promoter alleles in blood of patients with progressive disease. In one aspect the mutant TERT promoter allele is in the cell-free component of a patient blood sample. In one aspect the mutant TERT promoter allele is in a circulating cancer cell obtained from a patient blood sample. In one aspect, the sensitive and specific molecular diagnostic techniques described herein could significantly aid the discrimination of tumor pathology at the time of diagnosis, and could furthermore be useful for non-invasively monitoring of disease progression. In addition, the ability to sensitively detect tumor alleles in the blood by this rapid method opens a new avenue for non-invasively monitoring tumor progression and treatment response. This would be especially useful for cancers, like melanoma, that have longer lengths of time for progression from localized to systemic disease, which is often noted when the patient has a symptomatic metastasis, and for gliomas that would otherwise require at least an initial intraoperative procedure in order to obtain a biopsy.

In one aspect, a system is provided for detection or amplification of one or more single nucleotide polymorphisms or somatic nucleotide variants in one or more target nucleic acids that may have high GC content and/or low sequence complexity in a sample. In one aspect, the system includes a forward primer that hybridizes to a first region on a sense strand of the target nucleic acid, a reverse primer that hybridizes to a second region on an antisense strand of the target nucleic acid, a locked nucleic acid (LNA) probe comprising an oligonucleotide with at least one LNA modification on at least one nucleotide, wherein the probe comprises a nucleic acid sequence that is complementary to a mutant allele sequence of the target nucleic acid and located within the region amplified by the forward primer and the reverse primer, a peptide nucleic acid (PNA) blocker that hybridizes to a wild-type allele of the target nucleic acid, the PNA blocker comprising an oligonucleotide comprising one or more peptide nucleic acids that acts to block (i.e., inhibit or cause a relative decrease in) amplification of the wild-type allele, and does not block amplification of the mutant allele, wherein the PNA blocker hybridizes to a region of the wild-type allele located within the region amplified by the forward and reverse primer, and a reaction buffer, wherein the forward primer, the reverse primer, the LNA probe, and the PNA blocker are capable of recognizing their target sequences under same temperature conditions.

In one aspect, a kit is provided that includes components that compose the system of the disclosed invention herein. In one aspect, the kit comprises the forward primer, reverse primer, LNA probe and PNA blocker for at least one target sequence. In one aspect, the target sequence is a region of the telomerase reverse transcriptase (TERT) promoter. In one aspect, the TERT promoter comprises one or both somatic variants C228T and C250T, as further described herein. In one aspect, the LNA probe hybridizes to a nucleotide region comprising a T at position 228 of the mutated allele of the TERT promoter and the PNA blocker hybridizes to a nucleotide region comprising a C at the corresponding position in a wild type allele.

In one aspect, the LNA probe hybridizes to a nucleotide region comprising a T at position 250 of the mutated allele of the isocitrate dehydrogenase 1 (IDH1) coding region and the PNA blocker hybridizes to a nucleotide region comprising a C at the corresponding position in a wild type allele. In one aspect, the target sequence is a region of the IDH1 gene. In one aspect, the IDH1 gene region comprises the nucleotide sequence encoding a somatic mutation at position 132 of the polypeptide. In one aspect, the LNA probe hybridizes to a nucleotide region comprising a mutated codon encoding an amino acid selected from one or more of a histidine ("H"), cysteine ("C"), glycine ("G"), serine ("S") and leucine ("L") at position 132 of the mutated IDH1 protein, and the PNA blocker hybridizes to a nucleotide region comprising a wild type codon encoding an arginine ("R") at the corresponding position in a wild type allele.

In some embodiments, the LNA probe hybridizes to a nucleotide region comprising an A of the mutated allele of the proto-oncogene B-raf (BRAF) coding region and the PNA blocker hybridizes to a nucleotide region comprising a T at the corresponding position in a wild type allele. In another embodiment, the target sequence is a region of the BRAF gene. In certain embodiments, the LNA probe hybridizes to a nucleotide region comprising a mutated codon encoding a glutamic acid ("E") at position 600 of the mutated BRAF protein, and the PNA blocker hybridizes to a nucleotide region comprising a wild type codon encoding a valine ("V") at the corresponding position in a wild type allele.

In yet another embodiment, the LNA probe hybridizes to a nucleotide region comprising a G of the mutated allele of the neuroblastomas RAS viral oncogene homolog (NRAS) coding region and the PNA blocker hybridizes to a nucleotide region comprising an A at the corresponding position in a wild type allele. In still another embodiment, the LNA probe hybridizes to a nucleotide region comprising an A of the mutated allele of the neuroblastomas RAS viral oncogene homolog (NRAS) coding region and the PNA blocker hybridizes to a nucleotide region comprising a C at the corresponding position in a wild type allele. In certain embodiments, the target sequence is a region of the NRAS gene. In still another embodiment, the LNA probe hybridizes to a nucleotide region comprising a mutated codon encoding an amino acid selected from one or more of an arginine ("R") and a lysine ("K") at position 61 of the mutated allele of the NRAS and the PNA blocker hybridizes to a nucleotide region comprising a wild type codon encoding a glutamine ("Q") at the corresponding position in a wild type allele.

In a further embodiment, the LNA probe hybridizes to a nucleotide region comprising a A of the mutated allele of the a guanine nucleotide-binding protein G(q) subunit α (GNAQ) coding region and the PNA blocker hybridizes to a nucleotide region comprising a G at the corresponding position in a wild type allele. In another embodiment, the LNA probe hybridizes to a nucleotide region comprising a T of the mutated allele of the a guanine nucleotide-binding protein G(q) subunit a (GNAQ) coding region and the PNA blocker hybridizes to a nucleotide region comprising a A at the corresponding position in a wild type allele. In yet another embodiment, the LNA probe hybridizes to a nucleotide region comprising a C of the mutated allele of the a guanine nucleotide-binding protein G(q) subunit α (GNAQ) coding region and the PNA blocker hybridizes to a nucleotide region comprising an A at the corresponding position in a wild type allele. In certain embodiments, the target sequence is a region of the GNAQ gene.

In another embodiment, the LNA probe hybridizes to a nucleotide region comprising a mutated codon encoding a glutamine ("Q") at position 183 of the mutated allele of the GNAQ, and the PNA blocker hybridizes to a nucleotide region comprising a wild type codon encoding an arginine ("R") at position 183 in a wild type allele. In another embodiment, the LNA probe hybridizes to a nucleotide region comprising a mutated codon encoding a leucine ("L") or a proline ("P") at position 209 of the mutated allele of the GNAQ, and the PNA blocker hybridizes to a nucleotide region comprising a wild type codon encoding a glutamine ("Q") at position 209 in a wild type allele.

In another embodiment, the LNA probe hybridizes to a nucleotide region comprising a T of the mutated allele of the guanine nucleotide-binding protein subunit α-11 (GNA11) coding region and the PNA blocker hybridizes to a nucleotide region comprising an A at the corresponding position in a wild type allele. In some embodiments, the target sequence is a region of the GNA11 gene. In another embodiment, the LNA probe hybridizes to a nucleotide region comprising a mutated codon encoding an amino acid selected from one or more of a leucine ("L") at position 209 of the mutated allele of the GNA11 and the PNA blocker hybridizes to a nucleotide region comprising a wild type codon encoding a glutamine ("Q") at the corresponding position in a wild type allele.

In still another embodiment, the LNA probe hybridizes to a nucleotide region comprising a T of the mutated allele of the H3 histone, family 3A (H3F3A) coding region and the PNA blocker hybridizes to a nucleotide region comprising a A at the corresponding position in a wild type allele. In still another embodiment, the LNA probe hybridizes to a nucleotide region comprising an A of the mutated allele of the H3 histone, family 3A (H3F3A) coding region and the PNA blocker hybridizes to a nucleotide region comprising a G at the corresponding position in a wild type allele. In certain embodiments, the target sequence is a region of the H3F3A gene. In another embodiment, the LNA probe hybridizes to a nucleotide region comprising a mutated codon encoding a methionine ("M") at position 27 of the mutated allele of the H3F3A and the PNA blocker hybridizes to a nucleotide region comprising a wild type codon encoding a lysine ("K") at position 27 in a wild type allele. In another embodiment, the LNA probe hybridizes to a nucleotide region comprising a mutated codon encoding an arginine ("R") at position 34 of the mutated allele of the H3F3A and the PNA blocker hybridizes to a nucleotide region comprising a wild type codon encoding a glycine ("G") at position 34 in a wild type allele.

In one aspect, a method is provided of using the system to detect or amplify one or more single nucleotide polymorphisms or somatic variants in at least one target nucleic acid including but not limited to, e.g., a target sequence with low sequence complexity and/or high GC content, in a sample from a subject, where the method includes isolating DNA from the sample; denaturing the isolated DNA; annealing the forward primer, the reverse primer, the LNA probe, and the PNA blocker to the DNA at the same temperature conditions; and amplifying and detecting a DNA amplicon comprising the one or more single nucleotide polymorphisms, thereby detecting or amplifying one or more single nucleotide polymorphisms.

In one aspect, a method is provided for establishing a molecular diagnosis in at least one cancer in a subject, where the method includes isolating DNA from a sample from the subject; denaturing the DNA isolated from the sample and a control DNA template; annealing a forward primer that hybridizes to a first region on a sense strand of a first target nucleic acid, a reverse primer that hybridizes to a second region on an antisense strand of the first target nucleic acid, a locked nucleic acid (LNA) probe comprising an oligonucleotide with at least one LNA modification on at least one nucleotide, wherein the probe comprises a nucleic acid sequence that is complementary to a mutant allele of the first target nucleic acid, and a peptide nucleic acid (PNA) blocker comprising an oligonucleotide comprising one or more peptide nucleic acids that acts to block (i.e., inhibit or cause a relative decrease in) amplification of a wild-type allele of the first target nucleic acid, and does not block amplification of a mutant allele of the first target nucleic acid, wherein the PNA blocker hybridizes to a region of the wild-type allele located within a region amplified by the forward and reverse primer; amplifying a DNA amplicon comprising the mutant allele in the first target nucleic acid; detecting the mutant allele in the first target nucleic acid in the sample; and quantifying the amount of the mutant allele in the first target nucleic acid in the sample relative to the amount in a control, wherein a higher prevalence of the amount of the mutant allele in the sample relative to the control indicates presence and/or stage of the cancer in the subject.

In one aspect of the disclosure, the assay is an intraoperative single nucleotide variant detection assay wherein the assay is performed and results are obtained concurrent with a surgical procedure for obtaining the sample from a patient.

In one aspect, a method is provided for diagnosis of melanoma in a subject, where the method includes isolating DNA from a sample acquired from a patient, e.g., such as a skin biopsy or a metastatic lesion; denaturing the DNA isolated from the sample and a control DNA template; annealing a forward primer that hybridizes to a first region on a sense strand of a first target nucleic acid, a reverse primer that hybridizes to a second region on an antisense strand of the first target nucleic acid, a locked nucleic acid (LNA) probe comprising an oligonucleotide with at least one LNA modification on at least one nucleotide, wherein the probe comprises a nucleic acid sequence that is complementary to a mutant allele sequence of the first target nucleic acid, and a peptide nucleic acid (PNA) blocker comprising an oligonucleotide comprising one or more peptide nucleic acids that acts to block (i.e., inhibit or cause a relative decrease in) the amplification of a wild-type allele of the first target nucleic acid, and does not block amplification of a mutant allele of the first target nucleic acid, wherein the PNA blocker hybridizes to a region of the wild-type allele located within a region amplified by the forward and reverse primer; amplifying a DNA amplicon comprising the mutant allele in the first target nucleic acid; and detecting the amount of the mutant allele present from the first target nucleic acid in the sample, wherein increased prevalence of the mutant allele the first target nucleic acid in the sample relative to the control indicates presence of a melanoma in the subject.

In some embodiments, the target nucleic acid has low sequence complexity. In some embodiments, the target nucleic acid has high GC content. In some embodiments, the target nucleic acid has a GC content of greater than 60%.

In some embodiments, the mutant allele comprises a single nucleotide polymorphism. In some embodiments, the mutant allele comprises a somatic variant. In some embodiments, the mutant allele comprises at least one single nucleotide polymorphism or somatic variant.

In some embodiments, the LNA probe comprises a first end and a second end, wherein the first end comprises a label and wherein the second end comprises a quencher.

In some embodiments, the target nucleic acid comprises a portion of the nucleic acid sequence of a telomerase reverse transcriptase (TERT) gene. In some embodiments, the TERT gene comprises a portion of the nucleic acid sequence of the regulatory region of the TERT gene promoter. In some embodiments, the mutant allele comprises variant C228T (hg19, chromosome 5:1,295,228) of the TERT gene promoter. In some embodiments, the mutant allele comprises variant C250T (hg19, chromosome 5:1,295,250) of the TERT gene promoter. In some embodiments, the mutant allele comprises a variant comprising the sequence CCTTC (SEQ ID NO: 1) at about nucleotide positions 1,295,226-1,295,230 of human chromosome 5, as compared to the wild-type allele at the corresponding positions comprising the sequence CCCTC (SEQ ID NO: 2). In some embodiments, the mutant allele comprises a variant comprising the sequence CCCAGCCCCTTCCGGGCCC (SEQ ID NO: 3), as compared to the wild-type allele comprising the sequence CCCAGCCCCCTCCGGGCCC (SEQ ID NO: 4). In some embodiments, the mutant allele comprises a variant comprising T, or Thymine, at about nucleotide position 1,295,228 of human chromosome 5, as compared to the wild-type allele at the corresponding position comprising C, or Cytosine. In some embodiments, the mutant allele comprises a variant comprising the sequence CTTCC (SEQ ID NO: 5) at about nucleotide positions 1,295,248-1,295,252 of human chromosome 5, as compared to the wild-type allele at the corresponding positions comprising the sequence CTCCC (SEQ ID NO: 6). In some embodiments, the mutant allele comprises a variant comprising the sequence CCGACCCCT TCCGGGTCCC (SEQ ID NO: 7), as compared to the wild-type allele comprising the sequence CCGACCCCT CCCGGGTCCC (SEQ ID NO: 8). In some embodiments, the mutant allele comprises a variant comprising T, or Thymine, at about nucleotide position 1,295,250 of human chromosome 5, as compared to the wild-type allele at the corresponding position comprising C, or Cytosine.

In some embodiments, the forward primer comprises the nucleic acid sequence of 5'-CACGTGCGCAGCAG-GACGCAG-3' (SEQ ID NO: 9). In some embodiments, the reverse primer comprises the nucleic acid sequence of 5'-CTTCACCTTCCAGCTCCGCCTC-3' (SEQ ID NO: 10). In some embodiments, the PNA blocker comprises the nucleic acid sequence of 5'-CCCAGCCCCCTC-CGGGCCC-3' (SEQ ID NO: 11). In some embodiments, the PNA blocker comprises the nucleic acid sequence of 5'-CCGACCCCTCCCGGGTCCC-3' (SEQ ID NO: 12).

In some embodiments, the LNA probe comprises the nucleic acid sequence of 5'-CCCAGCCCC+T+TC-CGGGCCC-3' (SEQ ID NO: 13), wherein nucleotides preceded by a "+" are LNA modified nucleotides.

In some embodiments, the LNA probe comprises the nucleic acid sequence of 5'-CCGACCCC+T+TC-CGGGTCCC-3' (SEQ ID NO: 14), wherein nucleotides preceded by a "+" are LNA modified nucleotides.

In some embodiments, the LNA probe comprises the nucleic acid sequence of 5'-FAM-CCCAGCCCC+T+TC-CGGGCCC-Dab-3'(SEQ ID NO: 15), wherein nucleotides preceded by a "+" are LNA modified nucleotides, FAM is fluorescein moiety, and Dab is diaminobenzidine.

In some embodiments, the LNA probe comprises the nucleic acid sequence of 5'-FAM-CCGACCCC+T+TC-CGGGTCCC-Dab-3'(SEQ ID NO: 16), wherein nucleotides preceded by a "+" are LNA modified nucleotides, FAM is fluorescein moiety, and Dab is diaminobenzidine.

In some embodiments, the target nucleic acid comprises a portion of the nucleic sequence of an isocitrate dehydrogenase 1 (IDH1) gene. In some embodiments, the mutant allele comprises a variant that encodes an IDH1 protein of variant R132H. In some embodiments, the mutant allele comprises the variant described as COSM28746 in the Catalogue of Somatic Mutations In Cancer (COSMIC) of the Wellcome Trust Sanger Institute; see, Forbes et al., 2014, Nucl. Acids Res., doi: 10.1093/nar/gku1075. In some embodiments, the mutant allele comprises a variant comprising the sequence GTCAT (SEQ ID NO: 17) at about nucleotide positions 392-396 from the start of the cDNA, as compared to the wild-type allele at the corresponding positions comprising the sequence GTCGT (SEQ ID NO: 18). In some embodiments, the mutant allele comprises a variant comprising the sequence AGGTCATCATGC (SEQ ID NO: 19), as compared to the wild-type allele comprising the sequence AGGTCGTCATGC (SEQ ID NO: 20). In some embodiments, the mutant allele comprises a variant comprising A, or Adenine, at about nucleotide position 395 from the start of the cDNA, as compared to the wild-type allele at the corresponding position comprising G, or Guanine.

In some embodiments, the mutant allele comprises a variant that encodes an IDH1 protein of variant R132C. In some embodiments, the mutant allele comprises the variant described as COSM28747 in COSMIC. In some embodiments, the mutant allele comprises a variant comprising the sequence GTTGT (SEQ ID NO: 21) at about nucleotide positions 392-396 from the start of the cDNA, as compared to the wild-type allele at the corresponding positions comprising the sequence GTCGT (SEQ ID NO: 18). In some embodiments, the mutant allele comprises a variant comprising the sequence AGGTTGTCATGC (SEQ ID NO: 22), as compared to the wild-type allele comprising the sequence AGGTCGTCATGC (SEQ ID NO: 20). In some embodiments, the mutant allele comprises a variant comprising T, or Thymine, at about nucleotide position 394 from the start of the cDNA, as compared to the wild-type allele at the corresponding position comprising C, or Cytosine.

In some embodiments, the mutant allele comprises a variant that encodes an IDH1 protein of variant R132G. In some embodiments, the mutant allele comprises the variant described as COSM28749 in COSMIC. In some embodiments, the mutant allele comprises a variant comprising the sequence GTGGT (SEQ ID NO: 23) at about nucleotide positions 392-396 from the start of the cDNA, as compared to the wild-type allele at the corresponding positions comprising the sequence GTCGT (SEQ ID NO: 18). In some embodiments, the mutant allele comprises a variant comprising the sequence AGGTGGTCATGC (SEQ ID NO: 24), as compared to the wild-type allele comprising the sequence AGGTCGTCATGC (SEQ ID NO: 20). In some embodiments, the mutant allele comprises a variant comprising G, or Guanine, at about nucleotide position 394 from the start of the cDNA, as compared to the wild-type allele at the corresponding position comprising C, or Cytosine.

In some embodiments, the mutant allele comprises a variant that encodes an IDH1 protein of variant R132S. In some embodiments, the mutant allele comprises the variant described as COSM28748 in COSMIC. In some embodiments, the mutant allele comprises a variant comprising the sequence GTAGT (SEQ ID NO: 25) at about nucleotide positions 392-396 from the start of the cDNA, as compared to the wild-type allele at the corresponding positions comprising the sequence GTCGT (SEQ ID NO: 18). In some embodiments, the mutant allele comprises a variant comprising the sequence AGGTAGTCATGC (SEQ ID NO: 26), as compared to the wild-type allele comprising the sequence AGGTCGTCATGC (SEQ ID NO: 20). In some embodiments, the mutant allele comprises a variant comprising A, or Adenine, at about nucleotide position 394 from the start of the cDNA, as compared to the wild-type allele at the corresponding position comprising C, or Cytosine.

In some embodiments, the mutant allele comprises a variant that encodes an IDH1 protein of variant R132L. In some embodiments, the mutant allele comprises the variant described as COSM28750 in COSMIC. In some embodiments, the mutant allele comprises a variant comprising the sequence GTCTT (SEQ ID NO: 27) at about nucleotide positions 392-396 from the start of the cDNA, as compared to the wild-type allele at the corresponding positions comprising the sequence GTCGT (SEQ ID NO: 18). In some embodiments, the mutant allele comprises a variant comprising the sequence AGGTCTTCATGC (SEQ ID NO: 28), as compared to the wild-type allele comprising the sequence AGGTCGTCATGC (SEQ ID NO: 20). In some embodiments, the mutant allele comprises a variant comprising T, or Thymine, at about nucleotide position 395 from the start of the cDNA, as compared to the wild-type allele at the corresponding position comprising G, or Guanine.

In some embodiments, the forward primer comprises the nucleic acid sequence of 5'-CCGGCTTGTGAGTGGATGGGTAAAACCT-3' (SEQ ID NO: 29). In some embodiments, the reverse primer comprises the nucleic acid sequence of 5'-CATTATTGCCAACATGACTTACTTGATCCCC-3' (SEQ ID NO: 30). In some embodiments, the PNA blocker comprises the nucleic acid sequence of 5'-AGGTCGTCATGC-3' (SEQ ID NO: 20).

In some embodiments, the LNA probe comprises the nucleic acid sequence of 5'-AGG+T+C+A+T+CAT+GC-3' (SEQ ID NO: 31), wherein nucleotides preceded by a "+" are LNA modified nucleotides.

In some embodiments, the LNA probe comprises the nucleic acid sequence of 5'-AGG+T+T+G+T+C+ATGC-3' (SEQ ID NO: 32), wherein nucleotides preceded by a "+" are LNA modified nucleotides.

In some embodiments, the LNA probe comprises the nucleic acid sequence of 5'-AGGT+G+G+T+CAT+GC-3' (SEQ ID NO: 33), wherein nucleotides preceded by a "+" are LNA modified nucleotides.

In some embodiments, the LNA probe comprises the nucleic acid sequence of 5'-AGGT+A+G+T+CA+T+GC-3' (SEQ ID NO: 34) wherein nucleotides preceded by a "+" are LNA modified nucleotides.

In some embodiments, the LNA probe comprises the nucleic acid sequence of 5'-AGG+T+C+T+T+CAT+GC-3' (SEQ ID NO: 35) wherein nucleotides preceded by a "+" are LNA modified nucleotides.

In some embodiments, the LNA probe comprises the nucleic acid sequence of 5'-FAM-AGG+T+C+A+T+CAT+GC-Dab-3' (SEQ ID NO: 36), wherein nucleotides preceded by a "+" are LNA modified nucleotides, FAM is fluorescein moiety, and Dab is diaminobenzidine.

In some embodiments, the LNA probe comprises the nucleic acid sequence of 5'-MAXN-AGG+T+T+G+T+C+ATGC-Dab-3' (SEQ ID NO: 37), wherein nucleotides preceded by a "+" are LNA modified nucleotides, MAXN is fluorescent moiety, and Dab is diaminobenzidine.

In some embodiments, the LNA probe comprises the nucleic acid sequence of 5'-MAXN-AGGT+G+G+T+CAT+GC-Dab-3' (SEQ ID NO: 38), wherein nucleotides preceded by a "+" are LNA modified nucleotides, MAXN is fluorescent moiety, and Dab is diaminobenzidine.

In some embodiments, the LNA probe comprises the nucleic acid sequence of 5'-MAXN-AGGT+A+G+T+CA+T+GC-Dab-3' (SEQ ID NO: 39), wherein nucleotides preceded by a "+" are LNA modified nucleotides, MAXN is fluorescent moiety, and Dab is diaminobenzidine.

In some embodiments, the LNA probe comprises the nucleic acid sequence of 5'-MAXN-AGG+T+C+T+T+CAT+GC-Dab-3' (SEQ ID NO: 40) wherein nucleotides preceded by a "+" are LNA modified nucleotides, MAXN is fluorescent moiety, and Dab is diaminobenzidine In some embodiments, the mutant allele comprises a variant that encodes a BRAF protein of variant V600E. In another embodiment, the mutant allele comprises the variant described as COSM1131 in COSMIC. In yet another embodiment, the wild-type allele comprises the sequence TCACT (SEQ ID NO: 41), as compared to the mutant allele at the corresponding positions comprising a variant comprising the sequence TCTCT (SEQ ID NO: 42). In still another embodiment, the wild-type allele comprises A, or Adenine, as compared to the mutant allele comprising a variant comprising T, or Thymine.

In some embodiments, the forward primer comprises the nucleic acid sequence of 5'-ACAGGGCATGGA-GAGTGGGTC-3' (SEQ ID NO: 43). In another embodiment, the reverse primer comprises the nucleic acid sequence of 5'-CAAACTGATGGGACCCACTCCAT-3' (SEQ ID NO: 44). In yet another embodiment, the PNA blocker comprises the nucleic acid sequence of 5'-CATC-GAGATTTCACTGTAGCTAGA-3' (SEQ ID NO: 45).

In still another embodiment, the LNA probe comprises the nucleic acid sequence of 5'-AGA+TT+T+C+T+CT+GT+AG+C-3' (SEQ ID NO: 46), wherein nucleotides preceded by a "+" are LNA modified nucleotides.

In some embodiments, the LNA probe comprises the nucleic acid sequence of 5'-FAM-AGA+TT+T+C+T+CT+GT+AG+C-Dab-3' (SEQ ID NO: 47), wherein nucleotides preceded by a "+" are LNA modified nucleotides, FAM is fluorescein moiety, and Dab is diaminobenzidine.

In some embodiments, the LNA probe comprises the nucleic acid sequence of 5'-MAXN-AGA+TT+T+C+T+CT+GT+AG+C-Dab-3' (SEQ ID NO: 48), wherein nucleotides preceded by a "+" are LNA modified nucleotides, MAXN is fluorescent moiety, and Dab is diaminobenzidine.

In some embodiments, the mutant allele comprises a variant that encodes an NRAS protein of variant Q61R. In another embodiment, the mutant allele comprises the variant described as COSM584 in COSMIC. In yet another embodiment, the wild-type allele comprises the sequence ACAAG (SEQ ID NO: 49) as compared to the mutant allele at the corresponding positions comprising a variant comprising the sequence ACGAG (SEQ ID NO: 50). In still another embodiment, the wild-type allele comprises G, or Guanine, as compared to the mutant allele comprising a variant comprising A, or Adenine.

In some embodiments, the mutant allele comprises a variant that encodes an NRAS protein of variant Q61K. In another embodiment, the mutant allele comprises the variant described as COSM580 in COSMIC. In yet another embodiment, the wild-type allele comprises the sequence ACAAG (SEQ ID NO: 49) as compared to the mutant allele at the corresponding positions comprising a variant comprising the sequence AAAAG (SEQ ID NO: 51). In still another embodiment, the wild-type allele comprises C, or Cytosine, as compared to the mutant allele comprising a variant comprising A, or Adenine.

In some embodiments, the forward primer comprises the nucleic acid sequence of 5'-AGTGGTTATAGATGGT-GAAACCTG-3' (SEQ ID NO: 52). In another embodiment, the reverse primer comprises the nucleic acid sequence of 5'-ACAGAGGAAGCCTTCGCCTG-3' (SEQ ID NO: 53). In yet another embodiment, the PNA blocker comprises the nucleic acid sequence of 5'-CAGCTGGACAAGAAGAG-TAC-KK-3' (SEQ ID NO: 54).

In still another embodiment, the LNA probe comprises the nucleic acid sequence of 5'-CTGG+AC+G+AG+AA+ GAGTA-3' (SEQ ID NO: 55), wherein nucleotides preceded by a "+" are LNA modified nucleotides.

In some embodiments, the LNA probe comprises the nucleic acid sequence of 5'-CAG+CTGGA+A+A+AGAA+ GA+GTA-3' (SEQ ID NO: 56), wherein nucleotides preceded by a "+" are LNA modified nucleotides.

In another embodiment, the LNA probe comprises the nucleic acid sequence of 5'-FAM-CTGG+AC+G+AG+AA+ GAGTA-Dab-3' (SEQ ID NO: 57), wherein nucleotides preceded by a "+" are LNA modified nucleotides, FAM is fluorescein moiety, and Dab is diaminobenzidine.

In still another embodiment, the LNA probe comprises the nucleic acid sequence of 5'-FAM-CAG+CTGGA+A+A+ AGAA+GA+GTA-Dab-3' (SEQ ID NO: 58), wherein nucleotides preceded by a "+" are LNA modified nucleotides, FAM is fluorescein moiety, and Dab is diaminobenzidine.

In a further embodiment, the LNA probe comprises the nucleic acid sequence of 5'-MAXN-CTGG+AC+G+AG+ AA+GAGTA-Dab-3' (SEQ ID NO: 59), wherein nucleotides preceded by a "+" are LNA modified nucleotides, MAXN is fluorescent moiety, and Dab is diaminobenzidine.

In some embodiments, the LNA probe comprises the nucleic acid sequence of 5'-MAXN-CAG+CTGGA+A+A+ AGAA+GA+GTA-Dab-3' (SEQ ID NO: 60), wherein nucleotides preceded by a "+" are LNA modified nucleotides, MAXN is fluorescent moiety, and Dab is diaminobenzidine.

In some embodiments, the mutant allele comprises a variant that encodes a GNAQ protein of variant R183Q. In another embodiment, the mutant allele comprises the variant described as COSM52975 in COSMIC. In yet another embodiment, the wild-type allele comprises the sequence TCGAG (SEQ ID NO: 61), as compared to the mutant allele at the corresponding positions comprising a variant comprising the sequence TCAAG (SEQ ID NO: 62). In still another embodiment, the wild-type allele comprises G, or Guanine, as compared to the mutant allele comprising a variant comprising A, or Adenine.

In some embodiments, the mutant allele comprises a variant that encodes a GNAQ protein of variant Q209L. In another embodiment, the mutant allele comprises the variant described as COSM33719 in COSMIC. In yet another embodiment, the wild-type allele comprises the sequence CCAAA (SEQ ID NO: 63), as compared to the mutant allele at the corresponding positions comprising a variant comprising the sequence CCTAA (SEQ ID NO: 64). In still another embodiment, the wild-type allele comprises A, or Adenine, as compared to the mutant allele comprising a variant comprising T, or Thymine.

In some embodiments, the mutant allele comprises a variant that encodes a GNAQ protein of variant Q209P. In another embodiment, the mutant allele comprises the variant described as COSM33718 in COSMIC. In yet another embodiment, the wild-type allele comprises the sequence CCAAA (SEQ ID NO: 63), as compared to the mutant allele at the corresponding positions comprising a variant comprising the sequence CCCAA (SEQ ID NO: 65). In still another embodiment, the wild-type allele comprises A, or Adenine, as compared to the mutant allele comprising a variant comprising C, or Cytosine.

In some embodiments, the forward primer comprises the nucleic acid sequence of 5'-TTGGACCGCGTAGCTGAC-CCT-3' (SEQ ID NO: 66). In other embodiments, the forward primer comprises the nucleic acid sequence of 5'-CCCTAAGTTTGTAAGTAGTGCTATA-3' (SEQ ID NO:67). In another embodiment, the reverse primer comprises the nucleic acid sequence of 5'-GCTGGGAAATAG-GTTTCATGGAC-3' (SEQ ID NO: 68). In still another embodiment, the reverse primer comprises the nucleic acid sequence of 5'-TCACTAAGCGCTACTAGAAACATG-3' (SEQ ID NO: 69). In yet another embodiment, the PNA blocker comprises the nucleic acid sequence of 5'-TTA-GAGTTCGAGTCCCCA-3' (SEQ ID NO: 70). In yet another embodiment, the PNA blocker comprises the nucleic acid sequence of 5'-GGGGCCAAAGGTCAGAGA-3' (SEQ ID NO: 71).

In another embodiment, the LNA probe comprises the nucleic acid sequence of 5'-AGAGT+TC+A+AGT+ CCCCAC-3' (SEQ ID NO: 72), wherein nucleotides preceded by a "+" are LNA modified nucleotides.

In some embodiments, the LNA probe comprises the nucleic acid sequence of 5'-AGGGGCC+T+AAGGTCA-GAG-3' (SEQ ID NO: 73), wherein nucleotides preceded by a "+" are LNA modified nucleotides.

In certain embodiments, the LNA probe comprises the nucleic acid sequence of 5'-GGGCC+C+AAGGTCA-GAGA-3' (SEQ ID NO: 74), wherein nucleotides preceded by a "+" are LNA modified nucleotides.

In still another embodiment, the LNA probe comprises the nucleic acid sequence of 5'-FAM-AGAGT+TC+A+AGT+ CCCCAC-Dab-3' (SEQ ID NO: 75), wherein nucleotides preceded by a "+" are LNA modified nucleotides, FAM is fluorescein moiety, and Dab is diaminobenzidine.

In another embodiment, the LNA probe comprises the nucleic acid sequence of 5'-FAM-AGGGGCC+T+ AAGGTCAGAG-Dab-3' (SEQ ID NO: 76), wherein nucleotides preceded by a "+" are LNA modified nucleotides, FAM is fluorescein moiety, and Dab is diaminobenzidine.

In other embodiments, the LNA probe comprises the nucleic acid sequence of 5'-FAM-GGGCC+C+AAGGTCA-GAGA-Dab-3' (SEQ ID NO: 77), wherein nucleotides preceded by a "+" are LNA modified nucleotides, FAM is fluorescein moiety, and Dab is diaminobenzidine.

In yet another embodiment, the LNA probe comprises the nucleic acid sequence of 5% MAXN-AGAGT+TC+A+ AGT+CCCCAC-Dab-3' (SEQ ID NO: 78), wherein nucleotides preceded by a "+" are LNA modified nucleotides, MAXN is fluorescent moiety, and Dab is diaminobenzidine.

In another embodiment, the LNA probe comprises the nucleic acid sequence of 5'-MAXN-AGGGGCC+T+ AAGGTCAGAG-Dab-3' (SEQ ID NO: 79), wherein nucleotides preceded by a "+" are LNA modified nucleotides, MAXN is fluorescent moiety, and Dab is diaminobenzidine.

In another embodiment, the LNA probe comprises the nucleic acid sequence of 5'-MAXN GGGCC+C+ AAGGTCAGAGA-Dab-3' (SEQ ID NO: 80), wherein nucleotides preceded by a "+" are LNA modified nucleotides, MAXN is fluorescent moiety, and Dab is diaminobenzidine.

In some embodiments, the mutant allele comprises a variant that encodes a GNA11 protein of variant Q209L. In another embodiment, the mutant allele comprises the variant described as COSM110736 in COSMIC. In yet another embodiment, the wild-type allele comprises the sequence CCAGC (SEQ ID NO: 81), as compared to the mutant allele at the corresponding positions comprising a variant comprising the sequence CCTGC (SEQ ID NO: 82). In still another embodiment, the wild-type allele comprises A, or Adenine, as compared to the mutant allele comprising a variant comprising T, or Thymine.

In some embodiments, the forward primer comprises the nucleic acid sequence of 5'-GCAGATTGGGCCT-TGGGGCG-3' (SEQ ID NO: 83). In another embodiment, the reverse primer comprises the nucleic acid sequence of 5'-TCGCTGAGGGCGACGAGAAAC-3' (SEQ ID NO: 84). In yet another embodiment, the PNA blocker comprises the nucleic acid sequence of 5'-GGGCCAGCGGTCG-GAGC-3' (SEQ ID NO: 85).

In some embodiments, the LNA probe comprises the nucleic acid sequence of 5'-GGG+CC+T+GCGGTCGG-3' (SEQ ID NO: 86), wherein nucleotides preceded by a "+" are LNA modified nucleotides.

In yet another embodiment, the LNA probe comprises the nucleic acid sequence of 5'-FAM-GGG+CC+T+GCG-GTCGG-Dab-3' (SEQ ID NO: 87), wherein nucleotides preceded by a "+" are LNA modified nucleotides, FAM is fluorescein moiety, and Dab is diaminobenzidine.

the LNA probe comprises the nucleic acid sequence of 5'-MAXN-GGG+CC+T+GCGGTCGG-Dab-3' (SEQ ID NO: 88), wherein nucleotides preceded by a "+" are —LNA modified nucleotides, MAXN is fluorescent moiety, and Dab is diaminobenzidine.

In some embodiments, the mutant allele comprises a variant that encodes an H3F3A protein of variant 1(27M. In another embodiment, the mutant allele comprises the variant described as COSM327928 in COSMIC. In yet another embodiment, the wild-type allele comprises the sequence CAAGA (SEQ ID NO: 89), as compared to the mutant allele at the corresponding positions comprising a variant comprising the sequence CATGA (SEQ ID NO: 90). In still another embodiment, the wild-type allele comprises A, or Adenine, as compared to the mutant allele comprising a variant comprising T, or Thymine.

In some embodiments, the mutant allele comprises a variant that encodes an H3F3A protein of variant G34R. In another embodiment, the mutant allele comprises the variant described as COSM957499 in COSMIC. In yet another embodiment, the wild-type allele comprises the sequence AGGGG (SEQ ID NO: 91), as compared to the mutant allele at the corresponding positions comprising a variant comprising the sequence AAGGG (SEQ ID NO: 92). In still another embodiment, the wild-type allele comprises G, or Guanine, as compared to the mutant allele comprising a variant comprising A, or Adenine.

In some embodiments, the forward primer comprises the nucleic acid sequence of 5'-CTGCCCGCAAATCGAC-CGGT-3' (SEQ ID NO: 93). In another embodiment, the reverse primer comprises the nucleic acid sequence of 5'-GGATACATACAAGAGAGACTTTGTC-3' (SEQ ID NO: 94). In yet another embodiment, the PNA blocker comprises the nucleic acid sequence of 5'-GCCGCTCG-CAAGAGTGCGCC-3' (SEQ ID NO: 95). In another embodiment, the PNA blocker comprises the nucleic acid sequence of 5'-TTCTTCACCCCTCCAGTAG-3' (SEQ ID NO: 96).

In some embodiments, the LNA probe comprises the nucleic acid sequence of 5'-CGCTCGC+A+T+GAGTG-3' (SEQ ID NO: 97), wherein nucleotides preceded by a "+" are LNA modified nucleotides.

In another embodiment, the LNA probe comprises the nucleic acid sequence of 5'-TACT+GGA+A+GG+GT-GAAGA-3' (SEQ ID NO: 98), wherein nucleotides preceded by a "+" are LNA modified nucleotides.

In other embodiments, the LNA probe comprises the nucleic acid sequence of 5'-FAM-CGCTCGC+A+T+GAGTG-Dab-3' (SEQ ID NO: 99), wherein nucleotides preceded by a "+" are LNA modified nucleotides, FAM is fluorescein moiety, and Dab is diaminobenzidine.

In yet another embodiment, the LNA probe comprises the nucleic acid sequence of 5'-FAM-TACT+GGA+A+GG+GT-GAAGA-Dab-3' (SEQ ID NO: 100), wherein nucleotides preceded by a "+" are LNA modified nucleotides, FAM is fluorescein moiety, and Dab is diaminobenzidine.

In another embodiment, the LNA probe comprises the nucleic acid sequence of 5'-MAXN-CGCTCGC+A+T+GAGTG-Dab-3' (SEQ ID NO: 101), wherein nucleotides preceded by a "+" are LNA modified nucleotides, MAXN is fluorescent moiety, and Dab is diaminobenzidine.

In still another embodiment, the LNA probe comprises the nucleic acid sequence of 5% MAXN-TACT+GGA+A+GG+GTGAAGA-Dab-3' (SEQ ID NO: 102), wherein nucleotides preceded by a "+" are LNA modified nucleotides, MAXN is fluorescent moiety, and Dab is diaminobenzidine.

In some embodiments, two or more mutant alleles of TERT and/or IDH are detected simultaneously. In some embodiments, the two or more mutant alleles of TERT and/or IDH are detected simultaneously in the same well.

In some embodiments, a positive control genomic DNA is included, comprising DNA which is homozygous, hemizygous or heterozygous for the mutant allele. In some aspects, a negative control genomic DNA is included, wherein the negative control contains only wild type sequence for the target allele.

In some embodiments, the control genomic DNA is derived from glioma cell line LN428, which is heterozygous for TERT C228T. In some embodiments, the control genomic DNA is derived from glioma cell line LN443, which is homozygous for TERT C250T.

In some embodiments, the control genomic DNA is derived from primary glioma cell line BT142, which is homozygous for IDH1 R132H.

In some embodiments, the control genomic DNA template is derived from a melanoma cell or a melanoma cell line. In some embodiments, the positive control genomic DNA is synthetic. In some embodiments, the negative control genomic DNA template is derived from HCC1143 cell line, which is homozygous wild-type for TERT C228T, TERT C250T, and IDH1 R132. In some embodiments, the negative control genomic DNA template is derived from BL1954 cell line, which is homozygous wild-type for TERT C228T, TERT C250T, and IDH1 R132. In some embodiments, the negative control genomic DNA template is synthetic.

In some embodiments, the system or method includes a high-speed DNA polymerase. In some embodiments, the system or method includes a high-speed DNA polymerase has an elongation rate of about 1 kb/second. In some embodiments, the system or method includes a high-speed DNA polymerase that is Kapa 2G FAST DNA Polymerase.

In some embodiments, the system includes one or more multi-well plates.

In some embodiments, the system includes DNA extraction reagents. In some embodiments, the DNA extraction reagents are able to be used to extract DNA in 15 minutes or less.

In some embodiments, the system includes a cell lysis buffer. In some embodiments, the system includes Proteinase K. In some embodiments, the system includes deoxynucleotide triphosphates (dNTPs). In some embodiments, the system includes $MgCl_2$.

In some embodiments, the sample is from a patient or human subject. In some embodiments, the sample is from a tumor or metastatic lesion. In certain embodiments, the sample comprises tissue from a model organism, a cell from a tissue biopsy obtained from a subject, a cancer cell, nucleated cell obtained from blood obtained from a subject, or a circulating cancer cell. In some embodiments, the sample comprises a cancer cell. In other embodiments, the sample comprises the sample comprises a tissue biopsy, blood, plasma, serum, cerebrospinal fluid, or one or more circulating cancer cells from the subject. In another embodiment, the sample comprises tissue from the subject, or one or more cancer cells from the subject. In some embodiments, the sample is from a skin biopsy. In another embodiment, the sample comprises at least one component obtained from a body fluid. In yet another embodiment, the body fluid is selected from blood, serum, plasma, cerebrospinal fluid, saliva, urine, semen, stool, lymph, and peritoneal fluid. In some embodiments, the sample comprises at least one component obtained from blood from a patient or human subject. In some embodiments, the sample comprises a circulating cancer cell. In still another embodiment, the sample comprises at least one component obtained from a body tissue. In a further embodiment, the body tissue is an endobronchial brushing or an endotracheal brushing. In another embodiment, the sample comprises tissue from a model organism, a cell from a tissue biopsy obtained from a subject, a cancer cell, nucleated cell obtained from blood obtained from a subject, or a circulating cancer cell.

In some embodiments, the sample comprises blood from the subject. In some embodiments, the blood from the subject comprises one or more circulating cancer cells. In some aspects the blood from a subject comprises serum. In some embodiments, the sample comprises tissue from the subject. In some embodiments, the tissue from the subject comprises one or more cancer cells.

In some embodiments, the cancer is selected from the group consisting of: glioma, glioblastoma multiforme, melanoma, small cell lung cancer, non-small cell lung cancer, breast cancer, ovarian cancer, melanoma, uveal melanoma, bladder cancer, colon cancer, and lung cancer. In some embodiments, the cancer is a glioma. In some embodiments, the glioma is selected from the group consisting of: high grade glioma, diffuse astrocytoma, oligodendroglioma, oligoastrocytoma, secondary glioblastoma, and primary glioblastoma. In some embodiments, the cancer is a melanoma. In another embodiment, the cancer is a glioma, high grade glioma, diffuse astrocytoma, oligodendroglioma, oligoastrocytoma, secondary glioblastoma, primary glioblastoma, diffuse intrinsic pontine glioma, a melanoma, or uveal melanoma.

In some embodiments, the sample comprises archival tissue. In some embodiments, the archival tissue is formalin-fixed paraffin embedded.

In some embodiments, the sample from the subject is taken from a concurrent surgical procedure involving the subject and a surgeon, wherein the sample from the subject is obtained in rapid fashion, and results of the method are available to the surgeon to guide further treatment of the subject during the surgical procedure. In some embodiments, the method includes subsequent resection of a glioma tumor in the subject. In some embodiments, the method includes inserting a therapeutic drug-coated wafer into a central cavity of a tumor in the subject.

In some embodiments, the method includes calculating tumor burden or tumor purity in the sample, based on quantitative amount of mutant allele detected. In some embodiments, the method includes calculating tumor burden or tumor purity in the sample, based on quantitative amount of mutant allele detected relative to a standard curve generated from serial dilutions of control DNA.

In some embodiments, the mutant allele has an allelic frequency of 0.1% of the nucleic acid extracted from the sample.

In some embodiments, the method includes validation of genome editing in cell culture or in an animal model.

In some embodiments, the denaturing is initially done in about 1 round of incubation at about 95° C. for 2-5 minutes, and the annealing and amplifying are done in about 45 rounds of incubation at 95° C. for 1-12 seconds followed by about 62.5° C. to 64.5° C. for about 10-25 seconds. In some embodiments, the annealing and amplifying are done in about 40-50 rounds of incubation at 95° C. for 1-12 seconds followed by about 62.5° C. to about 64.5° C. for about 10-25 seconds. In some embodiments, the annealing and amplifying are done in about 35-45 rounds of incubation at 95° C. for 1-12 seconds followed by about 62.5° C. to about 64.5° C. for about 10-25 seconds. In some embodiments, the annealing and amplifying are done in about 40-45 rounds of incubation at 95° C. for 1-12 seconds followed by about 62.5° C. to about 64.5° C. for about 10-25 seconds.

In some embodiments, the melting temperatures of the forward primer, reverse primer, LNA probe and PNA blocker are about 62.5° C. to about 64.5° C. In some embodiments, the melting temperatures of the forward primer, reverse primer, LNA probe and PNA blocker are about 63.5° C.

In some embodiments, the amplicon is less than 70-300 nt in length.

In some embodiments, the denaturing, annealing and amplifying steps are performed in a thermocycler with a ramping rate of at least 1.6-3.1° C. per second.

Other embodiments will become apparent from a review of the ensuing detailed description, drawings, tables and accompanying claims.

BRIEF DESCRIPTION OF THE FIGURES

The foregoing and other features and advantages of the system and methods disclosed herein will be more fully understood from the following detailed description of illustrative embodiments taken in conjunction with the accompanying drawings.

FIG. 1 graphically depicts the sensitive detection of IDH1 R132H in a previously inconclusive brain biopsy.

FIG. 2 graphically depicts rapidly segregation of low and high grade gliomas by the method disclosed herein.

FIG. 3 graphically depicts intraoperative molecular characterization of glioma. FIG. 3A, entitled Case 1 demonstrates the detection of TERT promoter mutation from a specimen that was diagnosed as high grade glioma on frozen section analysis (single arrowhead indicating microvascular proliferation and double arrowhead indicating necrosis) and GBM on permanent section analysis. FIG. 3B, entitled Case 2 represents an instance of intraoperative detection of IDH1 R132 mutation, which was in disagreement with frozen specimen analysis of GBM, but in agreement with permanent section analysis of IDH1 mutant anaplastic oligoastrocytoma. Single black arrowhead represents microvascular proliferation, double arrowhead represents thrombosed vessel within necrotic focus, green arrowhead represents mitotic figure. Scale bars represent 10 μm.

FIG. 11A: Expanded heatmap from FIG. 2A demonstrating individual IDH1 R132H, TERT C228T and TERT C250T mutations for each glioma specimen. Glioma diagnoses were predicted as primary glioblastoma if TERT mutant and IDH1 R132 wild-type (FIG. 11B), oligodendroglioma if TERT and IDH1 R132H mutant (FIG. 11C), or diffuse glioma, oligoastrocytoma, or secondary glioblastoma if IDH1 R132H mutant and TERT wild-type (FIG. 11D). Combining the analysis for panels (c) and (d) yields the results for non-primary glioblastoma diagnoses (FIG. 11E). Listed in parentheses are 95% confidence intervals.

FIG. 13 graphically depicts a list of primers, detection probes and modified oligonucleotide blockers. Modified locked nucleic acids are indicated by a preceding "+". In FIG. 13, the forward primer for IDH1 is 5'-CCGGCTTGT-GAGTGGATGGGTAAAACCT-3' (SEQ ID NO: 29) and the reverse primer for IDH1 is 5'-CATTATTGCCAACAT-GACTTACTTGATCCCC-3' (SEQ ID NO: 30). The TaqMan probe for detection of the IDH1 R132H mutation is 5'-FAM-AGG+T+C+A+T+CAT+GC-Dab-3' (with the locked nucleic acid being denoted by a preceding+; SEQ ID NO: 36). The peptide nucleic acid (PNA blocker) for blocking amplification of wild-type IDH1 is 5'-AGGTCGT-CATGC-3' (SEQ ID NO: 20). The TERT forward primer is 5'-CACGTGCGCAGCAGGACGCAG-3' (SEQ ID NO: 9) and the TERT reverse primer is 5'-CTTCACCTTCCA-GCTCCGCCTC-3' (SEQ ID NO: 10). The TaqMan probe for detecting TERT C228T is 5'-FAM-CCCAGCCCC+T+TCCGGGCCC-Dab-3' (SEQ ID NO: 15) and for detecting TERT C250T is 5'-FAM-CCGACCCC+T+TC-CGGGTCCC-Dab-3' (SEQ ID NO: 16). The PNA blockers for blocking amplification of TERT C228 and TERT C250 are 5'-CCCAGCCCCCTCCGGGCCC-3' (SEQ ID NO: 11) and 5'-CCGACCCCTCCCGGGTCCC-3' (SEQ ID NO: 12), respectively.

FIGS. 14A-1 and 14A-2 graphically depict the rapid detection of TERT promoter mutant alleles to discriminate malignant skin pathology and show that detection of cell free alleles in serum correlates with systemic disease burden.

FIG. 16 graphically depicts the detection of cell free circulating mutant TERT promoter allele C228T DNA in a sample from a patient with glioblastoma multiforme recurrence, not responding to concurrent chemoradiation. Cell free DNA was purified from serum of patient obtained at time of clinical and radiographic progression of GBM in middle of postoperative concurrent chemoradiation. The method disclosed herein detected presence of TERT C228T. For comparison, 100% genomic extract from LN428 and 1% LN428 extract diluted in wild-type HCC1143 lymphocytes is overlayed.

FIG. 17 graphically depicts a table of cell free circulating DNA samples.

FIG. 19 graphically depicts the detection of decreased cell free circulating TERT C228T in a patient with metastatic melanoma in response to treatment.

DETAILED DESCRIPTION

Figure 1A:
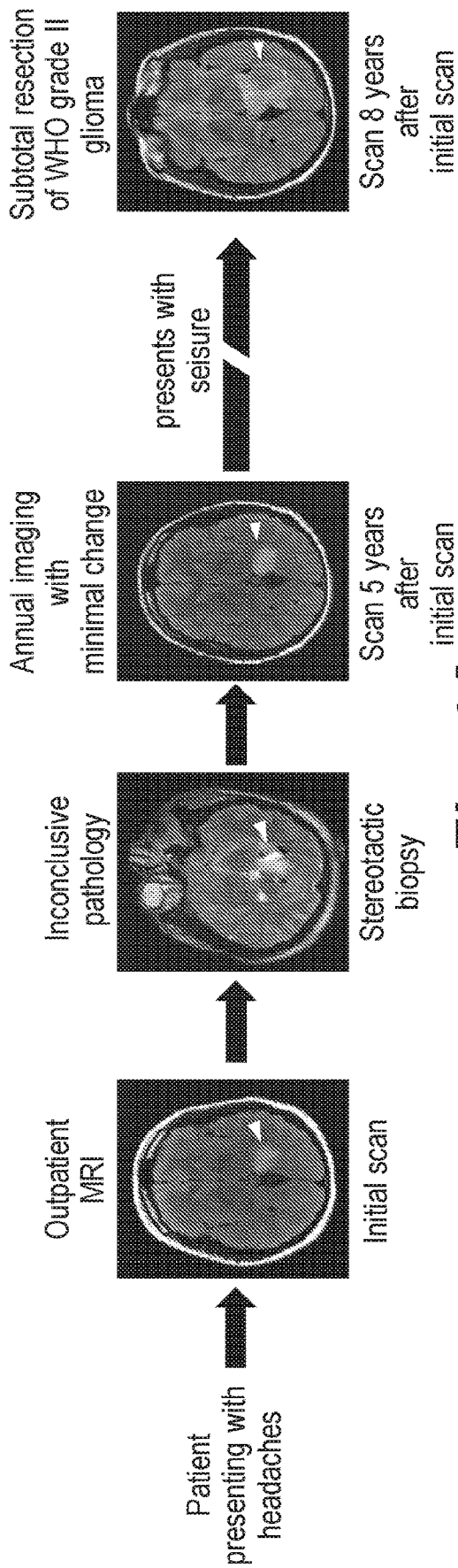
FIG. 1A shows the clinical course of patient with temporal lobe abnormality eventually diagnosed as oligoastrocytoma eight years after initial presentation. This 16-year-old patient presented with headaches and MRI revealed a non-enhancing lesion in the left medial temporal lobe (red arrowhead). Biopsy was obtained, but was pathologically inconclusive. Intraoperative MRI confirmed that the stereotactic needle was centered in the lesion (yellow arrowhead). She was subsequently followed for five years with minimal radiographic change. She re-presented with generalized seizures and radiographic progression three years later. At that time she underwent subtotal resection revealing WHO II oligoastrocytoma.

Before the invention is described, it is to be understood that this invention is not limited to particular methods and experimental conditions described, as such methods and conditions may vary. It is also to be understood that the terminology used herein is for the purpose of describing particular embodiments only, and is not intended to be limiting, because the scope of the invention will be limited only by the appended claims.

Unless defined otherwise, all technical and scientific terms used herein have the same meaning as commonly understood by one of ordinary skill in the art to which this invention belongs.

The present disclosure provides sensitive methods that detect cancer-specific mutations in specimens, by including the following features: (1) forward and reverse primers to a target sequence, (2) inclusion of modified oligonucleotides with peptide nucleic acid (PNA) backbones to block logarithmic amplification of wild-type alleles, and (3) incorporation of locked nucleic acids (LNA) into mutant allele detection probes to increase specificity.

In certain embodiments, the term "wild-type allele" as used herein means an allele of a gene which has the highest gene frequency in a given population. In certain embodiments, this population is a population of humans in a certain geographical area. This area can be a continent, country, state, province or municipality. In certain embodiments, the population can be a human population separated by gender, race, national origin or age.

In other embodiments, "wild-type allele" refers to an allele that is not associated with higher prevalence of occurrence of a disease state relative to a "mutant allele" that is associated with a higher prevalence of occurrence of a disease state. In certain embodiments, that disease state is cancer. In other embodiments, the cancer is melanoma or glioma.

The terms "genetic information" and "gene" as used herein include various components associated with the chromosomal locus that encodes a functional sequence. In most embodiments a "gene" includes not only a transcriptional coding region which encodes information of mRNA, tRNA, rRNA, snRNA, and the like, but also includes one or more regulatory regions such as a promoter or enhancer which is required for gene expression. Where appropriate, one or more of these regions may be distinguished individually, e.g., a promoter sequence or a coding sequence.

In certain embodiments, the term "mutant allele" as used herein means an allele of a gene which is associated with one or more disease aspects. As used herein a mutant allele does not have the highest gene frequency in a given population. This mutant allele could have the second, third, fourth, fifth, sixth, seventh, eighth, ninth or tenth highest gene frequency among known alleles in a population. As explained above, in certain embodiments, this population is a population of humans in a certain geographical area. This area can be a continent, country, state, province or municipality. In certain embodiments, the population can be a human population separated by gender, race, national origin or age.

In other embodiments, "mutant allele" refers to an allele that is associated with higher prevalence of occurrence of a disease state relative to a "wild-type allele" that is not associated with a higher prevalence of occurrence of a disease state. In certain embodiments, that disease state is cancer. In other embodiments, the cancer is melanoma or glioma. In another embodiment, the cancer is a glioma, high grade glioma, diffuse astrocytoma, oligodendroglioma, oligoastrocytoma, secondary glioblastoma, primary glioblastoma, diffuse intrinsic pontine glioma, a melanoma, or uveal melanoma.

The term "mutation" as used herein means a change in the sequence of a nucleic acid such as DNA and RNA, and includes a base substitution, insertion, deletion, inversion, duplication, translocation, and the like used in genetics and the like. In certain embodiments, this mutation represents the physical genetic difference between a wild-type allele and a mutant allele. The region of the mutation in a mutant allele is not limited to a transcriptional region, but includes a regulatory region such as a promoter which is required for gene expression. In this regard, the mutation in a mutant allele does not require a functional change.

In certain embodiments, "variant" refers to an alteration in the normal sequence of a gene. A variant may include a single nucleotide polymorphism, a mutation, or a gene copy number variation.

In certain embodiments, "single nucleotide polymorphism" (SNP) refers to a single substitution of a nucleotide base for another at a particular site that occurs in more than 1% of the general population of a species. A single nucleotide polymorphism can have up to four possible versions at its site: A, C, G or T. Single nucleotide polymorphisms occur about once in every 300 nucleotide base pairs in the human genome. Linked or indicative SNPs are not located within genes and do not affect function of a protein. Causative SNPs include coding and non-coding SNPs, and affect protein function. Coding SNPs are found in the coding region of a gene and change the amino acid sequence of the coded protein product. Non-coding SNPs are found in the regulatory regions of a gene, and affect expression of the gene, including amount, timing and/or location of the gene's expression.

In certain embodiments, "somatic variant" refers to an alteration of DNA that occurs in any cell of the body other than the germ cells, and is neither inherited from a parent nor passed to offspring.

In certain embodiments, "molecular diagnosis" refers to a diagnostic technique utilizing the analysis of one or more molecular and/or biological markers that define disease state, and can be used for diagnosing, monitoring or staging a disease, determining risk, or determining a therapeutic approach.

The term "target site" as used herein means a site in which a mutated base exists or a base is deleted by a mutation in a mutant allele, and a site to be detected as a target using the methods disclosed herein, including a wild-type allele. For example, in the case of a base substitution, the target site is a base which is substituted in both a wild-type allele and a mutant allele. In the case of an insertion, the target site in a mutant allele is an inserted base, and the target site in a wild-type allele is a site into which the base is inserted in the mutant allele. In the case of a deletion, the target site in a mutant allele is a site in which a base is deleted by the deletion, and the target site in a wild-type allele is the deleted base in the mutant allele. The sequence of a target site may be a site having a sequence which encodes genetic information (sometimes referred to as a sense site or sequence), or a site having a sequence complementary to the sense sequence (sometimes referred to as an antisense site or sequence).

As used herein, the term "complementary" refers to the complement of a DNA sequence as the sequence with each based changed to its complement pair (e.g., G to C, C to G, A to T and T to A).

The term, "reverse complementary" of a DNA sequence, as used herein, is the sequence backwards orientation (i.e, the reverse of a sequence as read from 5' to 3' would be the sequence from 3' to 5'), and with each based changed to its complement pair (e.g., G to C, C to G, A to T and T to A).

The term "amplicon" as used herein means a molecule of DNA or RNA that is the source and/or product of natural or artificial amplification or replication events. It can be formed using various methods including polymerase chain reactions (PCR), ligase chain reactions (LCR), or natural gene duplication. In this context, "amplification" or "amplifying" refers to the production of one or more copies of a genetic fragment or target sequence, specifically the amplicon. As the product of an amplification reaction, amplicon is used interchangeably with common laboratory terms, such as PCR product. The amplicon used in the methods disclosed herein can generally be between 70-300 nt in length. The amplicon used in the methods herein can be less than 300, 200, 100, 90, 80 or 70 nt in length. In certain embodiments, the amplicons used according to the disclosure are 70-80, 70-90, 70-100, 70-200, 70-300, 80-90, 80-100, 80-200, 80-300, 90-100, 90-200, 90-300, 100-200, 100-300 or 200-300 nt in length.

Primers and Probes

The term "forward primer" as used herein refers to a short, single-stranded DNA sequence that binds to a target DNA sequence and enables addition of new deoxyribonucleotides by DNA polymerase at the 3' end, wherein the primer binds upstream of a target site and to the sense strand of the target nucleic acid. According to certain embodiments, the forward primer is 18-35, 19-32 or 21-31 nt in length. The nucleotide sequence of the forward primer is not limited, so long as it specifically hybridizes with part of or an entire target site, and its Tm value may be within a range of 50° C. to 65° C., and in particular may be within a range of 62.5° C. to 64.5° C., may be within a range of 63.0° C. to 64.0° C., may be within a range of 63.3° C. to 63.7° C., and may be 63.5° C. The nucleotide sequence of the forward primer may be manually designed to confirm the Tm value using a primer Tm prediction tool.

The term "reverse primer" as sued herein refers to a short, single-stranded DNA sequence that binds to a target DNA sequence and enables addition of new deoxyribonucleotides by DNA polymerase at the 3' end, wherein the primer binds downstream of a target site and to the antisense strand of the target nucleic acid. According to certain embodiments, the reverse primer is 18-35, 19-32 or 20-31 nt in length. The nucleotide sequence of the reverse primer is not limited, so long as it specifically hybridizes with part of or an entire target site, and its Tm value may be within a range of 50° C. to 65° C., and in particular may be within a range of 62.5° C. to 64.5° C., may be within a range of 63.0° C. to 64.0° C., may be within a range of 63.3° C. to 63.7° C., and may be 63.5° C. The nucleotide sequence of the reverse primer may be manually designed to confirm the Tm value using a primer Tm prediction tool.

Peptide nucleic acids (PNA) are artificial, chemically synthesized nucleic acid analogues which have a structure in which a basic backbone of a nucleic acid constituted by pentose and phosphoric acid is replaced with a polyamide backbone having no charge including glycine as units. PNA binds more specifically and strongly to a nucleic acid having a complementary nucleotide sequence in comparison with DNA and RNA. In contrast, since PNA is a chemically synthesized substance, it has a property that nucleic acid polymerases and nucleases do not act thereon. By utilizing such a property, a method for selectively amplifying only a mutated gene by suppressing a wild-type gene by performing a PCR method using a PNA oligomer that is specific to a wild-type gene is known.

The term "PNA" as used herein includes not only conventional PNA, but also a PNA derivative which is an improvement based on PNA and has properties similar to PNA, for example, gripNA provided by Active Motif.

The term "PNA blocker" as used herein means an oligonucleotide comprising PNA which hybridizes with a target site. A PNA blocker comprises an oligonucleotide comprising one or more peptide nucleic acids that acts to block (i.e., inhibit or cause a relative decrease in) amplification of the wild-type allele, and does not block amplification of the mutant allele. A PNA blocker may comprise a mixture of nucleic acids, PNA, and amino acids. A PNA blocker may comprise a backbone containing amide bonds, deoxyribose sugar, ribose sugar, and charged phosphate groups. In this context, "block" is intended to mean inhibit or cause a decrease in relative amplification of the targeted wild-type allele to which the PNA blocker hybridizes. Such inhibition or relative decrease in amplification of the wild-type allele allows sensitivity of the methods disclosed herein in detecting very low copy number of the variant allele. The PNA blocker hybridizes to a region of the wild-type allele located within the region amplified by the forward and reverse primer. The PNA blocker can be composed of PNA over a portion of its length or the entire sequence. Therefore, when it hybridizes with a nucleotide sequence, it shows an extremely high selectivity to the nucleotide sequence due to the properties of PNA. Further, since PNA is not affected by nucleic acid polymerases and nucleases, the PNA blocker does not function as a primer and is resistant to nucleases. The nucleotide sequence of the PNA blocker is not limited, so long as it specifically hybridizes with part of or an entire target site, and its Tm value may be within a range of 50° C. to 65° C., and in particular may be within a range of 62.5° C. to 64.5° C., may be within a range of 63.0° C. to 64.0° C., may be within a range of 63.3° C. to 63.7° C., and may be 63.5° C. The nucleotide sequence of the PNA blocker may be manually designed to confirm the Tm value using a PNA Tm prediction tool. The length of the PNA blocker is not limited, so long as it is 10 to 25 nucleotides. The length of the PNA blocker can be 12 to 22 nucleotides. The length of the PNA blocker can be 12 to 19 nucleotides. Since the prevalence of a wild-type gene is larger than that of a mutated gene in a gene pool, the concentration of the PNA blocker may be 2-10 times or more that of the LNA probe in the reaction solution for gene amplification so that the PNA blocker can sufficiently hybridize with the wild-type gene. For example, when the concentration of the LNA probe is 100 nmol/L, the concentration of the PNA blocker is approximately 1 µmol/L, or approximately 5 µmol/L.

Locked nucleic acids (LNA) are artificial, chemically synthesized nucleic acid analogues comprising an RNA nucleoside in which the 2' oxygen and 4' carbon of the ribose moiety are chemically linked (e.g., by a methylene bond). Similarly to PNA, LNA has high affinity for a nucleic acid having a complementary nucleotide sequence, and binds thereto more specifically and strongly in comparison with DNA and RNA. In contrast, unlike PNA, LNA has sensitivity against nucleases, and may also act as a primer for nucleic acid polymerases. By utilizing such properties, a method for detecting and using a PCR method with an LNA probe was developed.

The term "LNA" as used herein includes not only conventional LNA, but also a LNA derivative which is an improvement based on LNA and has properties similar to LNA.

The term "LNA probe" as used herein means a probe which hybridizes with a target site, and at least one nucleotide contained in the DNA sequence of which is replaced with LNA. This embodiment is characterized by the fact that the nucleotide sequence of the LNA probe is a sequence complementary to that of the mutated gene. The LNA probe hybridizes to the target sequence at a location that is between where the forward primer and reverse primer binds. The nucleotide sequence of the LNA probe is not limited, so long as it specifically hybridizes with part of or an entire target site, and its Tm value may be within a range of 50° C. to 65° C., and in particular may be within a range of 62.5° C. to 64.5° C., may be within a range of 63.0° C. to 64.0° C., may be within a range of 63.3° C. to 63.7° C., and may be 63.5° C. The nucleotide sequence of the LNA probe may be manually designed to confirm the Tm value using an LNA Tm prediction tool. The number of nucleotides contained in the LNA probe is 10 to 50 nucleotides, and may be 15 to 25 nucleotides. The length of the LNA probe can be 12 to 22 nucleotides. The length of the LNA probe can be 12 to 19 nucleotides. The number of LNA present within the LNA probe is not limited, so long as it is one or more, and all the nucleotides may be replaced with LNA. With respect to a position at which a nucleotide is replace with LNA in the LNA probe, when there are one or more bases which are not found in a target region of a wild-type gene, at least one of these bases may be replaced with LNA. For example, in the case that a mutation is an insertion of some bases, at least one of the inserted bases may be replaced with LNA.

The melting temperatures of the forward primer, reverse primer, LNA probe and PNA blocker can also be about 62.5° C. to about 64.5° C., may be about 63.0° C. to about 64.0° C., may be about 63.3° C. to about 63.7° C., and may be 63.5° C. In particular, the melting temperatures of the forward primer, reverse primer, LNA probe and PNA blocker can be about 63.5° C. to 63.7° C. In particular, the melting temperatures of the forward primer, reverse primer, LNA probe and PNA blocker can be about 63.5° C. The Tm values may be determined using the disclosed buffer conditions. Other primer lengths and Tm values known in the art may be used where appropriate, e.g., where different buffer systems are used, and/or where stringency requirements differ.

Systems and Methods for Detecting Single Nucleotide Polymorphisms

The system and methods of use described herein include or make use of the polymerase chain reaction (PCR). PCR relies on thermal cycling, which consists of cycles of repeated heating and cooling of the reaction for DNA denaturation, annealing and enzymatic elongation of the amplified DNA. Components of PCR include primers that contain sequences which are complementary to the target region(s), and a DNA polymerase. In the PCR reaction, the DNA generated (sometimes called the amplicon) is itself used as a template for further replication, creating a chain reaction that exponentially amplifies the DNA template. PCR can be extensively modified to perform a wide array of genetic manipulations.

Most applications of PCR applications utilize DNA polymerase that is heat-stable, such as Taq polymerase (originally isolated from *Themus aquaticus*). The DNA polymerase generates a new strand of DNA from nucleotides, where a single-stranded DNA is used as a template and DNA oligonucleotides or primers, are used for initiation of DNA synthesis. PCR methods generally use thermal cycling, which is alternate heating and cooling of the PCR reaction through a set series of temperature steps.

First, the strands of the DNA are separated at a high temperature in a process called DNA melting or denaturing. Next, the temperature is lowered, allowing the primers and the strands of DNA to selectively anneal, creating templates for the polymerase to amplify the target DNA. Use of primers that are complementary to the DNA region targeted for amplification under specific thermal cycling conditions allows for selectivity of the reaction.

In general, a typical PCR process requires a number of components and reagents. These include: a DNA template that contains the target region of interest to be amplified; two primers that are complementary to the 3' (three prime) ends of each of the sense and anti-sense strand of the DNA target (a forward primer and a reverse primer); a DNA polymerase with a temperature optimum at around 60-70° C.; deoxynucleotide triphosphates (dNTPs); a buffer solution, providing a suitable chemical environment for optimum activity, binding kinetics, and stability of the DNA polymerase; bivalent cations such as magnesium or manganese ions; generally $Mg^{2+}$ is used, but $Mn^{2+}$ can be used, where higher $Mn^{2+}$ concentration can increase the error rate of the DNA polymerase; and monovalent cations, such as potassium ions.

PCR can comprise a series of 20-50 repeated temperature cycles, with each cycle commonly consisting of 2-3 discrete temperature steps. Temperatures and the duration of each step can vary depending on a number of parameters. These include the enzyme used for DNA synthesis, the concentration of divalent ions and dNTPs in the reaction, and the melting temperature (Tm) of the primers. Some typical PCR steps include the following:

Initial step: This step involves heating the reaction to a temperature of about 94-96° C. which can be held for about 1-9 minutes. In the present disclosure, methods may not require or include this initial step. In some cases, this step is performed at about 95° C. for 2-5 minutes.

Denaturing step: This step involves heating the reaction to 94-98° C. for 1-12 seconds. It causes DNA melting of the DNA template by disrupting the hydrogen bonds between complementary bases, yielding single-stranded DNA molecules. In the present disclosure, denaturing may be done at about 95° C. for 1-12 seconds.

Annealing step: The reaction temperature is lowered to 50-65° C. for 10-25 seconds which allows the primers to anneal to the single-stranded DNA template. The polymerase then binds to the hybridized primer and template and begins DNA polymerization. In the present disclosure, the annealing step may be done at about 62.5° C. to 64.5° C. for about 10-25 seconds. In some cases, this step is performed at about 63.5° C.

Extension/elongation (or amplifying) step: This step generally uses a temperature of about 60-72° C. with a DNA polymerase enzyme. At this step, the DNA polymerase synthesizes a new DNA strand complementary to the DNA template strand by adding dNTPs that are complementary to the template in 5' to 3' direction, condensing the 5'-phosphate group of the dNTPs with the 3'-hydroxyl group at the end of the nascent (extending) DNA strand. The extension time depends both on the DNA polymerase used and on the length of the DNA fragment to be amplified. In the present disclosure, the amplifying step may be done at about 62.5° C. to 64.5° C. for about 10-25 seconds. In some cases, this step is performed at about 63.5° C.

The methods of the present disclosure use a combined annealing and extension/elongation step. In other words, the annealing and amplifying steps occur at the same temperature condition and during the same amount of time. Such modification optimizes the process for shorter total reaction times, resulting in a method that is useful for applications requiring a rapid process as described herein.

For example, in the present methods, the annealing and amplifying can occur in a single step at about 62.5° C. to 64.5° C. for about 10-25 seconds. In some cases, the annealing and amplifying can occur in a single step performed at about 63.5° C. for about 10-25 seconds.

In the case of the methods disclosed herein, the annealing and elongation steps occur at the same temperature conditions, allowing optimization to the method for applications where a rapid process is desired.

The system and methods provided herein make use of a variation of PCR called Quantitative PCR (qPCR), which measures the accumulation of DNA product after each round of PCR amplification in order to measure the quantity of a target sequence (such measurement often occurring in real-time). Quantitative PCR can be used to determine whether a particular sequence is present in a sample, and to determine the number of its copies in the sample. Quantitative PCR often methods use fluorescent dyes, such as Sybr Green, EvaGreen or fluorophore-containing DNA probes, such as TaqMan, to measure the amount of amplified product during the reaction in real time.

Features of the System and Methods

The system and methods herein are designed to generate sensitive detection of alleles with very low prevalence, through the inclusion of modified oligonucleotides with peptide nucleic acid (PNA) backbones to block logarithmic amplification of wild-type alleles, and incorporation of locked nucleic acids (LNA) into mutant allele detection probes to increase specificity. In the case of the present methods disclosed herein, the forward primer, the reverse primer, the LNA probe, and the PNA blocker are capable of recognizing their target sequences under same temperature conditions, allowing the annealing and elongation steps to occur at the same temperature conditions, thereby optimizing the method for applications where a rapid process is desired or required. The system and methods herein are optionally adapted to overcome the low complexity and/or high GC content of a target sequence, and/or to detect cancer-specific mutations in specimens with low tumor size, mass and/or density.

First, a PNA blocker comprising PNA having a sequence complementary to a target site of a wild-type gene, and an LNA probe having a sequence complementary to a target site of a mutant allele and comprising DNA that contains LNA, are allowed to contact a forward primer, a reverse primer, and a DNA template in a buffer or reaction solution for gene amplification. Since wild-type genes are generally present in a sample DNA in large amounts, the PNA blocker is added in slight excess amount. As a result, the PNA blocker, the LNA probe, and the forward primer and reverse primer hybridize with the respective corresponding complementary sequences on the genes to be detected. Most or parts of the nucleotide sequences of the PNA blocker and the LNA probe accord with each other, because their target sites are the same. Therefore, both the hybridizations to the target sites essentially compete with each other. However, since PNA and LNA exhibit a high specificity to each complementary nucleotide sequence, even if the mutation is a difference in only one nucleotide, almost all the PNA blocker hybridizes with the target site on the wild-type gene, and almost all the LNA probe hybridizes with the target site on the mutant allele.

Next, the resulting reaction solution for gene amplification is subjected to a primer elongation reaction using a gene amplification method. Since the PNA blocker does not function as a primer, no elongation reaction occurs from it. Therefore, the amplification of the detection region comprising the target site of the wild-type gene is suppressed by the hybridization of the PNA blocker. In contrast, LNA does not exhibit an inhibitory activity to primer elongation like PNA. Since the LNA probe can function as a primer, an elongation reaction occurs, and the region comprising the target site of the mutant allele is amplified over the LNA probe site and between the forward primer and reverse primer.

The amplicon length is typically dictated by experimental goals. In the methods of the present disclosure, which utilize quantitative PCR, goal for amplicon length should be 70 to 300 bases for optimal PCR efficiency and to allow for shorter annealing and elongation times. For many cases, the amplicon length is closer to 100 bp or less. Given the known positions of the forward primer and the reverse primer with respect to the template, the length of the product is calculated as: Product length=(Position of antisense primer)–(Position of sense primer)+1.

The melting temperature ($T_m$) of the amplicon is the temperature at which one half of the DNA duplex will dissociate and become single stranded. The stability of a primer-template DNA duplex can be measured by the melting temperature ($T_m$). Low sequence complexity and/or high GC content can result in an amplicon having a melting temperature that is relatively higher than a sequence with greater sequence complexity and/or lower GC content. In the methods disclosed herein, the Tm of the amplicon is generally about 62.5° C. to about 64.5° C.

The length of the extension cycle required can be affected by amplicon size. In the methods of the present disclosure, the extension cycle is shorter (in part due to amplicon size designed to be shorter) to allow for faster extension of the amplicon. The length of extension steps can also be affected by the DNA polymerase used. DNA polymerases used in the present methods are described herein.

After the completion of the elongation reaction, the PNA blocker, the LNA probe, and the forward primer and the reverse primer are again hybridized with the corresponding complementary sequences on the genes to be detected. The cycles of gene amplification reaction are repeated by to selectively amplify a region comprising sequence of the mutant allele. The number of the cycles varies in accordance with the type of a DNA polymerase used, and is not limited, so long as it is within a range of 30 to 55 cycles. It can be 35 to 50 cycles. In particular, it can be 40 to 45 cycles.

In the present methods, the denaturing, annealing and amplifying steps can be done in about 35-50 rounds of incubation at 95° C. for 1-12 seconds followed by about 62.5° C. to 64.5° C. for about 10-25 seconds.

In some embodiments of the present methods, the quantitative PCR method comprises the following conditions. Forward and reverse primers for a target site of a gene are designed and empirically optimized for an anneal/elongation temperature of 63.5° C. 5' Nuclease probes against mutant alleles and corresponding PNA oligonucleotide blockers against wild-type alleles are designed to detect mutations in the target site of the gene. Optimal sensitivity was achieved through the use of two distinct gene wild-type PNA blocking oligonucleotides designed to these two respective sites. Similarly, 5' Nuclease probes and the PNA wild-type blockers were designed for optimal performance at 63.5° C. for the respective genomic templates.

For example, the primers for a target site of a gene include, but are not limited to, SEQ ID NOs: 9, 43, 52, 66, 67, 83, and 93 for forward primers and SEQ ID NOs: 10, 44, 53, 68, 69, 83, and 94 for reverse primers. The primers for a target site of a gene were used at final concentrations of 250-750 nM. For example, the LNA probes for a target site of a gene include, but are not limited to, SEQ ID NOs: 46, 50, 56, 61, 68, 75, 79. and 85 The LNA probe comprising locked nucleic acids for detection of a mutation in the target site of the gene was 250 nM. The peptide nucleic acid (PNA) probe for blocking wild-type gene amplification was 150-900 nM.

The qPCR reactions were run in 384-well plates on an ABI QuantStudio 6 instrument (Applied Biosystems) in the presence of 60 nM ROX to account for background fluorescence. Appropriate buffers include ABI GeneExpression 2X mastermix or KAPA 2G Fast Polymerase buffer A and enhancer to a final concentration of 1×. PCR cycling times were 95° C. for 3 minutes followed by 40-60 cycles at 95° C. for 10 seconds and 63.5° C. for 20 seconds.

In other embodiments, the qPCR reactions were run in 96-well plates on an ABI 7500 instrument (Applied Biosystems).

Detection of Amplified Product

The region of sequence which is derived from the mutant allele and amplified by the method is detected. The detection method is not limited, so long as the amplification of the region of the mutant allele can be confirmed. For example, the 5' terminus of the amplification primer may have been previously labeled with a fluorescent substance, and after the completion of the gene amplification reaction, fluorescent emission may be captured and detected using an appropriate detector. In these detection methods, results can be compared to the measured values with the results of an appropriate control. Further, confirmation of the presence of the target site of the mutant allele in the amplified product can be made by sequencing, or other method, including but not limited to immunohistochemistry, where available.

Polymerases

The system and methods provided herein are designed to give rapid and quantitative detection of a single nucleotide variant or polymorphism from a sample, and utilizes DNA Polymerase. In particular, a DNA Polymerase with a high rate of elongation can be used to optimize the amount of time needed to complete the quantification of the target site in the sample, facilitating a more rapid process. For example, such a polymerase such as has an elongation rate of about 1 kb/second. The DNA polymerase can be a high-speed DNA polymerase such as Kapa 2G FAST DNA Polymerase (Kapa Biosystems).

Buffers

The buffers or reaction solutions as described herein refer to a solution or solutions containing reagents and the like which are required for the gene amplification reaction in the gene amplification method. The formulation of the reaction solution for gene amplification may need minor modifications depending on the gene amplification method used, but the reaction solution for gene amplification basically contains 4 kinds of deoxynucleoside triphosphates (dATP, dTTP, dCTP, and dGTP: hereinafter collectively referred to as dNTPs) as substrates, a DNA polymerase as an enzyme, a magnesium ion as a cofactor for the enzyme, and amplification primers as primers for elongation, in a buffer. The concentrations of dNTPs may be selected within a range of 100 nmol/L to 400 nmol/L as a final concentration of each. A DNA polymerase having properties suitable for the gene amplification method used may be used. The concentration of the magnesium ion may be selected within a range of 1 mmol/L to 6 mmol/L as a final concentration.

The buffer has an optimum pH and an optimum salt concentration capable of obtaining the activity of the DNA polymerase. Various types of reaction solutions for gene amplification are commercially available for each gene amplification method, and one attached to such a commercially available kit may be used.

Kits

The system disclosed herein can be part of a kit, optionally including further components for use in the methods disclosed herein, or for other uses. In some cases, the kit can include DNA extraction reagents, in particular DNA extraction reagents which are suitable and/or designed for rapid extraction of DNA from a sample.

Kits can provide primers and LNA and PNA components that are specific for at least one target nucleic acid. A kit generally comprises the forward primer, reverse primer, LNA probe and PNA blocker for at least one target nucleic acid. The target nucleic acid can be a region of the TERT promoter, such as one or both somatic variants C228T and C250T, as further described herein. In such cases, the LNA probe can hybridize to a nucleotide region comprising a T at position 228 or 250, respectively, of the mutated allele of the TERT promoter and the PNA blocker hybridizes to a nucleotide region comprising a C at the corresponding position in a wild type allele. In some cases, the target nucleic acid is a region of the IDH1 gene, such as the nucleotide sequence encoding a somatic mutation at position 132 of the polypeptide. In such cases, the LNA probe can hybridize to a nucleotide region comprising a mutated codon encoding an amino acid selected from one or more of a histidine ("H"), cysteine ("C"), glycine ("G"), serine ("S") and leucine ("L") at position 132 of the mutated IDH1 protein and the PNA blocker hybridizes to a nucleotide region comprising a wild type codon encoding an arginine ("R") at the corresponding position in a wild type allele.

In some aspects, the kits can comprise primers, probes and blockers for more than one target nucleic acid, such as a kit comprising primers, probes and blockers for a variant of the TERT promoter, and primers, probes and blockers for one or more variants of the IDH1 gene.

Other Uses of the System and Methods

Intraoperative Uses

Intraoperative histopathology can be technically challenging in the setting of low cellularity lesions and small biopsy specimens, and these difficulties may hamper surgical decision-making. Cancer genome sequencing has revealed that many tumors can now be positively identified by recurrent genomic features. For instance, greater than 80% of gliomas can be identified and clustered by IDH1 and TERT promoter mutations, within groups that correspond closely to existing histopathologic classification. In accord, research techniques have applied real-time PCR detection of IDH1 mutation or mass spectrometry to the intraoperative detection of 2-hydroxyglutarate, the metabolite of mutant IDH1. In one aspect, the method disclosed herein is designed to simultaneously detect the distinguishing genomic features in both the TERT promoter and IDH1 in an intraoperative timeframe to sensitively detect diffuse glioma and guide neurosurgical resection. The methods provided herein could be used for real-time intraoperative diagnosis. In some embodiments, the intraoperative diagnosis can be used to confirm a diagnosis. In another embodiment, intraoperative diagnosis allows for intraoperative therapy. In yet another embodiment, the intraoperative therapy may comprise resection, thermal ablation therapy, laser microsurgery, or targeted therapy at the time of operation The methods of the present disclosure are designed to be done in a very rapid fashion, in order to enable intraoperative decision making and guidance of subsequent operative steps, including resection of the detected or graded tumor or lesion. These methods are capable of being performed within 30 minutes of the completion of DNA extraction. With rapid extraction techniques allowing extraction of sample DNA within 15 minutes, the result is a method which is capable of providing sensitive results to the surgeon within 45 minutes, thus allowing the surgeon to act on the results within an intraoperative timeframe.

The methods of the present disclosure are also very sensitive at detection of single nucleotide polymorphisms and somatic variants. Through the use of optimized probes and wild-type blocking oligonucleotides, we show detection as low as 0.1% mutant allele fraction in an intraoperative timeframe.

A further application of the methods described herein takes advantage of their high sensitivity to detect single nucleotide polymorphisms or somatic variants in cell free circulating DNA, such as detection of cell free circulating tumor DNA, which may be present in blood or serum are very low levels not detectable by other means.

In many applications of the methods described herein, the method can include calculating tumor burden or tumor purity in the sample, based on quantitative amount of mutant allele detected.

In many cases, it is based on quantitative amount of mutant allele detected relative to standard curve generated from serial dilutions of control DNA.

Rapid and sensitive molecular characterization by this assay could guide the decision to pursue a maximal upfront resection of gliomas, obviating the need for a staged craniotomy pending final pathologic confirmation. Furthermore, the ability to obtain intraoperative molecular information allows for the future possibility of administering direct intratumoral therapy. Another direct application of this assay would be to quantify the extent of residual disease at the surgical margin and incorporate that information into postoperative oncologic treatment planning. In addition, targeted analysis of IDH1 and TERT promoter mutations with minimal tissue requirement could accurately characterize and stratify glioma subtypes, with potential implications for prognosis and clinical trial design.

In some applications of the methods described herein, the sample from the subject is taken from a concurrent surgical procedure involving the subject and a surgeon, wherein the sample from the subject is obtained in rapid fashion, and results of the method are available to the surgeon to guide further treatment of the subject during the surgical procedure.

In some cases, the method can include subsequent resection of a glioma tumor in the subject.

In some cases, the method can include inserting a therapeutic drug-coated wafer into a central cavity of a tumor in the subject.

These methods for detecting single nucleotide somatic variants can be applied as non-invasive biomarker detection methods for monitoring disease progression and treatment response. Identification of circulating cell free tumor DNA with digital PCR has been a widely applied to a variety of tumor subtypes (C. Bettegowda et al., Sci. Transl. Med. 6, 224ra24 (2014); S.-J. Dawson et al., N. Engl. J. Med. 368, 1199-1209 (2013)). One challenge of detecting cell free mutant alleles is the fragmented nature of circulating tumor DNA, necessitating short PCR amplicons to capture these fragments. A second challenge is the low abundance of tumor-specific alleles circulating as cell free DNA fragments, which is addressed by the ability of the present methods to detect in cell free DNA fragments variants such as TERT C228T or TERT C250T. The methods can be used with as little as 25 pg starting genomic material to detect circulating cell free DNA variant in a patient at any stage in the patient's disease. The present methods can be used to detect circulating cell free DNA variant at a later timepoint post-treatment, supporting determination of disease progression and/or clinical treatment response.

Other Uses

The diagnosis, prognosis and assessment of therapeutic treatment of diseases or disorders can be facilitated by the sensitive detection of single nucleotide polymorphisms or somatic variants using the systems and methods described herein. For diagnostic purposes, the methods and systems can be used to detect a mutant allele or alleles in one or more target nucleic acids. By quantifying the amount of the mutant allele(s) in a sample relative to a control, the likelihood of the presence of the disease or disorder can be determined for a subject. Prognosis can be determined by detecting a mutant allele or alleles in one or more target nucleic acids, and. quantifying the amount of the mutant allele(s) in a sample relative to a control. In this way, the prognosis of a disease or disorder can be determined for a subject. In addition, the assessment of a targeted therapeutic approach can be facilitated by detecting a mutant allele or alleles in one or more target nucleic acids, and quantifying the amount of the mutant allele(s) in a sample relative to a control. In this way, the effectiveness of the targeted treatment on the disease or disorder can be determined.

Melanoma

In certain embodiments, the methods and systems described herein are used to detect or diagnose melanoma. In certain embodiments, the methods and systems described herein are used to detect an increased risk of the presence of melanoma. In certain embodiments, mutations in BRAF, NRAS and/or TERT are used to detect, diagnose or detect an increased risk of the presence of melanoma. In some embodiments, mutations in BRAF, NRAS and/or TERT are detected in cell free DNA. This cell free DNA can be isolated from blood, serum or plasma. Mutations in BRAF, NRAS and/or TERT can also be detected in tissue samples. In certain embodiments, the detection of mutation in these genes can be used prognostic indicators for melanoma. In other embodiments, mutations in these genes can be used for assessing a therapeutic response to melanoma. In certain embodiments, the mutation in NRAS is one that leads to a Q61R or Q61K mutation in the protein encoded by this gene. In certain embodiments, the mutation in TERT to the promoter of this gene.

In certain embodiments, the methods and systems can take advantage of the occurrence of somatic single nucleotide variants targeting the Q61 codon of NRAS occurs in 10-25% of cutaneous melanoma (Tsao, H., et al. (2012); Genes Dev., 26:1131-1155), and thereby facilitate the detection of Q61 variants for the diagnosis of melanoma. Because patients undergoing therapies targeting mutant BRAF have been found to develop resistance through mechanisms that result in mutations to the NRAS Q61 codon (Van Allen E, et al. (2014); Can Disc., 4:94), their prognosis can be facilitated by applying the methods and systems herein to detection of NRAS Q61 variation. Furthermore, since patients with NRAS-mutant melanoma have a better response to immunotherapy than those with mutant BRAF (Johnson, D B, et al. (2015); Cancer Immunol Res., 3(3): 288-295), the detection of single nucleotide or somatic variants in NRAS and BRAF using the methods and systems herein can facilitate the prognosis and monitoring of efficacy of targeted treatment in melanoma patients.

In certain embodiments, the methods and systems described herein are used to detect or diagnose uveal melanoma. In certain embodiments, the methods and systems described herein are used to detect an increased risk of the presence of uveal melanoma. In certain embodiments, mutations in BRAF, GNAQ, GNA11 and/or TERT are used to detect, diagnose or detect an increased risk of the presence of uveal melanoma. In some embodiments, mutations in BRAF, GNAQ, GNA11 and/or TERT are detected in cell free DNA. This cell free DNA can be isolated from blood, serum or plasma. Mutations in BRAF, GNAQ, GNA11 and/or TERT can also be detected in tissue samples. In certain embodiments, the detection of mutation in these genes can be used prognostic indicators for uveal melanoma. In other embodiments, mutations in these genes can be used for assessing a therapeutic response to uveal melanoma. In certain embodiments, the mutation in GNAQ is one that leads to a R183Q, Q209L or Q209P mutation in the protein encoded by this gene. In certain embodiments, the mutation in GNA11 is one that leads to a Q209L mutation in the protein encoded by this gene.

Somatic single nucleotide variants in GNAQ or GNA11 are found in over 80% of uveal melanomas. These variants lead to activation of the MAPK pathway (Chen X., et al., (2014); Oncogene, 33:4724-4734, Van Raamsdonk C D, et al (2010); N Engl J Med, 363:2191-2199, Van Raamsdonk C D, et al. (2009); Nature 457:599-602). Inhibition of the MAPK pathway can lead to improved progression free survival (Carvajal R D, et al. (2014); Jama 311:2397-2405). Predicting response is hindered, however, by the location of the tumor. Diagnosis of uveal melanoma could thus be improved by monitoring, for example. the blood of patients with uveal melanoma by the detection of alterations to GNAQ and/or GNA11 according to the methods herein.

Diffuse Intrinsic Pontine Glioma and H3F3A

In certain embodiments, the methods and systems described herein are used to detect or diffuse intrinsic pontine glioma (DIPG). In certain embodiments, the methods and systems described herein are used to detect an increased risk of the presence of DIPG. In certain embodiments, mutations in H3F3A are used to detect, diagnose or detect an increased risk of the presence of DIPG. In some embodiments, mutations in H3F3A are detected in cell free DNA. This cell free DNA can be isolated from blood, serum, plasma, or cerebrospinal fluid. Mutations in H3F3A can also be detected in tissue samples. In certain embodiments, the detection of mutation in these genes can be used prognostic indicators for DIPG. In other embodiments, mutations in these genes can be used for assessing a therapeutic response to DIPG. In certain embodiments, the mutation in H3F3A is one that leads to a K27M or G34R mutation in the protein encoded by this gene.

Diffuse intrinsic pontine gliomas (DIPG) are diffusely infiltrative malignant glial neoplasms that arise in the brainstem during childhood (Panditharatna E., et al. (2015); Cancer Genet. 208, 367-373). These tumors are highly aggressive and ultimately fatal. More than 70% of diffuse intrinsic pontine glioma, one-third of pediatric glioblastoma and nearly 20% of pediatric anaplastic astrocytoma have recently been found to harbor recurrent mutations in H3F3A (Schwartzentruber, J. et al. (2012); Nature 482, 226-231, Wu, G. et al. (2012); Nat. Genet. 44, 251-253). Though there is a growing consensus toward obtaining biopsies of patients with suspected DIPG (Walker, D. A. et. al. (2013); Neurooncology 4, 462-468), The risks of routine brainstem biopsies in children remains concerning. The systems and methods herein, when applied to the sensitive detection of variants of H3F3A, can improve the diagnosis success rate for diffuse gliomas, including DIPGs, especially given that the disease could be diagnosed and monitored in response to targeted therapeutic approaches using small volumes of Cerebrospinal Fluid (CSF). Such a minimally-invasive approach to diagnosis, prognosis and monitoring therapeutic response could significantly improve the management of diffuse gliomas in adults and children.

Research Applications

The skilled artisan will be aware of the many useful further applications of these methods to enable sensitive detection of single nucleotide polymorphisms or somatic variants for research uses. In some cases, the methods herein can also include the experimental validation of genome editing in cell culture or in an animal model.

In further examples, applications of these methods can be used with archival tissue. In some cases, the archival tissue is in a formalin-fixed paraffin embedded sample.

Furthermore, in accordance with the present invention there may be employed conventional molecular biology, microbiology, and recombinant DNA techniques within the skill of the art. Such techniques are explained fully in the literature. See, e.g., Green & Sambrook, *Molecular Cloning: A Laboratory Manual*, Fourth Edition (2012) Cold Spring Harbor Laboratory Press, Cold Spring Harbor, N.Y.; *DNA Cloning: A Practical Approach*, Volumes I and II (D. N. Glover ed. 1985); Oligonucleotide Synthesis (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

The present invention is further illustrated by the following examples which should not be construed as further limiting. The contents of the figures and all references, patents and published patent applications cited throughout this application are expressly incorporated herein by reference for all purposes.

EXAMPLES

The following examples are included to provide those of ordinary skill in the art with a complete disclosure and description of how to make and use the methods and compositions featured in the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Rapid Quantitation of Single Nucleotide Polymorphisms to Identify Glioma Case Report In 2006, a 16-year-old woman presenting with progressive headaches was found to have a non-enhancing left medial temporal lobe lesion on T2-weighted MRI. She had a normal neurologic exam. She underwent an MRI-guided stereotactic biopsy to obtain diagnostic tissue, but four separate frozen section specimens were inconclusive (FIG. 1A). Final neuropathologic analysis noted a mild increase in cellularity, scattered atypical cells, and low Ki-67 proliferation index (less than 1% of cells). These findings were suggestive, but not diagnostic, of an infiltrative diffuse glioma. Given the lack of a definitive diagnosis, she was followed clinically with annual serial imaging and neurologic examination for the following five years without evidence of radiographic changes and was subsequently lost to follow-up. In 2014, she presented with a generalized seizure. An MRI revealed an increase in the extent of the non-enhancing lesion with progression along the medial temporal lobe, extending into the ipsilateral thalamus and crossing the splenium of the corpus callosum. Due to the extent of disease, she underwent a partial resection, with pathology revealing a WHO Grade II oligoastrocytoma with cytological atypia, rare mitoses and an elevated Ki-67 proliferation index of (6.3%). Analysis of the tumor revealed retention of chromosome arms 1p and 19q, MGMT methylation, and IDH1 R132H detected by mutant-specific immunohistochemistry. Based on this new diagnostic information, the patient went on to receive temozolomide chemotherapy.

Methods

To address the challenge of non-diagnostic intraoperative biopsies, we developed a rapid molecular diagnostic method to detect TERT promoter and IDH1 R132H mutations, sensitively and specifically.

Quantitative PCR Methods

Forward and reverse primers for regions of interest in IDH1 and TERT promoter were designed and empirically optimized for an anneal/elongation temperature of 63.5° C. 5' Nuclease probes against mutant alleles and corresponding PNA oligonucleotide blockers against wild-type alleles were designed to detect IDH1 R132 mutations and TERT promoter mutations on chromosome 5 at positions 1,295,228 and 1,295,250 based on human genome reference version 19 (referred to hereafter as TERT C228T or TERT C250T) (FIG. 13). Optimal sensitivity was achieved through the use of two distinct TERT wild-type PNA blocking oligonucleotides designed to these two respective sites. Similarly, 5' Nuclease probes and the PNA wild-type blockers were designed for optimal performance at 63.5° C. for the respective genomic templates.

The primers for IDH1 were 5'-CCGGCTTGTGAGTG-GATGGGTAAAACCT-3' (SEQ ID NO: 29) and 5'-CATT-ATTGCCAACATGACTTACTTGATCCCC-3' (SEQ ID NO: 30) both used at final concentrations of 750 nM. The TaqMan probe for detection of the IDH1 R132H mutation was 250 nM 5'-FAM-AGG+T+C+A+T+CAT+GC-Dab-3' (with the locked nucleic acid being denoted by a preceding+; SEQ ID NO: 36) (Exiqon). The peptide nucleic acid (PNA) probe for blocking wild-type IDH1 amplification was 900 nM 5'-AGGTCGTCATGC-3' (SEQ ID NO: 20) (PNA Bio).

The primers for TERT were 5'-CACGTGCGCAGCAG-GACGCAG-3' (SEQ ID NO: 9) and 5'-CTTCACCTTCCA-GCTCCGCCTC-3' (SEQ ID NO: 10) used at 500 nM. The TaqMan probe for detecting TERT C228T was 250 nM 5'-FAM-CCCAGCCCC+T+TCCGGGCCC-Dab-3' (SEQ ID NO: 15) and TERT C250T is 250 nM 5'-FAM-CCGAC-CCC+T+TCCGGGTCCC-Dab-3' (SEQ ID NO: 16). The PNA probes for blocking amplification of TERT C228 and TERT C250 were 150 nM 5'-CCCAGCCCCTC-CGGGCCC-3' (SEQ ID NO: 11) and 500 nM 5'-CCGAC-CCCTCCGGGTCCC-3' (SEQ ID NO: 12), respectively.

The qPCR reactions were run in 384-well plates on an ABI QuantStudio 6 instrument (Applied Biosystems) in the presence of 60 nM ROX to account for background fluorescence. IDH1 reactions were carried in using ABI Gene-Expression 2X mastermix and TERT were carried out in the presence of KAPA 2G Fast Polymerase buffer A and enhancer to a final concentration of 1×. PCR cycling times were 95° C. for 3 minutes followed by 40-60 cycles at 95° for 10 seconds and 63.5° C. for 20 seconds.

Development and Optimization of Rapid Genotyping Methods

Figure 4A:
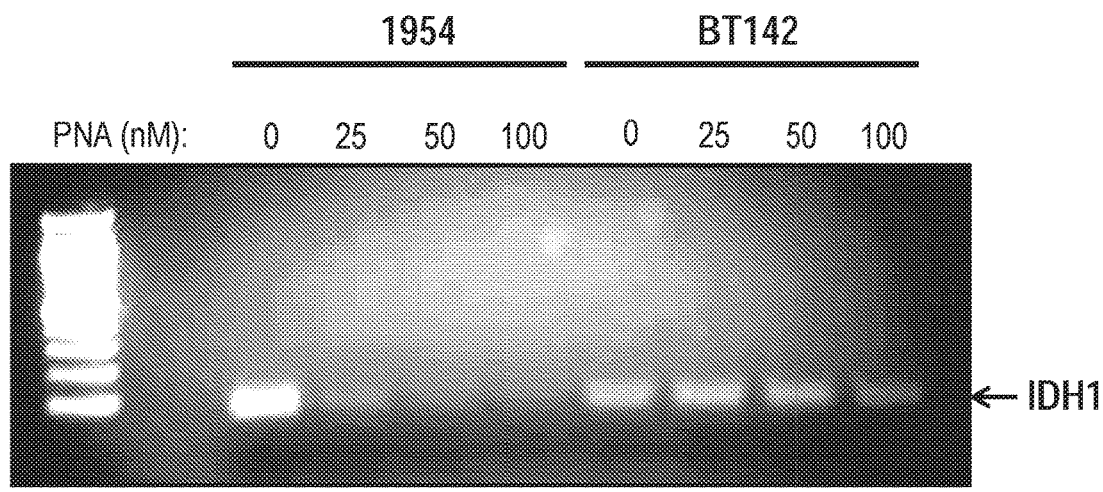
FIG. 4 graphically depicts modified oligonucleotides selectively block exponential PCR amplification of wild-type alleles. Peptide nucleic acid (PNA) oligonucleotides were designed to target wild-type alleles of IDH1 R132 (FIG. 4A), TERT C228 and TERT C250 (FIG. 4B). Genomic extracts were obtained from HCC1143 lymphocytes (wt), wild-type HCC1954 lymphocytes (1954), BT142 primary glioma cell line with hemizygous IDH1 R132H mutation, primary glioma cell line LN428 with TERT C228T mutation and primary glioma cell line LN443 with TERT C250T mutation. PNA oligonucleotides have dose-dependent effects in selectively blocking wild-type allele amplification, while allowing for PCR amplification of mutant alleles.
Figure 4B:
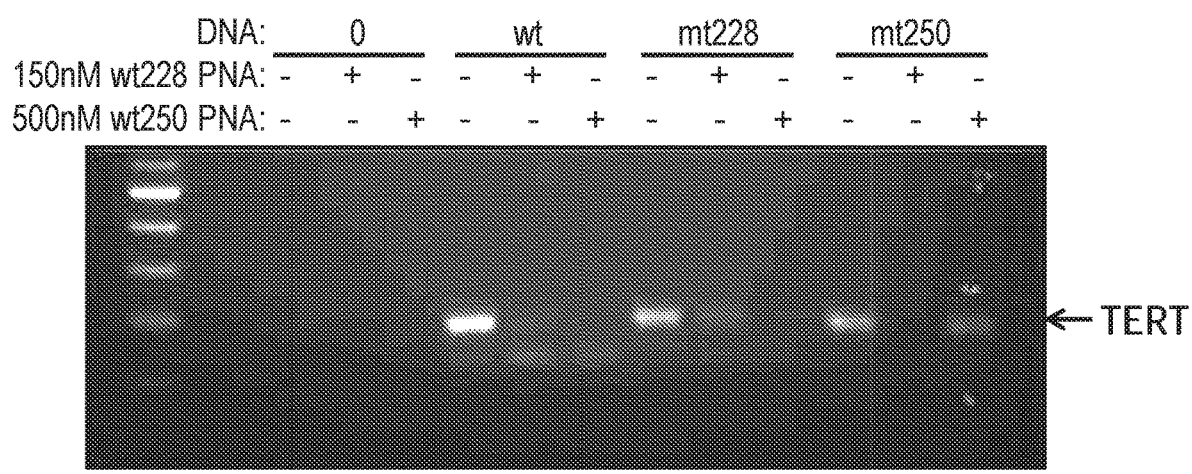
Figure 5B:
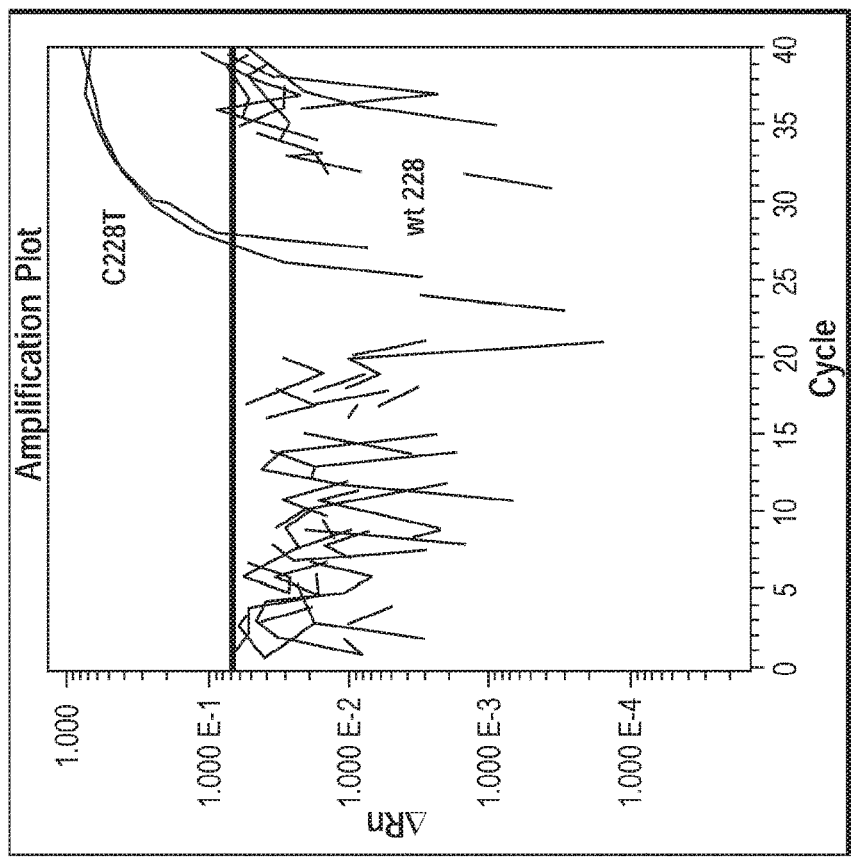
FIG. 5 graphically depicts locked nucleic acid (LNA) probes are specific for detection of mutant alleles. Locked nucleic acid probes were designed for targeting IDH1 R132H (FIG. 5A), TERT C228T (FIG. 5B), or TERT C250T (FIG. 5C). LNA probes selectively detect mutant alleles, but not wild-type (wt) alleles. These experiments were performed in the absence of modified PNA oligonucleotides.
Figure 5A:
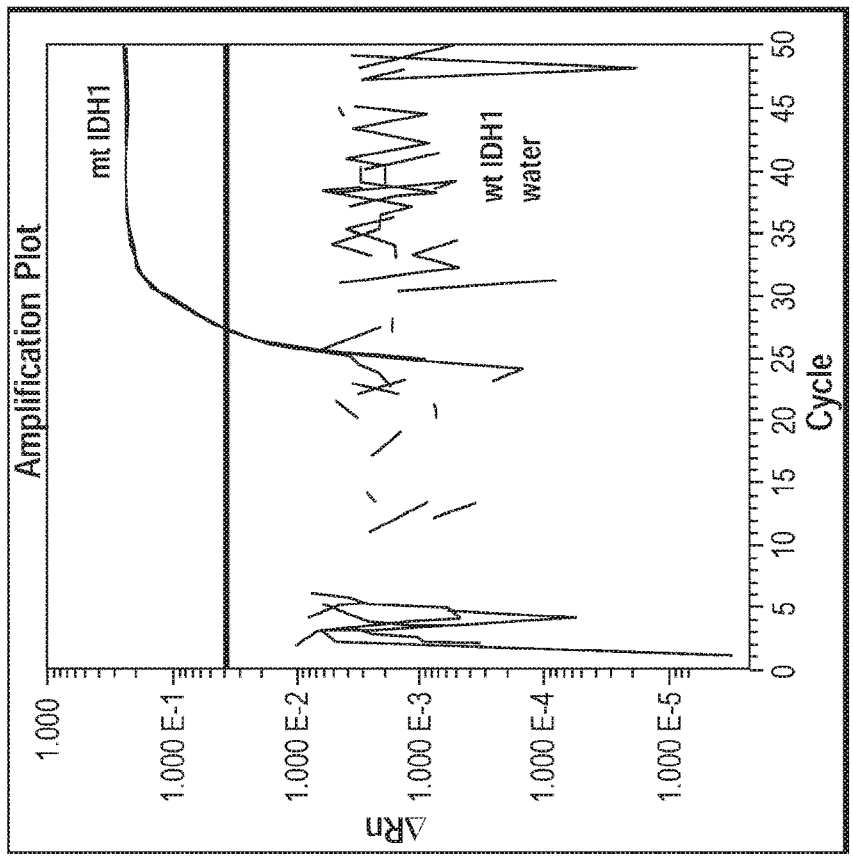
Figure 5C:
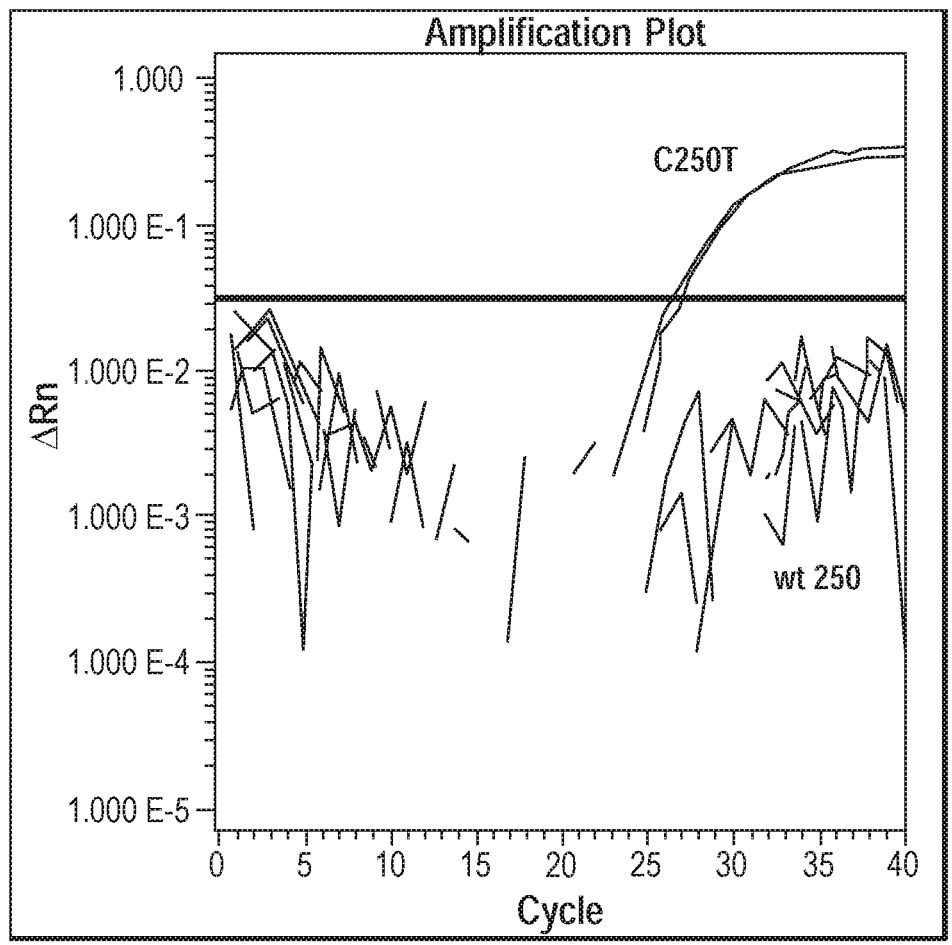
Figure 6A:
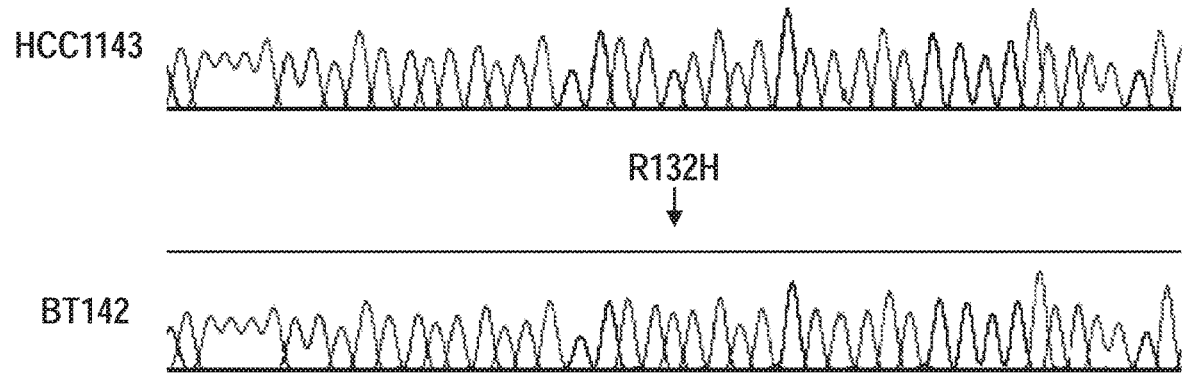
FIG. 6 graphically depicts Sanger sequencing validation of positive and negative control genomic extracts. IDH1 (FIG. 6A) and TERT promoter (FIG. 6B) amplicons were confirmed by Sanger sequencing. Wild-type controls were obtained from cell extracts from HCC1143 lymphocytes. IDH1 R132H mutant genomic extract was obtained from BT142 neurospheres. TERT C228T and TERT C250T controls were obtained from the LN428 and LN443 primary glioma cell lines, respectively. PCR products were generated in the absence of PNA oligonucleotide blockers.
Figure 6B:
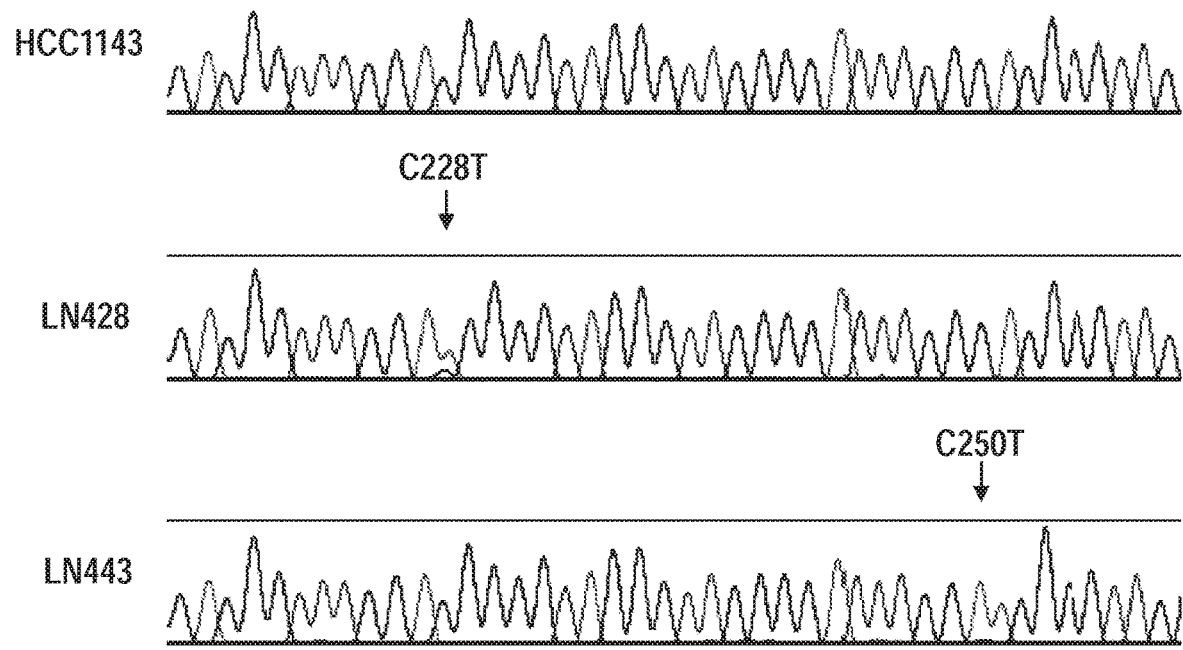
Figure 7C:
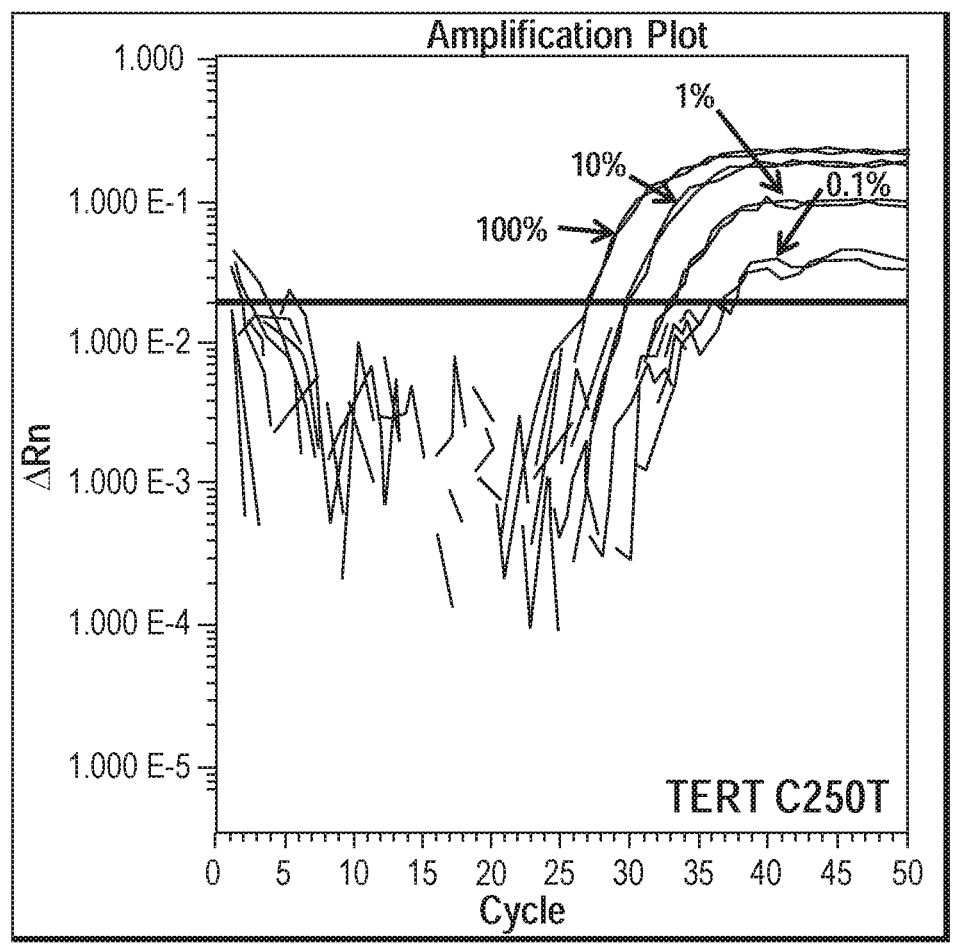
FIG. 7 graphically depicts highly sensitive and specific detection of tumor alleles by the methods disclosed herein. Combination of allele-specific Taqman probes and wild-type allele blockers with modified oligonucleotides allows for sensitive detection of IDH1 R132H (FIG. 7A), TERT C228T (FIG. 7B), and TERT C250T (FIG. 7C) to 0.1% tumor allele fraction. Genomic DNA from BT142, LN428, or LN443 was diluted serially in wild-type genomic extracts from HCC1143 lymphocytes.
Figure 8:
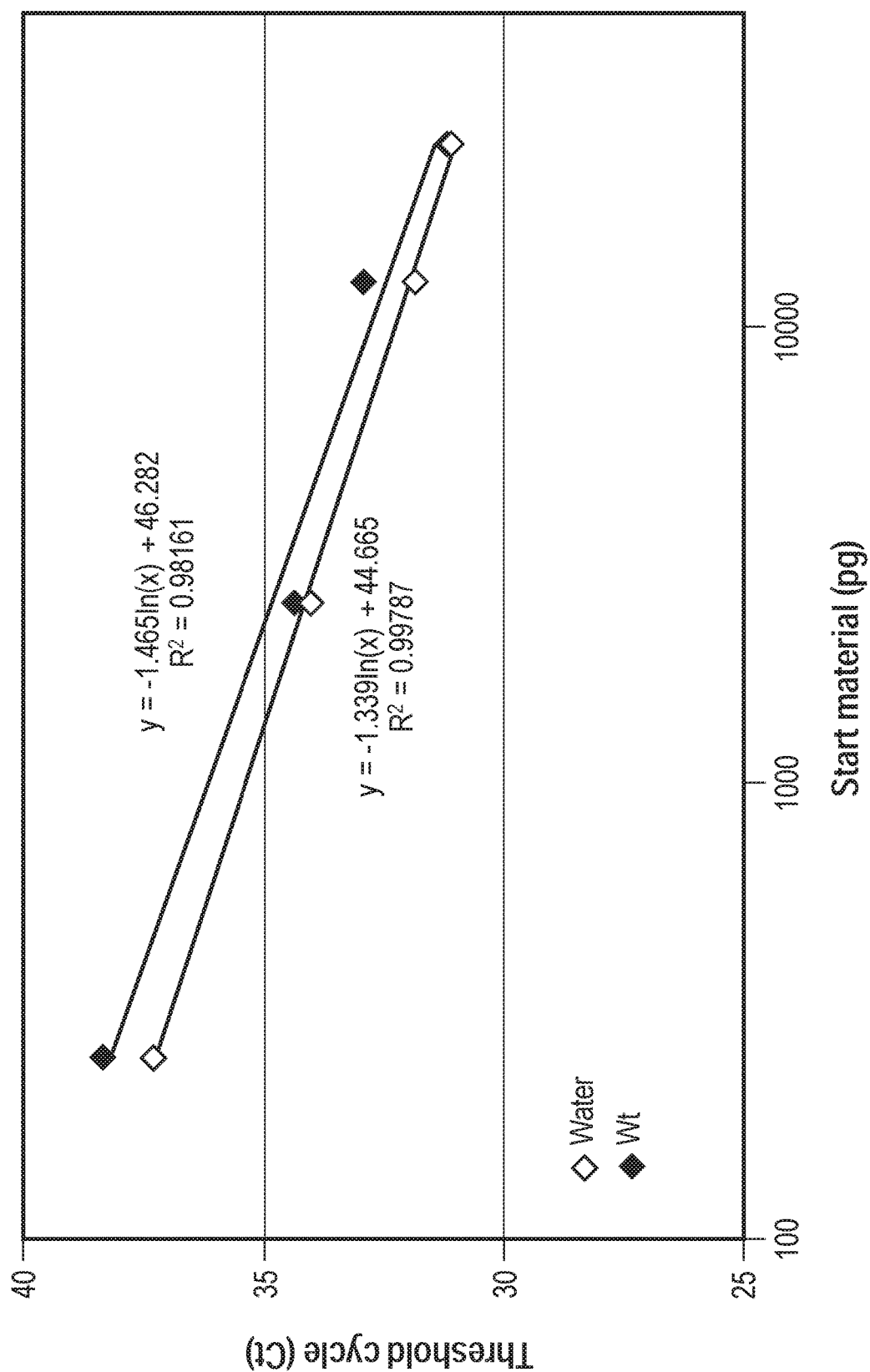
FIG. 8 graphically depicts quantitative analysis allows for gross estimation of tumor purity. The method disclosed herein performed in the presence of modified PNA oligonucleotides allows for gross estimation of tumor purity when tumor genomic extract is serially diluted in wild-type genomic extract (red diamonds, wild-type).

One challenge of detecting mutant alleles in brain biopsies with infrequent tumor cells is competition for PCR reagents by wild-type alleles from surrounding normal cells. To address this, PNA oligonucleotides, which cannot be digested by 5' exonuclease activity or used as a primer for extension by DNA polymerase, were used to block the amplification of wild-type alleles (FIG. 4). At the same time, high mutant allele specificity was achieved through the use of LNAs, where a chemically synthesized ribose moiety stabilized by an additional covalent bond is incorporated into the detection probe in order to optimize hybridization characteristics and minimize non-specific binding to wild-type alleles (FIG. 5). TERT promoter and IDH1 control templates were validated by Sanger sequencing (FIG. 6). The method design allowed for simultaneous parallel detection of IDH1 and TERT promoter mutations. The IDH1 R132H detection probe was labeled with a FAM moiety while the lower frequency R132 detection probes were labeled with a MAX moiety to allow for simultaneous detection of canonical and non-canonical IDH1 alterations. In these optimized methods, IDH1 R132H, R132S, R132C, R132G, R132L, TERT C228T, or TERT C250T could be detected in samples harboring as low as 0.1% mutant allele fraction (FIG. 7). Reactions contained on average 25 ng of genomic input, however signal was detected from as low as 60 pg of input material as quantified by PicoGreen (Invitrogen). Estimation of tumor purity was extrapolated from standard curves generated from serial dilutions of mutant specific control DNAs (FIG. 8). For validation by next generation sequencing, PCR amplicons were generated for these regions and subjected to high depth sequencing by MiSeq (Illumina). Sequences were aligned by standard methods and were manually reviewed by Integrated Genome Viewer with allelic fraction threshold of 5%.

Tumor Specimens

Archived glioma specimens and intraoperative specimens were obtained under approval of the Institutional Review Boards at Dana-Farber Cancer Institute and Massachusetts General Hospital, respectively. Archived FFPE cases that were suggestive of oligodendroglioma by histological examination also had been analyzed for deletion of chromosome 1p and 19q by fluorescence in situ hybridization (FISH) or array comparative genomic hybridization (aCGH).

FFPE specimens were extracted using Qiagen QIAamp FFPE kit using manufacturer's recommended protocol. Intraoperative or fresh tissue specimens were extracted using Invitrogen ChargeSwitch magnetic bead isolation system following manufacturer's protocol using the following modifications: increased proteinase K concentrations, shortened incubation at 55° C., and elution in lower buffer volumes.

Circulating cell free DNA was isolated from 5 ml of fresh peripheral blood using the Qiagen Circulating Nucleic Acid Isolation kit following manufacturer's protocol and quantified by PicoGreen and visualized by Agilent BioAnalyzer.

Control Genomic Templates

The BT142 cell line (ATCC), which is hemizygous for the IDH1 R132H mutation (Luchman H A, et al., Neuro-Oncol 2013; 15(8):979-80) was grown under standard conditions. The TERT C228T and TERT C250T control templates were generated from established glioma cell lines LN428 and LN443, respectively. Wild-type DNA was isolated from the normal lymphoblastic cell line HCC1954 (ATCC).

Detection of Glioma in Previously Inconclusive Biopsy

Figure 1B:
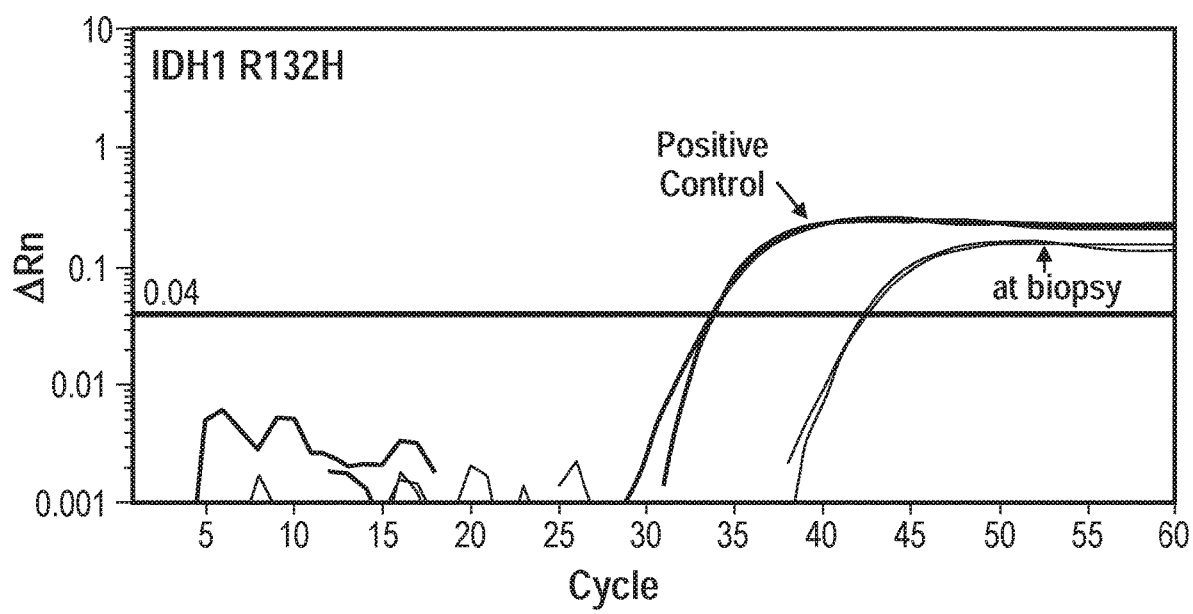
FIG. 1B shows results of the method disclosed herein performed on 600 pg of non-diagnostic biopsy revealing the presence of IDH1 R132H mutation with estimated tumor purity of 11% (FIG. 10), consistent with the clinical diagnosis of diffuse glioma.
Figure 1C:
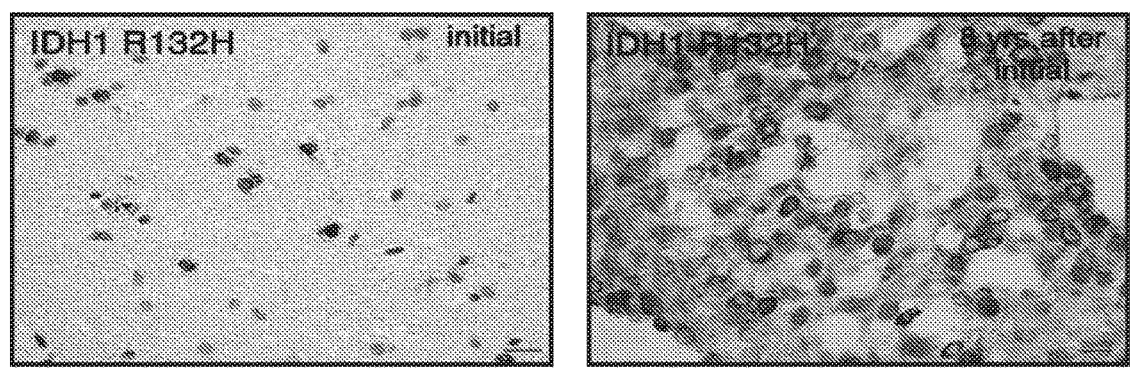
FIG. 1C shows retrospective Immunohistochemistry (IHC) performed against IDH1 R132H revealed rare tumor cells in initial biopsy (left panel) compared to specimen obtained eight years later (right panel). Scale bar is 20 μm.
Figure 9:
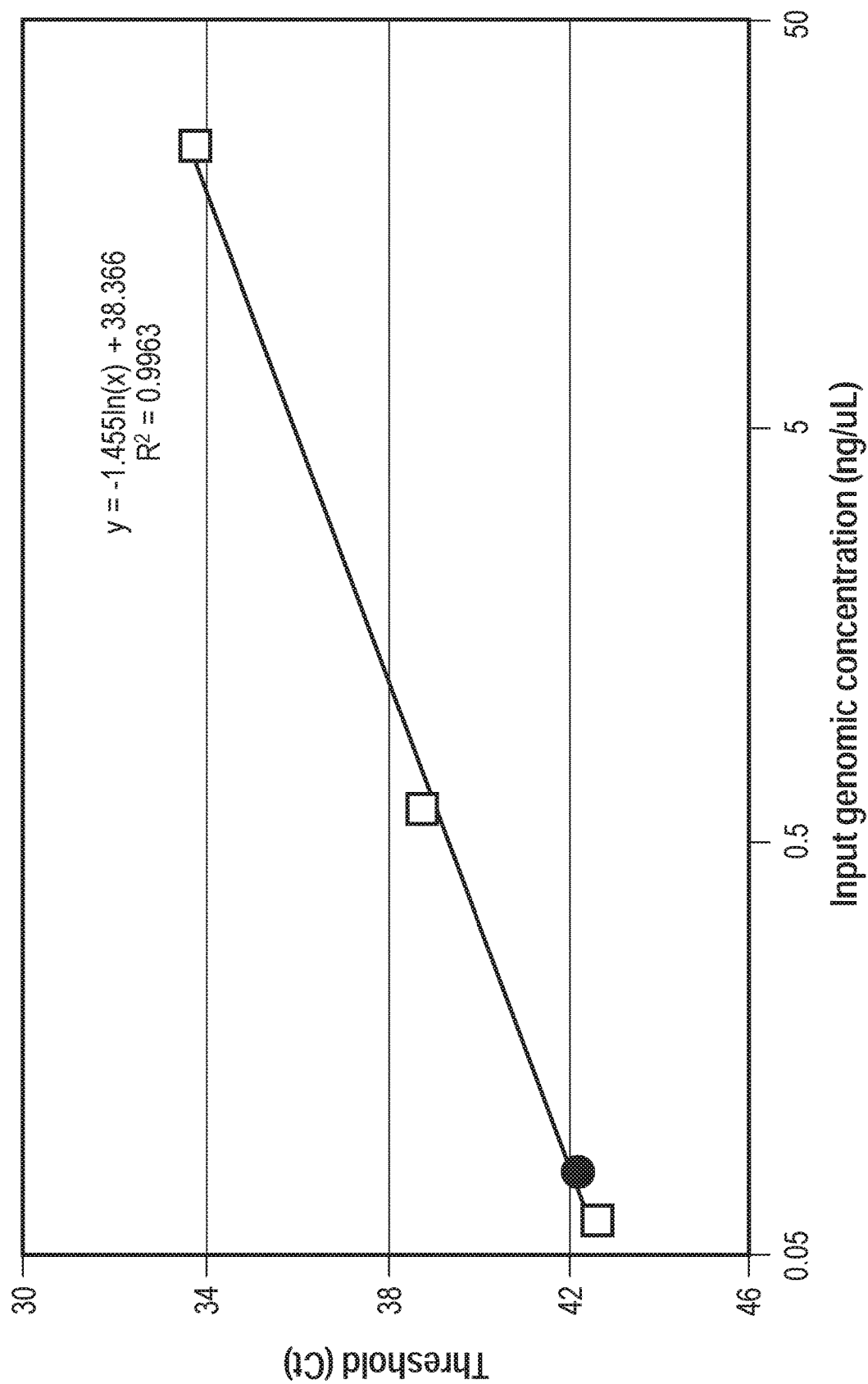
FIG. 9 graphically depicts previously inconclusive biopsy specimen with estimated tumor purity of 11% by the method disclosed herein. Standard curve was generated by serial dilution of genomic extract containing IDH1 R132H mutant alleles with wild-type genomic extract. The IDH1 R132H detection signal crossed threshold at 42.5 cycles (red dot) which corresponds with ~64 pg starting mutant genomic extract (11% of the starting material of 600 pg).

To determine whether we could detect glioma-defining mutations in a non-diagnostic biopsy, we obtained a small FFPE fragment of the above-described patient's 2006 inconclusive specimen. Despite a DNA concentration of 600 pg/uL, using the method disclosed herein we were able to detect IDH1 R132H but no TERT promoter mutation, consistent with the patient's ultimate diagnosis of oligoastrocytoma (FIG. 1B). Using serial dilution curves, we estimate that this specimen contained only 11% tumor cells (FIG. 9). Consistent with result of the method disclosed herein, retrospective IHC analysis of the 2006 biopsy confirmed that rare infiltrative tumor cells were positive for IDH1 R132H (FIG. 1C). Of course current neuropathology protocols, including IHC for IDH1 R132H, could have similarly established the diagnosis of grade II diffuse glioma post-operatively (Camelo-Piragua S, et al., Acta Neuropathol (Berl) 2010; 119(4):509-11; Anderson M D, et al., Neuro-Oncol 2013; 15(7):811-3). However, definitive resection following final pathology would require a second craniotomy. As this case highlights the hesitation to resect lesions that cannot be definitively diagnosed as infiltrative glioma, we asked whether sensitive and rapid molecular characterization of both IDH1 and the TERT promoter could provide intraoperative clarification of non-diagnostic neurosurgical biopsies.

Application of the Method to Intraoperative Glioma Characterization

Figure 2A:
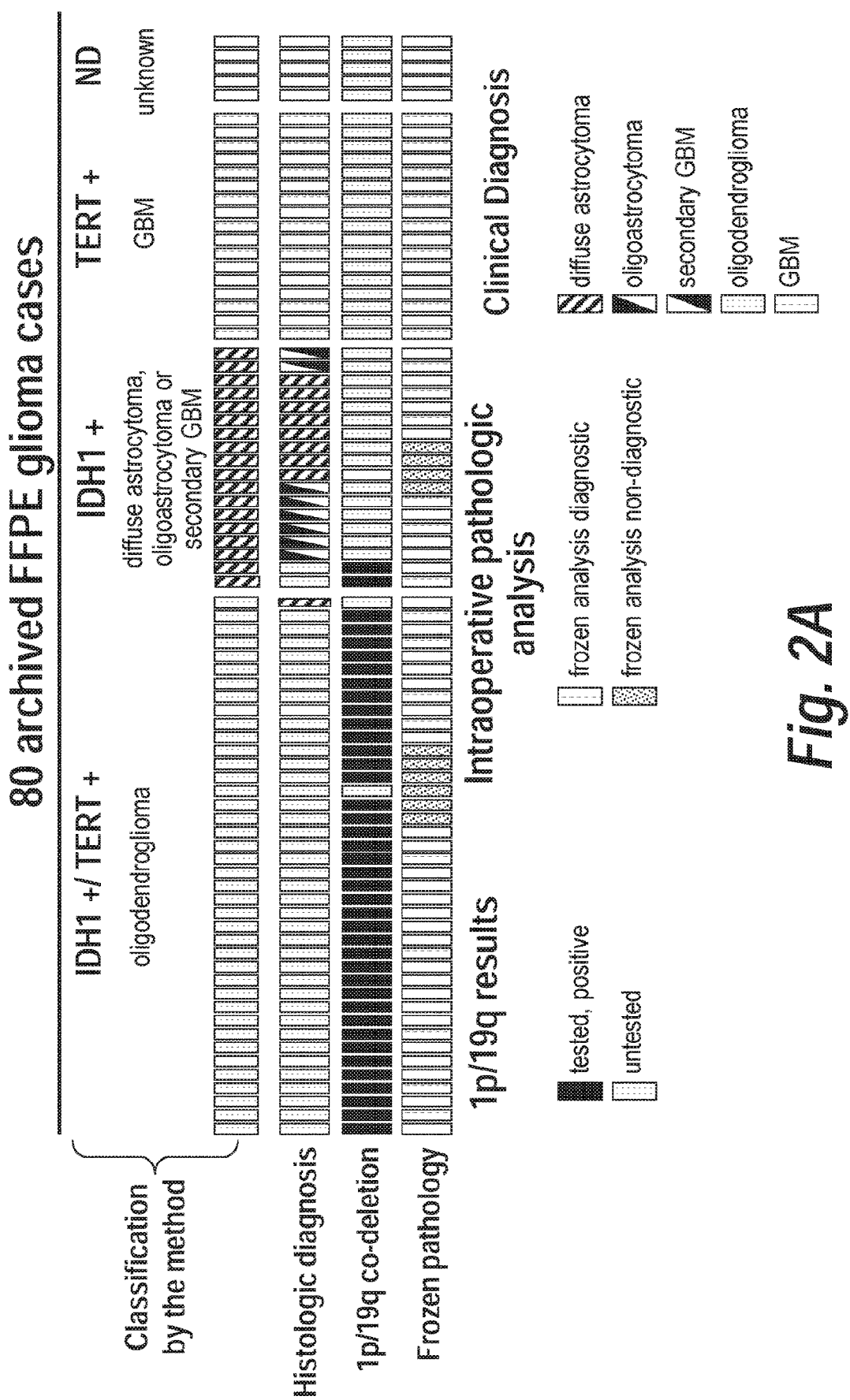
FIG. 2A shows a plot depicting assessment of mutations in IDH1, and TERT in 80 archived glioma cases. Glioma characterization according to the method disclosed herein is based on the presence, absence or co-occurrence of IDH1 and TERT. Second row represents final conventional neuropathologic diagnosis of each case demonstrating concordance with the method disclosed herein. Third row represents clinical assessment of chromosome 1p/19p deletion by FISH or aCGH and is demonstrated in black if tested positive and brown if untested. Bottom row illustrates that intraoperative frozen section analysis was diagnostic (purple) in 22/22 GBM, but inconclusive (pink) in 10/58 diffuse gliomas. The five specimens for which TERT promoter mutations and IDH1 R132H were not detected (ND) by the method disclosed herein were all diagnosed histopathologically as GBM.
Figure 10:
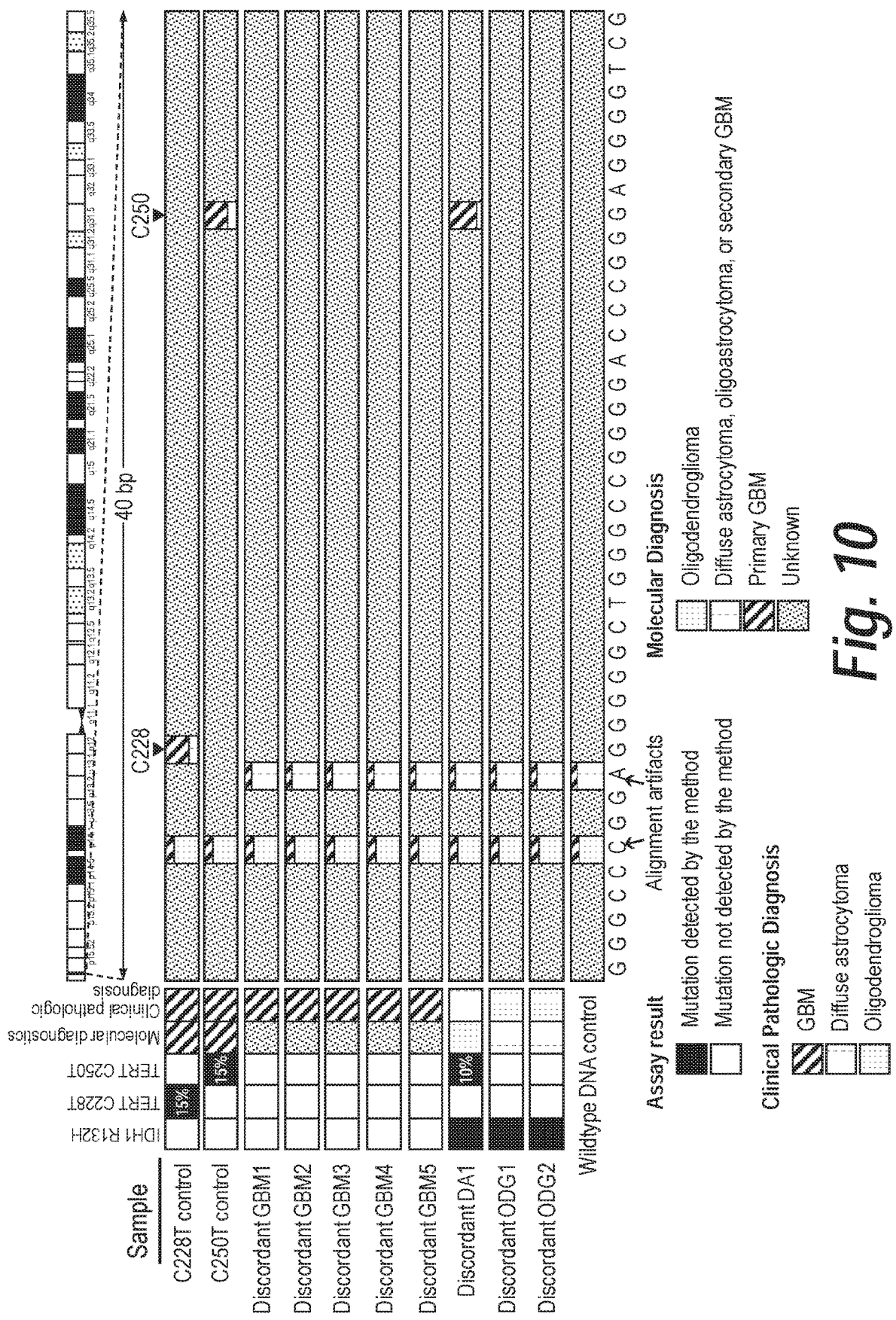
FIG. 10 graphically depicts TERT promoter amplicon characterization by deep sequencing in non-scoring and discordant samples noted in FIG. 2A reveals accurate targeted genotyping by the method disclosed herein. PCR amplicons of the TERT promoter were generated in the samples that were discordant between molecular characterization and clinical pathologic diagnosis and subjected to high depth sequencing (mean depth 250,000×). Positive controls for TERT C228T and TERT C250T were also run in parallel. Fraction of mutant alleles detected by high depth sequencing is displayed in white text within respective TERT mutations. The TERT C250T mutation was observed at an allelic fraction of ~10% by MiSeq in the one sample that was characterized as diffuse astrocytoma, but noted to have a co-mutation of IDH1 and TERT C250T by the method disclosed herein. The other seven samples in which no TERT promoter mutations were observed were also wild-type by high depth sequencing of the amplicon.
Figure 11:
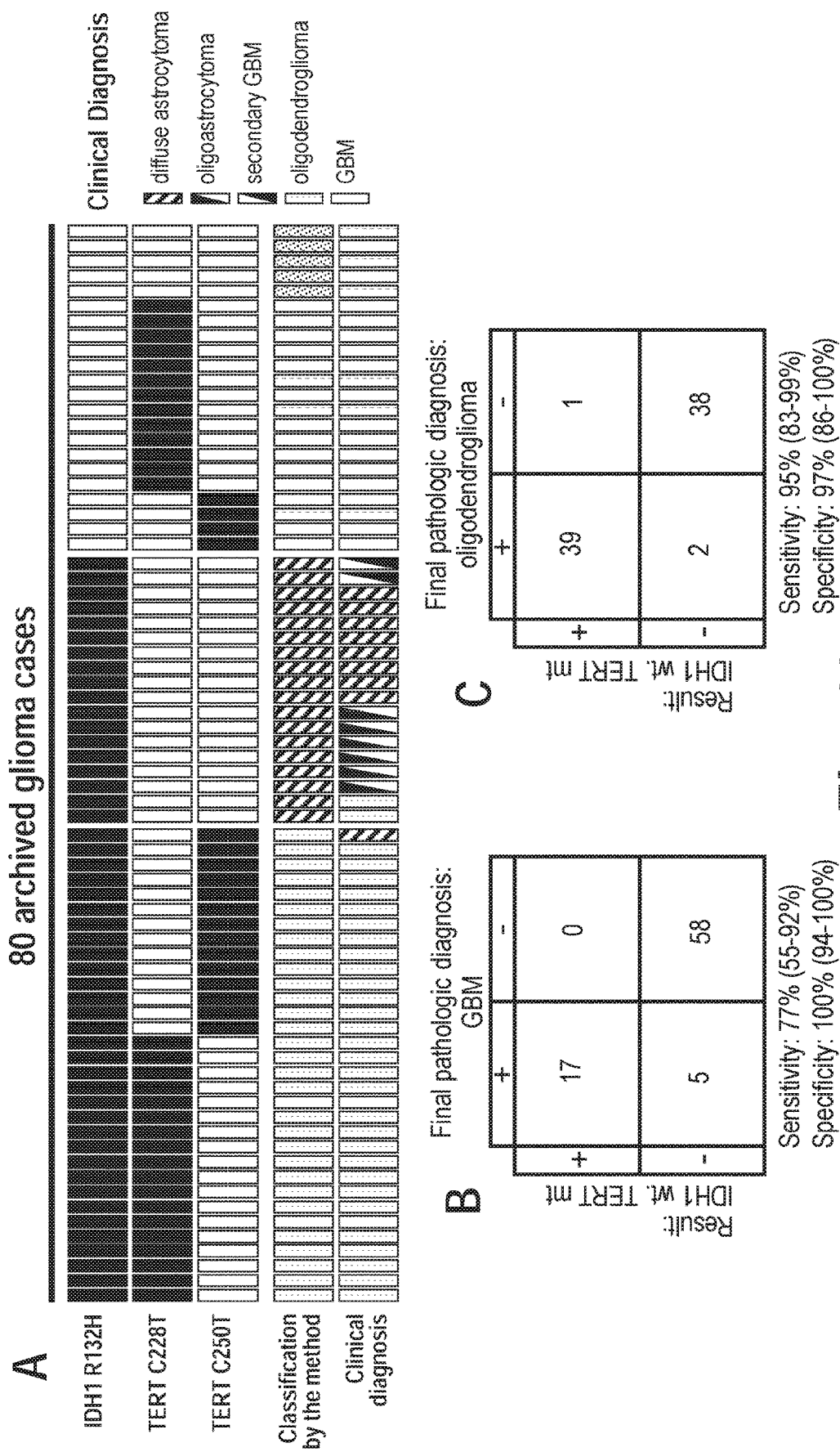
FIG. 11 graphically depicts sensitivity and specificity analysis of results compared to final pathologic diagnosis.

We first sought to validate these methods' ability to detect IDH1 and TERT promoter mutations simultaneously across a range of clinically annotated gliomas (Arita H, et al., Acta Neuropathol (Berl) 2013; 126(2):267-76; Killela P J, et al., Proc Natl Acad Sci USA 2013; 110(15):6021-6; Nonoguchi N, et al., Acta Neuropathol (Berl) 2013; 126(6):931-7). We therefore performed a blinded comparison between molecular characterization based on the method disclosed herein, pathologic diagnoses and DNA sequencing analyses from 80 FFPE archival glioma samples (Cryan J B, et al., Oncotarget 2014). In order to allow for subsequent validation using IHC for IDH1 R132H mutation, tumors with IDH2 or non-R132H IDH1 mutations were excluded from this analysis. Across this group of gliomas, the method disclosed herein was able to detect every tumor with an IDH1 mutation (58/58 samples), as confirmed by IDH1 R132H IHC. Though there is no clinical test to confirm mutations in the TERT promoter, concurrent IDH1 and TERT promoter mutations detected by the method disclosed herein accurately predicted oligodendrogliomas in 38/40 cases with known 1p/19q co-deletion (Killela P J, et al., Proc Natl Acad Sci USA 2013; 110(15):6021-6; Chan A K-Y, et al., Mod Pathol Off J U S Can Acad Pathol Inc 2014). In addition, TERT promoter mutations without an IDH1 mutation were detected in 17/22 GBM, a frequency consistent with prior reports (Killela P J, et al., Proc Natl Acad Sci USA 2013; 110(15):6021-6; Nonoguchi N, et al., Acta Neuropathol (Berl) 2013; 126(6):931-7; Koelsche C, et al., Acta Neuropathol (Berl) 2013; 126(6):907-15). To confirm mutation status in the eight discordant cases, these tumors were additionally analyzed at the TERT promoter by high depth next generation sequencing to a mean of 250,000×coverage (FIG. 10). In each case, high depth sequencing was concordant with the method disclosed herein, demonstrating the accuracy of these methods. The correlation between molecular characterization based on the method disclosed herein and final pathologic diagnosis of oligodendrogliomas, diffuse astrocytomas, oligoastrocytomas and secondary glioblastomas in this series of 80 cases revealed 100% sensitivity (94-100%, 95% confidence interval) and 100% specificity (84-100%, confidence interval) (FIG. 2A, FIG. 11).

Figure 2B:
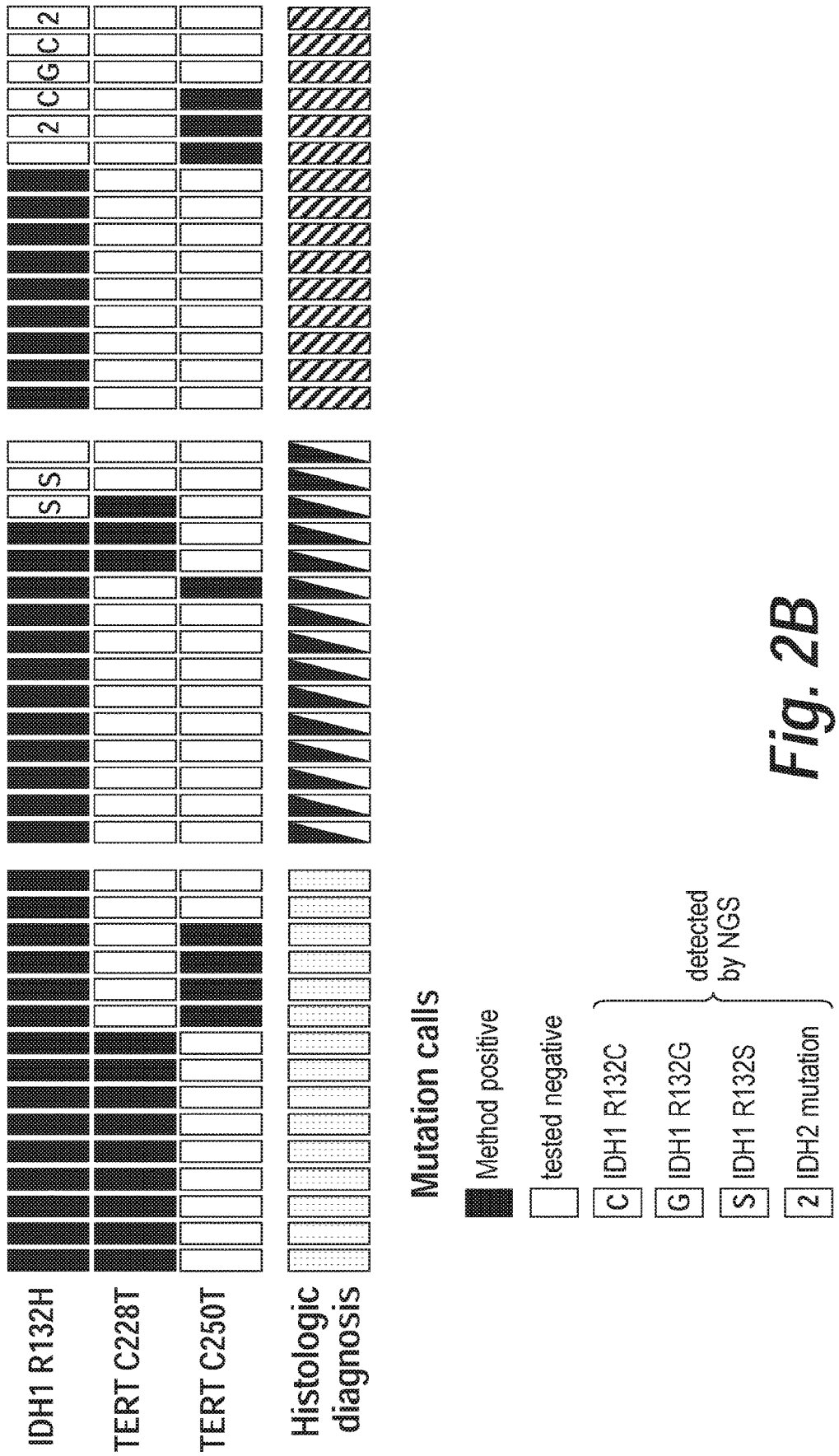
FIG. 2B depicts the validation of the method disclosed herein on archived frozen WHO grade II oligodendrogliomas, oligoastrocytomas, and astrocytomas revealed presence of IDH1 R132H or TERT promoter mutations in 39/44 specimens. The samples were validated by targeted high depth sequencing of these genes. All but one of those cases that did not score by the method disclosed herein were found to have alternative IDH1 and IDH2 mutations.
Figure 2C:
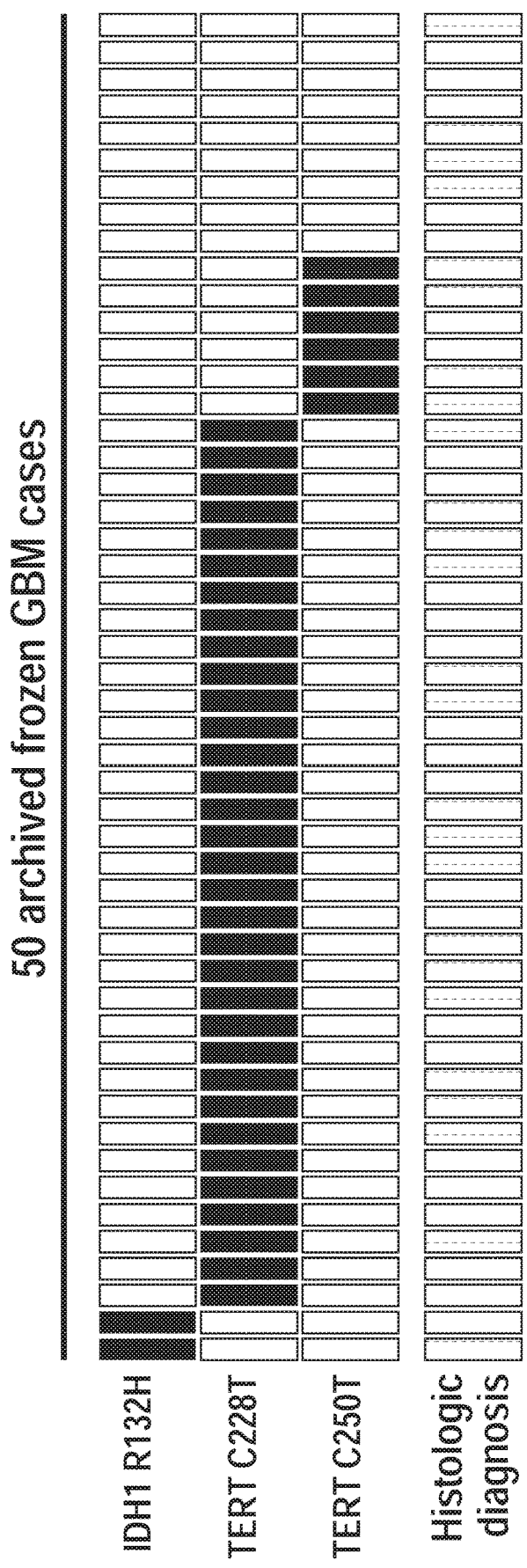
FIG. 2C depicts assessment of false positive rate in third cohort representing 50 frozen GBM specimens. Two samples were noted by the method disclosed hereinto have IDH1 R132H and 39 samples were noted to have either TERT C228T or TERT C250T. The prevalence of non-scoring specimens in this cohort is the similar to the ratio of non-scoring GBM specimens in FIG. 2A (p>0.05 by Fisher's exact test).

Of note, review of the frozen section diagnoses in the FFPE cohort revealed that while an intraoperative diagnosis had been made in 22/22 high grade gliomas, 10/58 diffuse gliomas were not diagnosed definitively at the time of intraoperative histologic examination. Retrospective central neuropathology review confirmed that seven of these frozen section preparations were inconclusive (FIG. 2A). This underscores the potential value of molecular characterization to assist in establishing an intraoperative diagnosis, and led us to evaluate the method disclosed herein in a second validation cohort of 44 archived frozen WHO grade II diffuse gliomas. We were able to detect either IDH1 R132H or TERT promoter mutations C228T or C250T in 39/44 frozen diffuse glioma specimens (FIG. 2B). Four of the five cases that did not score by the method disclosed herein were found to have alternative IDH1/2 mutations by targeted high-depth sequencing. To further explore the possible false positive rate associated with the method disclosed herein, we analyzed 50 frozen GBM specimens (FIG. 2C). Similar to the frequency noted in the FFPE cohort, 39 GBM specimens were positive for TERT C228T or TERT C250T and only 2 were found to have an IDH1 R132H mutation by the method disclosed herein. Furthermore, these 50 GBM cases were subjected to targeted high-depth sequencing which confirmed the presence of the two IDH1 mutations detected by the method disclosed herein, consistent with a zero false positive rate in this cohort.

Figures 11, 12:
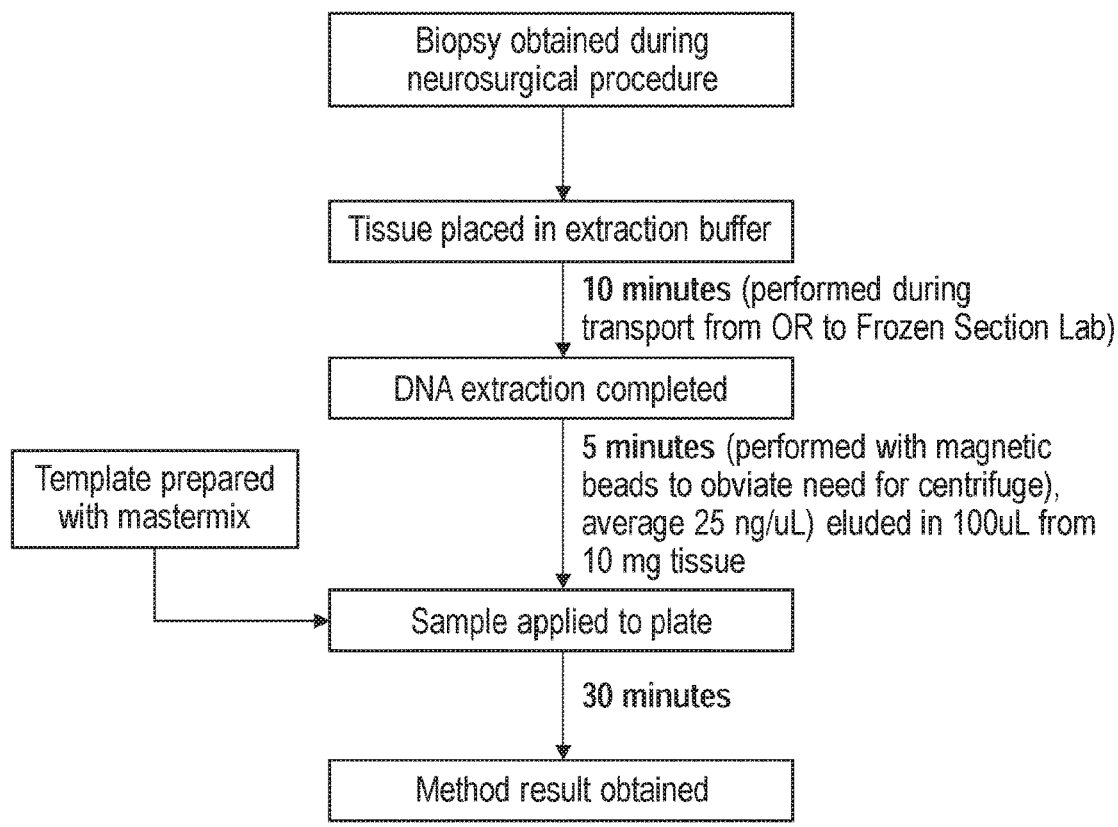
FIG. 12 graphically depicts a proposed workflow of intraoperative analysis of biopsy specimen. Specimen is immediately placed in lysis buffer and incubated at 55° C. en route to pathology lab. DNA extraction is completed with magnetic beads. This sample is applied to a plate already containing the optimized mastermix to detect IDH1 R132H, TERT C228T or TERT C250T with respective positive controls. The rapid qPCR protocol allows for detection of these mutant alleles within 30 minutes.

Having validated the method disclosed herein on a range of archived glioma specimens, we next tested whether these methods could be used in an intraoperative timeframe to detect mutant alleles during glioma surgery. Using intraoperative tissue specimens from five different procedures, the method disclosed herein was able to detect glioma-specific somatic single nucleotide variants (sSNV) in IDH1 or the TERT promoter within 45 minutes of tissue acquisition (FIG. 12). To illustrate how this workflow could ultimately be applied in a clinical setting, we present two additional cases in which this method could have provided intraoperative molecular characterization (FIG. 3A-B). The first case illustrates the ability to detect TERT C228T in a GBM (FIG. 3A) within an intraoperative timeframe. The second patient had a frozen section diagnosis of GBM; however, the method disclosed herein detected an IDH1 R132H mutation and no TERT promoter mutation, which would also be consistent with WHO Grade II-III glioma (FIG. 3B). Indeed, the pathologic assessment from the permanent specimen agreed with the analysis by the method disclosed herein and ultimately concluded that the tumor was an anaplastic oligoastrocytoma. These cases demonstrate that the method disclosed herein can provide molecular characterization, accurately facilitating pathologic diagnosis in an intraoperative timeframe.

Figures 1, 14A:
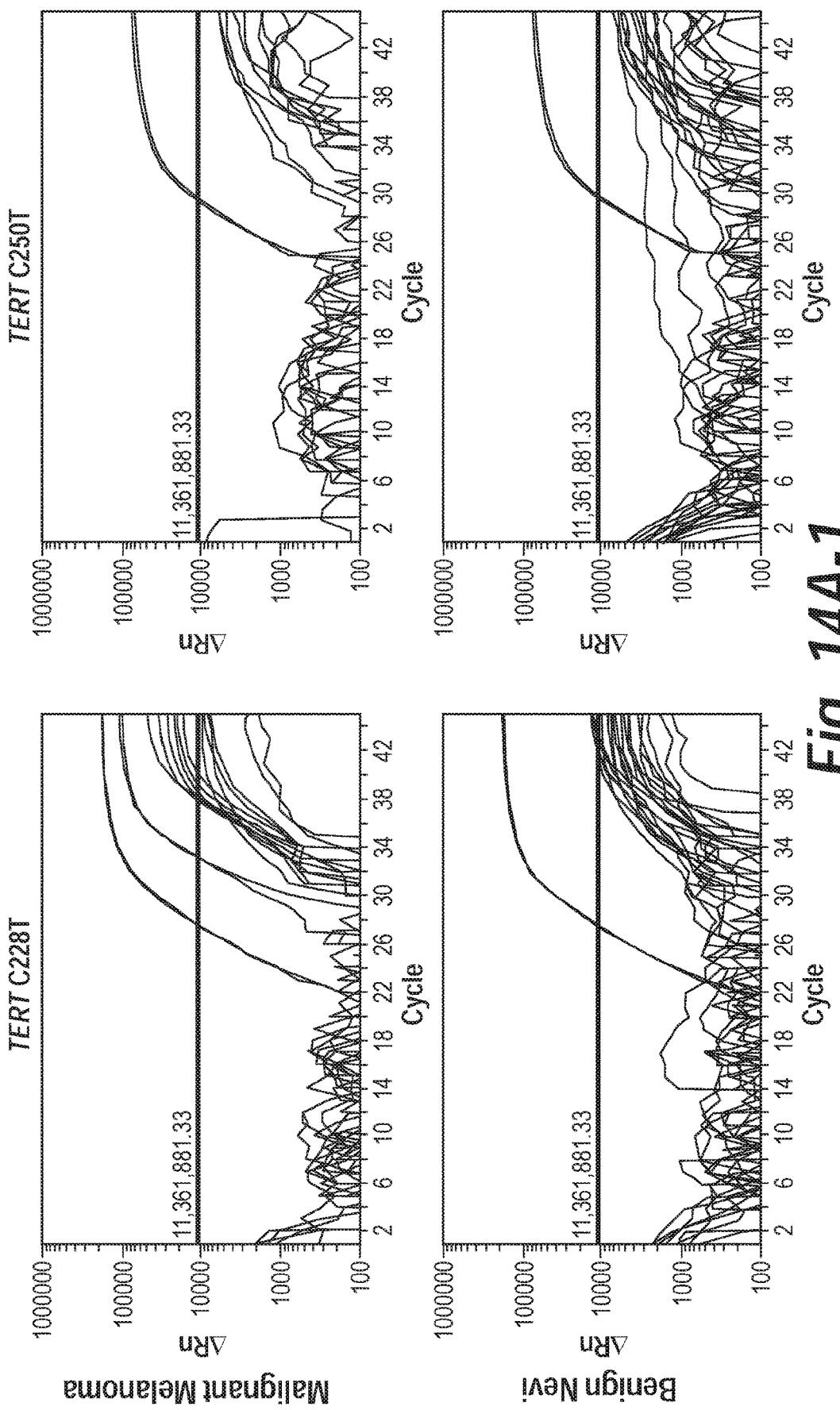
Figures 2, 14A:
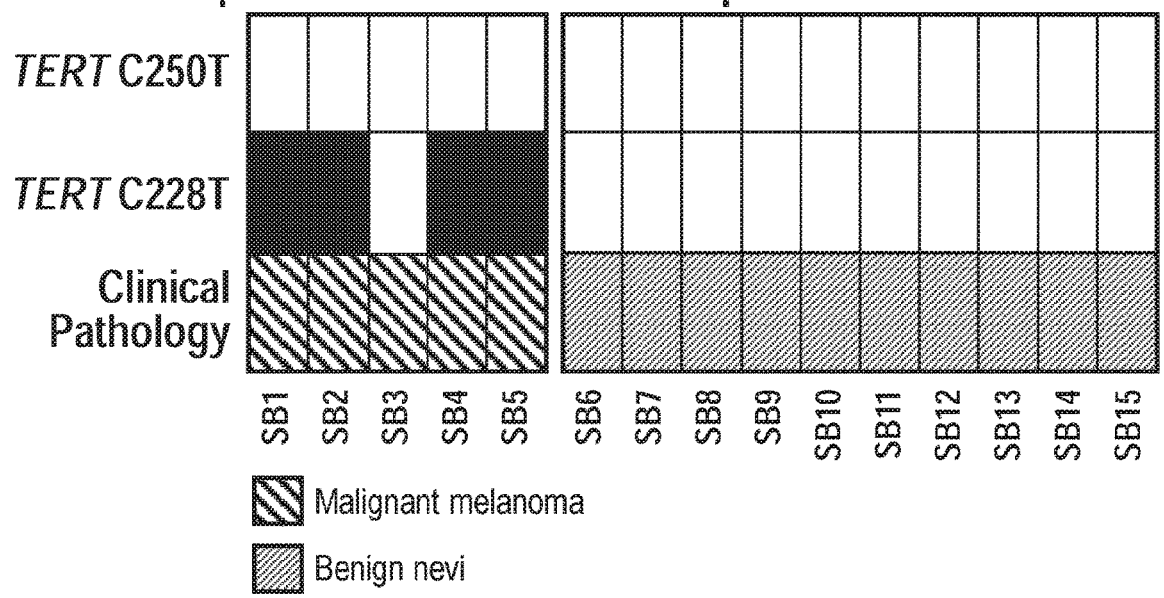
Figure 14B:
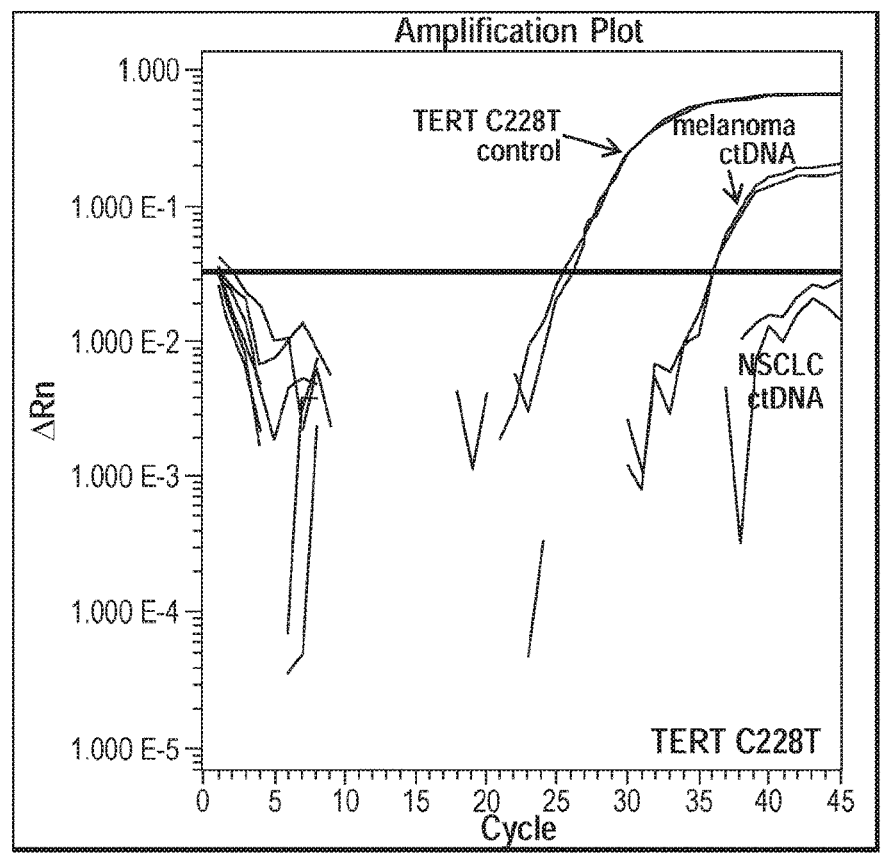
FIG. 14B graphically depicts the rapid detection of TERT promoter mutant alleles showing cell free DNA from serum of patient with newly diagnosed metastatic melanoma was positive for TERT C228T. Similarly purified cell free DNA from a patient with non-small cell lung cancer (NSCLC) was negative for TERT promoter allele mutants.
Figure 15:
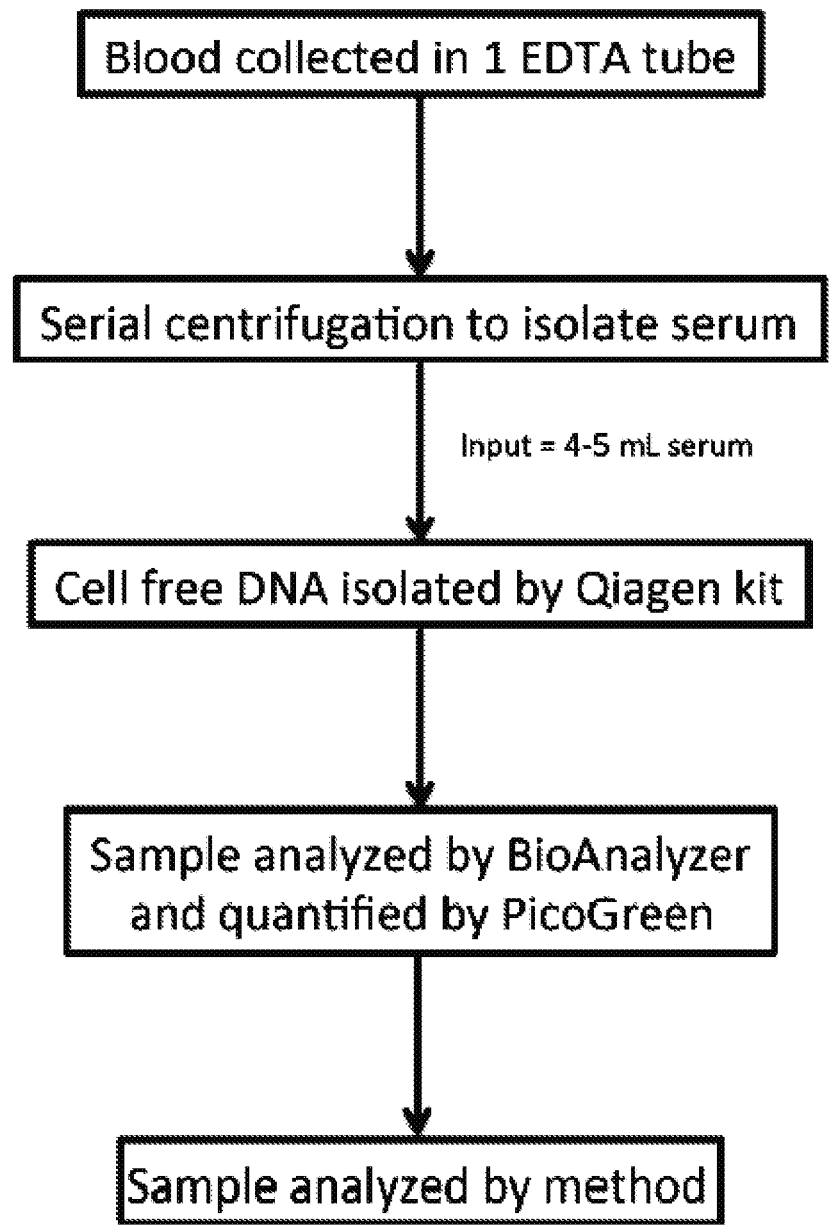
FIG. 15 graphically depicts a proposed workflow of the application of the method disclosed herein to detection of cell free mutant alleles in serum. Blood is collected in an EDTA-containing tube. Serum isolated by serial centrifugation. Cell free DNA extraction is completed by kit. This sample is analyzed and quantified. Normalized sample is applied to a plate already containing the optimized mastermix to detect IDH1 R132H, TERT C228T or TERT C250T with respective positive controls, and analyzed by the method disclosed herein.
Figure 18:
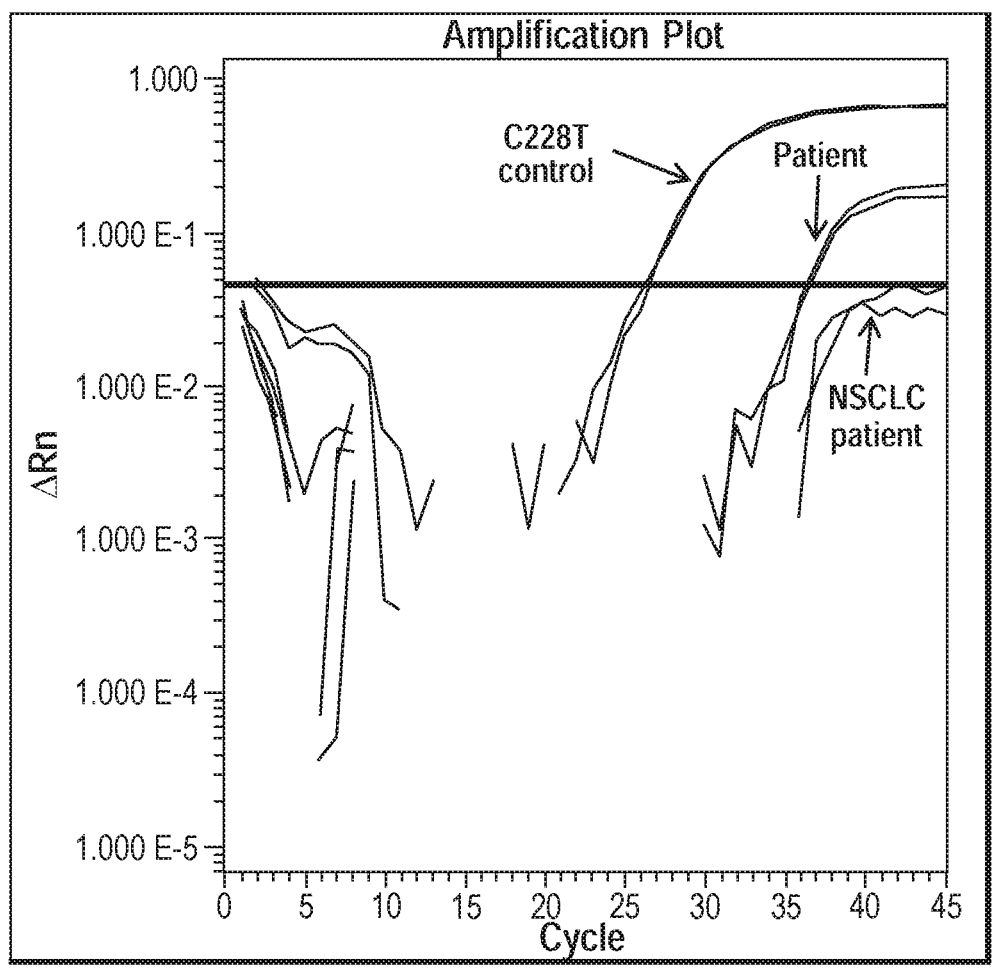
FIG. 18 graphically depicts the detection of cell free circulating TERT C228T in a patient with metastatic melanoma.
Figure 20:
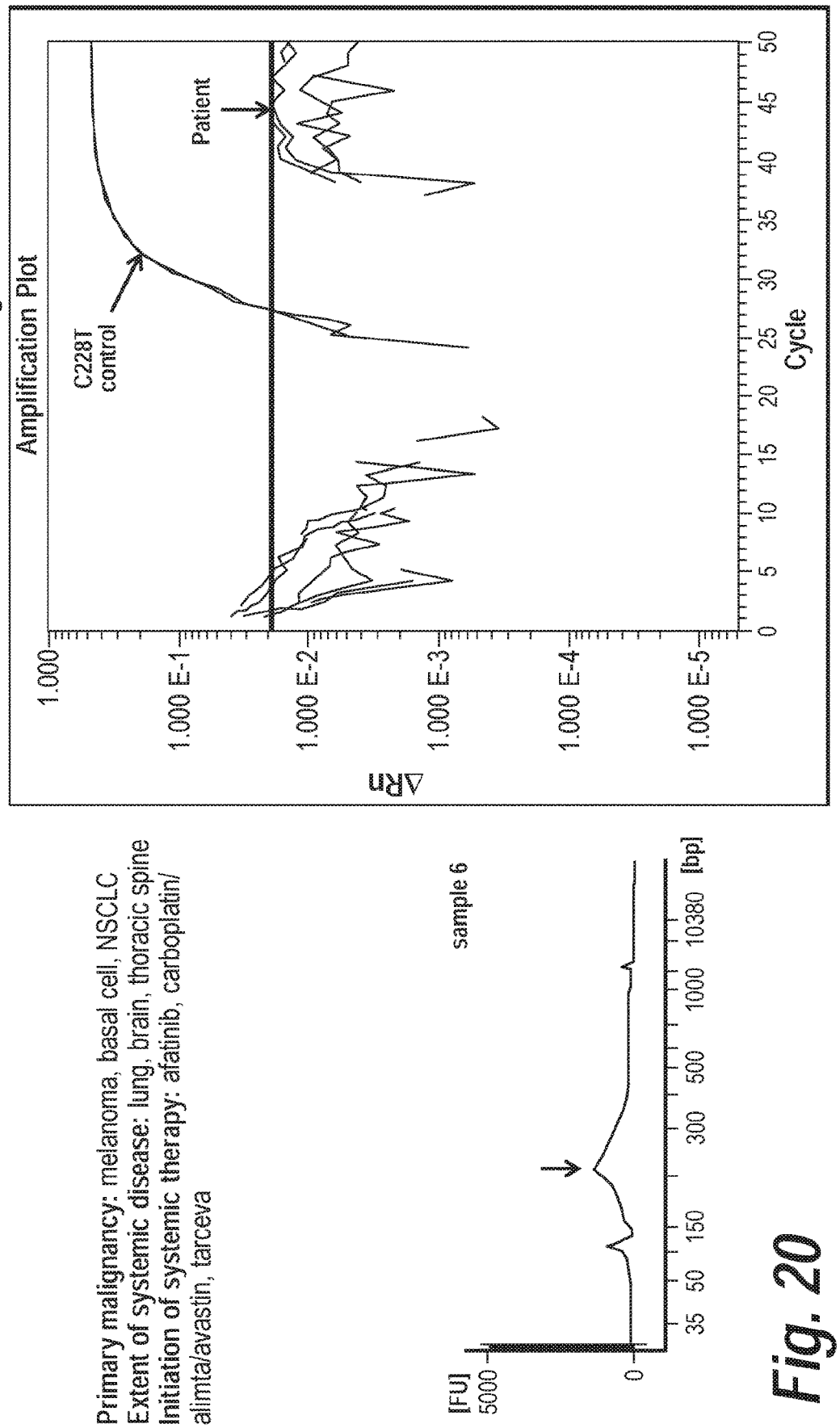
FIG. 20 graphically depicts the detection of cell free circulating TERT C228T to define the primary contribution to systemic disease.
Figure 21:
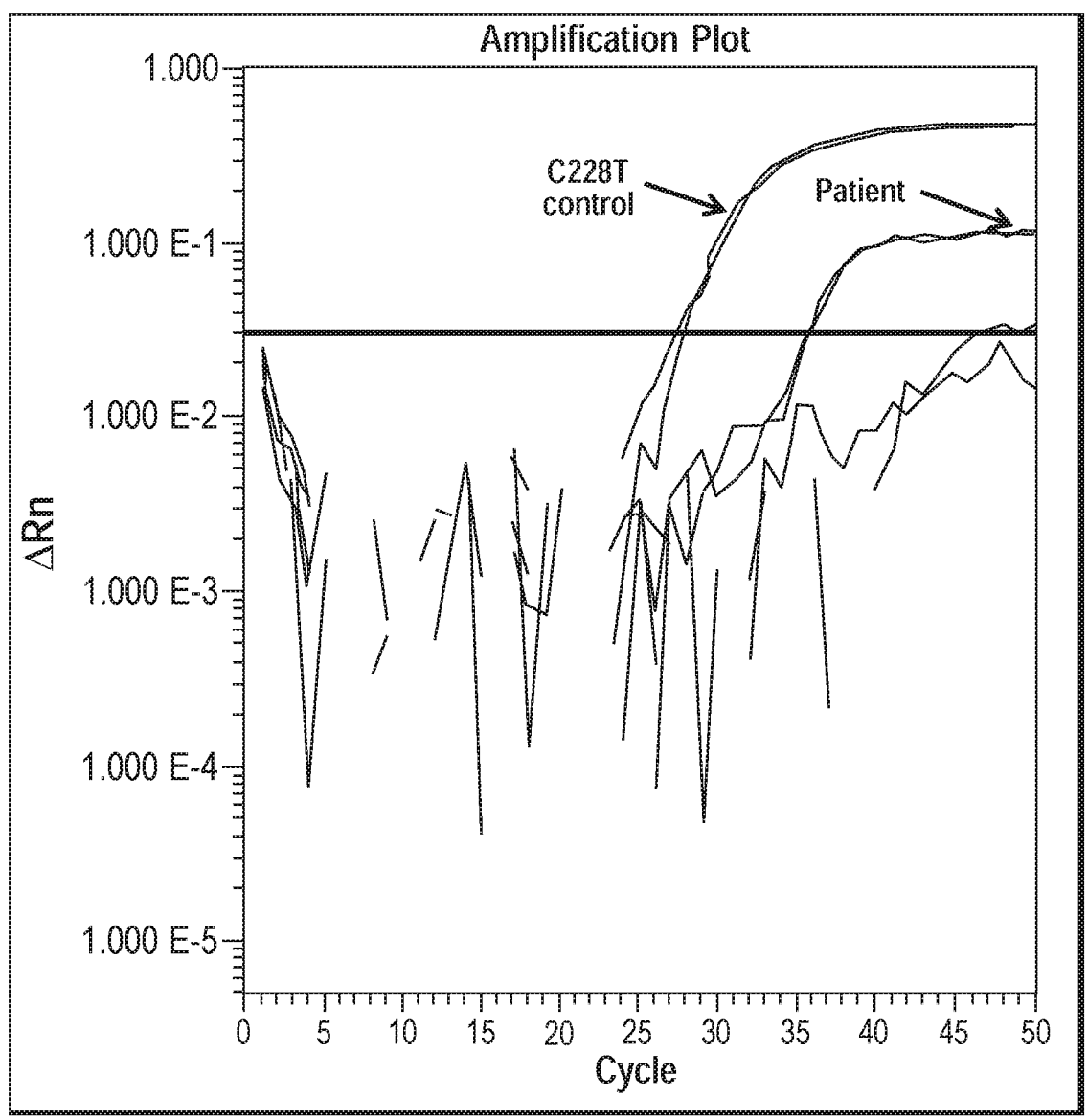
FIG. 21 graphically depicts the detection of cell free circulating TERT C228T in a patient with lung carcinoid.
Figure 22:
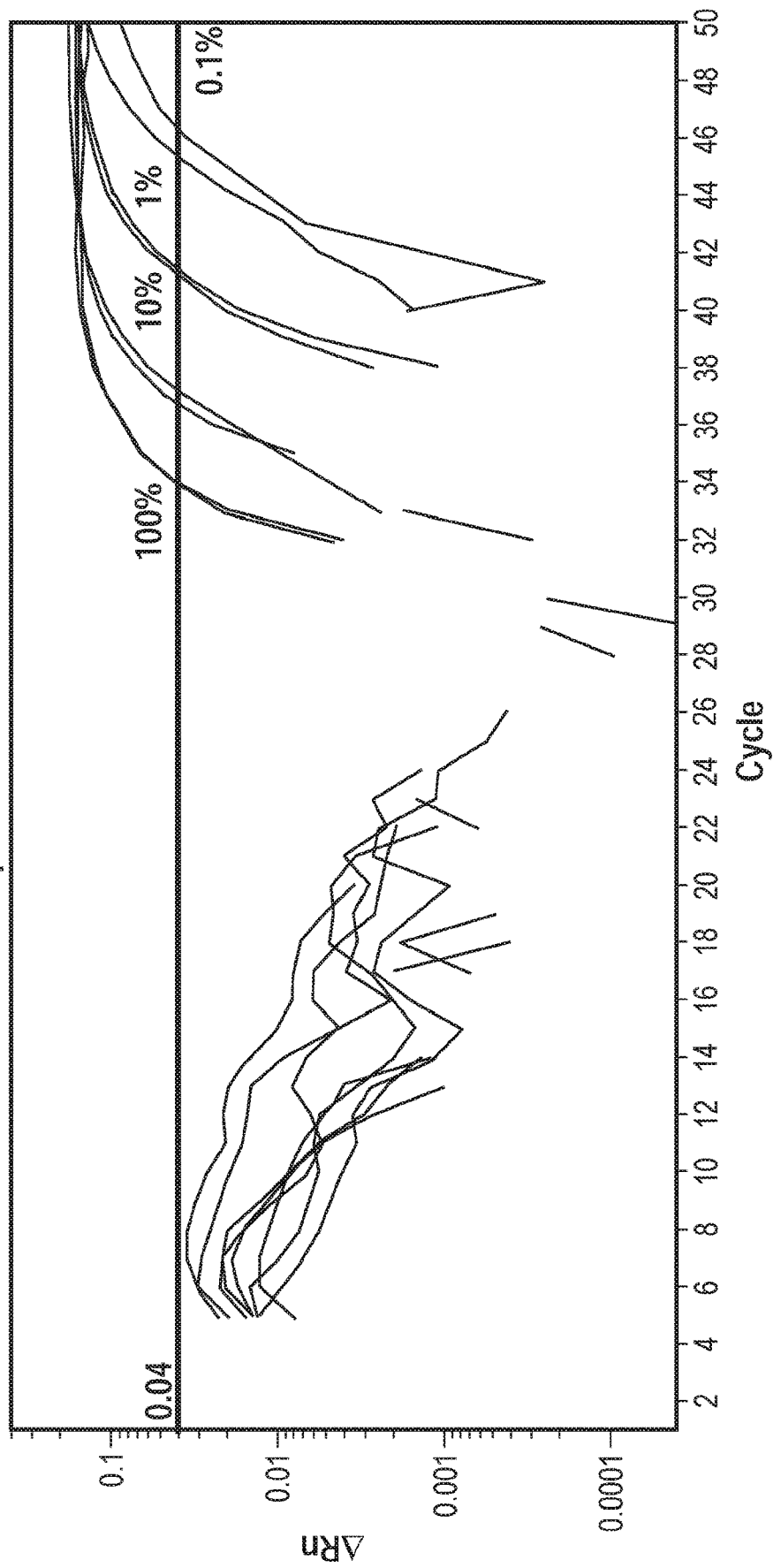
FIG. 22 graphically depicts the rapid and sensitive detection of BRAF promoter mutant alleles.

Example 2. Quantitation of Single Nucleotide Polymorphisms to Identify Melanoma: Application of the Method Disclosed Herein to Melanoma While malignant gliomas represent an ideal usage scenario, TERT promoter mutations are found in diverse cancer types, many of which are biopsied in the outpatient setting. Given that over 70% of melanoma harbor a mutation in the TERT promoter (F. W. Huang et al., Science. 339, 957-959 (2013), S. Horn et al., Science. 339, 959-961 (2013), J. Vinagre et al., Nat. Commun. 4, 2185 (2013)), we tested whether the method disclosed herein could be used for discriminating benign from malignant skin lesions. An analysis of 20 archived skin biopsies by the method disclosed herein revealed TERT C228T in zero and TERT C250T in 4/5 cases (FIG. FIGS. 14A-1 and 14A-2). Accordingly, identification of these two somatic SNPs by the method disclosed herein predicted malignant skin neoplasm in 4/5 cases, which captured 80% of malignant melanoma lesions in this cohort. Of note, the TERT promoter mutations were not identified in benign lesions. We also used the method disclosed herein to detect circulating cell free mutant TERT promoter alleles in a patient with metastatic melanoma. Serum from this patient was found to have circulating cell free TERT C228T and this diminished after initiation of ipilimumab (FIG. 14B).

Example 3. Sensitive Detection of TERT Alterations in Circulating Tumor DNA

Control Genomic Templates

The BT142 cell line (ATCC), which is hemizygous for the IDH1 R132H mutation (H. A. Luchman et al., Neuro-Oncol. 14, 184-191 (2012); H. A. Luchman, et al., Neuro-Oncol. 15, 979-980 (2013)) was grown under standard conditions. The TERT C228T and TERT C250T control templates were generated from primary glioma cell lines LN428 and LN443, respectively. Neurospheres were harvested and the cell pellet was extracted using the QiaAMP kit (Qiagen). DNA extracts were quantified by PicoGreen dye (Invitrogen) and normalized to 25 ng/µL in Tris-EDTA.

Quantitative PCR Primers and Conditions

The primers for TERT are 5'-CACGTGCGCAGCAG-GACGCAG-3' (SEQ ID NO: 9) and 5'-CTTCACCTTCCA- GCTCCGCCTC-3' (SEQ ID NO: 10) used at 500 nM. The TaqMan probe for detecting TERT C228T is 250 nM 5'-FAM-CCCAGCCCC+T+TCCGGGCCC-Dab-3' (SEQ ID NO: 15) and TERT C250T is 250 nM 5'-FAM-CCGAC-CCC+T+TCCGGGTCCC-Dab-3' (SEQ ID NO: 16). The PNA probes for blocking amplification of TERT C228 and TERT C250 are 150 nM 5'-CCCAGCCCCCTCCGGGCCC-3' (SEQ ID NO: 11) and 500 nM 5'-CCGACCCCTC-CCGGGTCCC-3' (SEQ ID NO: 12), respectively.

The TERT promoter mutations were detected using 5× buffer with enhancer and FAST 2G Taq polymerase (Kapa Biosystems).

The qPCR reaction were prepared in a final volume of 15 μL and run on an ABI 7900HT instrument (Applied Biosystems). PCR cycling times were 95° C. for 3:00 followed by 40-50 cycles at 95° for 10 seconds and 63.5° C. for 20 seconds.

Cell Free Tumor DNA Analysis from Blood

Patient blood samples were obtained under IRB approval from Massachusetts General Hospital and Dana Farber Cancer Institute. Samples were obtained in EDTA containing tubes and were centrifuged within 1 hour to separate plasma. Cell free DNA was purified from 3 mL plasma using the QiaAmp Circulating nucleic acid isolation kits following manufacturers protocol (Qiagen). Samples were eluted with 25 μL buffer AVE and 3 μL of this elute was used for each reaction for the method disclosed herein. Samples were also analyzed for overall DNA fragmentation state by Bioanalyzer (Agilent).

We next tested whether this approach for detecting these pathognomonic sSNVs could be applied as non-invasive biomarker detection methods for monitoring disease progression and treatment response. Identification of circulating cell free tumor DNA with digital PCR has been a widely applied to a variety of tumor subtypes (C. Bettegowda et al., Sci. Transl. Med. 6, 224ra24 (2014); S.-J. Dawson et al., N. Engl. J. Med. 368, 1199-1209 (2013)). One challenge of detecting cell free mutant alleles is the fragmented nature of circulating tumor DNA, necessitating short PCR amplicons to capture these fragments. A second challenge is the low abundance of tumor-specific alleles circulating as cell free DNA fragments, which was addressed by the ability to detect TERT C228T or TERT C250T with as little as 25 pg starting genomic material (FIG. 9). In this study we report that the method disclosed herein detected circulating cell free TERT C228T in a patient with clinically and radiographically progressive GBM while undergoing concurrent chemoradiation (FIG. 16). One year after transitioning the patient to bevacizumab, the disease is radiographically stable; however, this may be secondary to impaired uptake of contrast agent following VEGF inhibition leading to uncertainty regarding true disease progression. Analysis of the ctDNA by the method disclosed herein was unable to detect cell free TERT C228T at this later timepoint, supporting clinical treatment response.

Exemplary Embodiments

One aspect provides a system for detection or amplification of one or more single nucleotide polymorphisms or somatic variants in one or more target nucleic acids that may have high GC content and/or low sequence complexity in a sample, the system comprising:

(a) a forward primer that hybridizes to a first region on a sense strand of the target nucleic acid, (b) a reverse primer that hybridizes to a second region on an antisense strand of the target nucleic acid, (c) a locked nucleic acid (LNA) probe comprising an oligonucleotide with at least one LNA modification on at least one nucleotide, wherein the probe comprises a nucleic acid sequence that is complementary to a mutant allele sequence of the target nucleic acid and located within the region amplified by the forward primer and the reverse primer, (d) a peptide nucleic acid (PNA) blocker that hybridizes to a wild-type allele of the target nucleic acid, the blocker comprising peptide nucleic acid oligonucleotides that block amplification of the wild-type allele, and does not block amplification of the mutant allele, wherein the PNA blocker hybridizes to a region located within the region amplified by the forward and reverse primer, and (f) a reaction buffer, wherein the forward primer, the reverse primer, the LNA probe, and the PNA blocker are capable of recognizing their target sequences under same temperature conditions.

In an embodiment of the above-delineated system, the target nucleic acid has low sequence complexity.

In an embodiment of the above-delineated system, the target nucleic acid has high GC content.

In an embodiment of the foregoing, the target nucleic acid has a GC content of greater than 60%.

In an embodiment of the above-delineated system, the mutant allele comprises a single nucleotide polymorphism or somatic variant.

In an embodiment of the above-delineated system, wherein the sample is from a patient or human subject.

In an embodiment of the above-delineated system, the sample is from a tumor or metastatic lesion.

In an embodiment of the above-delineated system, the sample comprises a cancer cell.

In an embodiment of the above-delineated system, the sample comprises blood from a patient or human subject.

In an embodiment of the above-delineated system, the sample comprises tissue from a model organism, a cell from a tissue biopsy obtained from a subject, a cancer cell, nucleated cell obtained from blood obtained from a subject, or a circulating cancer cell.

In an embodiment of the above-delineated system, the target nucleic acid comprises a portion of the nucleic acid sequence of a telomerase reverse transcriptase (TERT) gene.

In an embodiment of the above-delineated system, the TERT gene comprises a portion of the nucleic acid sequence of the regulatory region of the TERT gene promoter.

In an embodiment of the above-delineated system, the mutant allele comprises variant C228T (hg19, chromosome 5:1,295,228) of the TERT gene promoter.

In an embodiment of the above-delineated system, the mutant allele comprises variant C250T (hg19, chromosome 5:1,295,250) of the TERT gene promoter.

In an embodiment of the above-delineated system, the system further comprises a control genomic DNA, comprising DNA which is homozygous, hemizygous or heterozygous for the mutant allele.

In an embodiment, the control genomic DNA is derived from glioma cell line LN428.

In another embodiment, the control genomic DNA is derived from glioma cell line LN443.

In an embodiment of the above-delineated system, the target nucleic acid comprises a portion of the nucleic acid sequence of an isocitrate dehydrogenase 1 (IDH1) gene.

In an embodiment of the above-delineated system, the mutant allele comprises a variant that encodes an IDH1 protein of variant R132H.

In an embodiment of the above-delineated system, the mutant allele comprises a variant that encodes an IDH1 protein of variant R132C.

In an embodiment of the above-delineated system, the mutant allele comprises a variant that encodes an IDH1 protein of variant R132G.

In an embodiment of the above-delineated system, the mutant allele comprises a variant that encodes an IDH1 protein of variant R132S.

In an embodiment of the above-delineated system, the mutant allele comprises a variant that encodes an IDH1 protein of variant R132L.

In an embodiment of the above-delineated system, the system further comprises a control genomic DNA, comprising DNA which is homozygous, hemizygous or heterozygous for the mutant allele.

In an embodiment of the foregoing, the control genomic DNA is derived from primary glioma cell line BT142.

In another embodiment of the above-delineated system, the target nucleic acid comprises a portion of the nucleic acid sequence of a proto-oncogene B-raf (BRAF) gene.

In an embodiment of the foregoing, the mutant allele comprises a variant that encodes a BRAF protein of variant V600E.

In another embodiment of the above-delineated system, the target nucleic acid comprises a portion of the nucleic acid sequence of a neuroblastomas RAS viral oncogene homolog (NRAS) gene.

In an embodiment of the above-delineated system, the mutant allele comprises a variant that encodes an NRAS protein of variant Q61R.

In an embodiment of the above-delineated system, the mutant allele comprises a variant that encodes an NRAS protein of variant Q61K.

In another embodiment of the above-delineated system, the target nucleic acid comprises a portion of the nucleic acid sequence of a guanine nucleotide-binding protein G(q) subunit α (GNAQ) gene.

In an embodiment of the above-delineated system, the mutant allele comprises a variant that encodes an GNAQ protein of variant R183Q.

In an embodiment of the above-delineated system, the mutant allele comprises a variant that encodes an GNAQ protein of variant Q209L.

In an embodiment of the above-delineated system, the mutant allele comprises a variant that encodes an GNAQ protein of variant Q209P.

In another embodiment of the above-delineated system, the target nucleic acid comprises a portion of the nucleic acid sequence of a guanine nucleotide-binding protein subunit α-11 (GNA11) gene.

In an embodiment of the above-delineated system, the mutant allele comprises a variant that encodes an GNA11 protein of variant Q209L.

In another embodiment of the above-delineated system, the target nucleic acid comprises a portion of the nucleic acid sequence of a H3 histone, family 3A (H3F3A) gene.

In an embodiment of the above-delineated system, the mutant allele comprises a variant that encodes an H3F3A protein of variant K27M.

In an embodiment of the above-delineated system, the mutant allele comprises a variant that encodes an H3F3A protein of variant G34R.

In another embodiment of the above-delineated system, the system further comprises a high-speed DNA polymerase.

In an embodiment of the foregoing, the high-speed DNA polymerase has an elongation rate of about 1 kb/second.

In an embodiment of the foregoing, the high-speed DNA polymerase is Kapa 2G FAST DNA Polymerase.

In another embodiment of the above-delineated system, the system further comprises one or more multi-well plates.

In another embodiment of the above-delineated system, the system further comprises DNA extraction reagents.

In an embodiment of the foregoing, the DNA extraction reagents are able to be used to extract DNA in 15 minutes or less.

In another embodiment of the above-delineated system, the system further comprises a cell lysis buffer.

In another embodiment of the above-delineated system, the system further comprises Proteinase K.

In another embodiment of the above-delineated system, the system further comprises deoxynucleotide triphosphates (dNTPs).

In another embodiment of the above-delineated system, the system further comprises MgCl2.

In an embodiment of the above-delineated system wherein the target nucleic acid comprises a portion of the nucleic acid sequence of a telomerase reverse transcriptase (TERT) gene, the forward primer comprises the nucleic acid sequence of 5'-CACGTGCGCAGCAGGACGCAG-3'.

In an embodiment of the above-delineated system wherein the target nucleic acid comprises a portion of the nucleic acid sequence of a telomerase reverse transcriptase (TERT) gene, the reverse primer comprises the nucleic acid sequence of 5'-CTTCACCTTCCAGCTCCGCCTC-3'.

In an embodiment of the above-delineated system wherein the target nucleic acid comprises a portion of the nucleic acid sequence of a telomerase reverse transcriptase (TERT) gene, the PNA blocker comprises the nucleic acid sequence of 5'-CCCAGCCCCCTCCGGGCCC-3'.

In an embodiment of the above-delineated system, the LNA probe comprises a first end and a second end, wherein the first end comprises a label and wherein the second end comprises a quencher.

In an embodiment of the above-delineated system wherein the target nucleic acid comprises a portion of the nucleic acid sequence of a telomerase reverse transcriptase (TERT) gene, the LNA probe comprises the nucleic acid sequence of 5'-FAM-CCCAGCCCC+T+TCCGGGCCC-Dab-3', wherein nucleotides preceded by a "+" are LNA modified nucleotides, FAM is fluorescein moiety, and Dab is diaminobenzidine.

In an embodiment of the above-delineated system wherein the target nucleic acid comprises a portion of the nucleic acid sequence of a telomerase reverse transcriptase (TERT) gene, the LNA probe comprises the nucleic acid sequence of 5'-FAM-CCGACCCC+T+TCCGGGTCCC-Dab-3', wherein nucleotides preceded by a "+" are LNA modified nucleotides, FAM is fluorescein moiety, and Dab is diaminobenzidine.

In an embodiment of the above-delineated system wherein the target nucleic acid comprises a portion of the nucleic acid sequence of an isocitrate dehydrogenase 1 (IDH1) gene, the forward primer comprises the nucleic acid sequence of 5'-CCGGCTTGTGAGTGGATGGG-TAAAACCT-3'.

In an embodiment of the above-delineated system wherein the target nucleic acid comprises a portion of the nucleic acid sequence of an isocitrate dehydrogenase 1 (IDH1) gene, the reverse primer comprises the nucleic acid sequence of 5'-CATTATTGCCAACATGACTTACTT-GATCCCC-3'.

In an embodiment of the above-delineated system wherein the target nucleic acid comprises a portion of the nucleic acid sequence of an isocitrate dehydrogenase 1 (IDH1) gene, the PNA blocker comprises the nucleic acid sequence of 5'-AGGTCGTCATGC-3'.

In an embodiment of the above-delineated system wherein the target nucleic acid comprises a portion of the nucleic acid sequence of an isocitrate dehydrogenase 1 (IDH1) gene, the LNA probe comprises the nucleic acid sequence of 5'-AGG+T+C+A+T+CAT+GC-3', wherein nucleotides preceded by a "+" are LNA modified nucleotides.

In an embodiment of the above-delineated system wherein the target nucleic acid comprises a portion of the nucleic acid sequence of an isocitrate dehydrogenase 1 (IDH1) gene, the LNA probe comprises the nucleic acid sequence of 5'-AGG+T+T+G+T+C+ATGC-3', wherein nucleotides preceded by a "+" are LNA modified nucleotides.

In an embodiment of the above-delineated system wherein the target nucleic acid comprises a portion of the nucleic acid sequence of an isocitrate dehydrogenase 1 (IDH1) gene, the LNA probe comprises the nucleic acid sequence of 5'-AGGT+G+G+T+CAT+GC-3', wherein nucleotides preceded by a "+" are LNA modified nucleotides.

In an embodiment of the above-delineated system wherein the target nucleic acid comprises a portion of the nucleic acid sequence of an isocitrate dehydrogenase 1 (IDH1) gene, the LNA probe comprises the nucleic acid sequence of 5'-AGGT+A+G+T+CA+T+GC-3' wherein nucleotides preceded by a "+" are LNA modified nucleotides.

In an embodiment of the above-delineated system wherein the target nucleic acid comprises a portion of the nucleic acid sequence of an isocitrate dehydrogenase 1 (IDH1) gene, the LNA probe comprises the nucleic acid sequence of 5'-AGG+T+C+T+T+CAT+GC-3' wherein nucleotides preceded by a "+" are LNA modified nucleotides.

In an embodiment of the above-delineated system wherein the target nucleic acid comprises a portion of the nucleic acid sequence of an isocitrate dehydrogenase 1 (IDH1) gene, the LNA probe comprises the nucleic acid sequence of 5'-FAM-AGG+T+C+A+T+CAT+GC-Dab-3', wherein nucleotides preceded by a "+" are LNA modified nucleotides, FAM is fluorescein moiety, and Dab is diaminobenzidine.

In an embodiment of the above-delineated system wherein the target nucleic acid comprises a portion of the nucleic acid sequence of an isocitrate dehydrogenase 1 (IDH1) gene, the LNA probe comprises the nucleic acid sequence of 5'-MAXN-AGG+T+T+G+T+C+ATGC-Dab-3', wherein nucleotides preceded by a "+" are LNA modified nucleotides, MAXN is fluorescent moiety, and Dab is diaminobenzidine.

In an embodiment of the above-delineated system wherein the target nucleic acid comprises a portion of the nucleic acid sequence of an isocitrate dehydrogenase 1 (IDH1) gene, the LNA probe comprises the nucleic acid sequence of 5'-MAXN-AGGT+G+G+T+CAT+GC-Dab-3', wherein nucleotides preceded by a "+" are LNA modified nucleotides, MAXN is fluorescent moiety, and Dab is diaminobenzidine.

In an embodiment of the above-delineated system wherein the target nucleic acid comprises a portion of the nucleic acid sequence of an isocitrate dehydrogenase 1 (IDH1) gene, the LNA probe comprises the nucleic acid sequence of 5'-MAXN-AGGT+A+G+T+CA+T+GC-Dab-3' wherein nucleotides preceded by a "+" are LNA modified nucleotides, MAXN is fluorescent moiety, and Dab is diaminobenzidine.

In an embodiment of the above-delineated system wherein the target nucleic acid comprises a portion of the nucleic acid sequence of an isocitrate dehydrogenase 1 (IDH1) gene, the LNA probe comprises the nucleic acid sequence of 5'-MAXN-AGG+T+C+T+T+CAT+GC-Dab-3' wherein nucleotides preceded by a "+" are LNA modified nucleotides, MAXN is fluorescent moiety, and Dab is diaminobenzidine.

In an embodiment of the above-delineated system wherein the target nucleic acid comprises a portion of the nucleic acid sequence of a proto-oncogene B-raf (BRAF) gene, the forward primer comprises the nucleic acid sequence of 5'-ACAGGGCATGGAGAGTGGGTC-3'.

In an embodiment of the above-delineated system wherein the target nucleic acid comprises a portion of the nucleic acid sequence of a proto-oncogene B-raf (BRAF) gene, the reverse primer comprises the nucleic acid sequence of 5'-CAAACTGATGGGACCCACTCCAT-3'.

In an embodiment of the above-delineated system wherein the target nucleic acid comprises a portion of the nucleic acid sequence of a proto-oncogene B-raf (BRAF) gene, the PNA blocker comprises the nucleic acid sequence of 5'-CATCGAGATTTCACTGTAGCTAGA-3'.

In an embodiment of the above-delineated system wherein the target nucleic acid comprises a portion of the nucleic acid sequence of a proto-oncogene B-raf (BRAF) gene, the LNA probe comprises the nucleic acid sequence of 5'-AGA+TT+T+C+T+CT+GT+AG+C-3', wherein nucleotides preceded by a "+" are LNA modified nucleotides.

In an embodiment of the above-delineated system wherein the target nucleic acid comprises a portion of the nucleic acid sequence of a proto-oncogene B-raf (BRAF) gene, the LNA probe comprises the nucleic acid sequence of 5'-FAM-AGA+TT+T+C+T+CT+GT+AG+C-Dab-3', wherein nucleotides preceded by a "+" are LNA modified nucleotides, FAM is fluorescein moiety, and Dab is diaminobenzidine.

In an embodiment of the above-delineated system wherein the target nucleic acid comprises a portion of the nucleic acid sequence of a proto-oncogene B-raf (BRAF) gene, the LNA probe comprises the nucleic acid sequence of 5'-MAXN-AGA+TT+T+C+T+CT+GT+AG+C-Dab-3', wherein nucleotides preceded by a "+" are LNA modified nucleotides, MAXN is fluorescent moiety, and Dab is diaminobenzidine.

In an embodiment of the above-delineated system wherein the target nucleic acid comprises a portion of the nucleic acid sequence of a neuroblastomas RAS viral oncogene homolog (NRAS) gene, the forward primer comprises the nucleic acid sequence of 5'-AGTGGTTATAGATGGT-GAAACCTG-3'.

In an embodiment of the above-delineated system wherein the target nucleic acid comprises a portion of the nucleic acid sequence of a neuroblastomas RAS viral oncogene homolog (NRAS) gene, the reverse primer comprises the nucleic acid sequence of 5'-ACAGAGGAAGCCT-TCGCCTG-3'.

In an embodiment of the above-delineated system wherein the target nucleic acid comprises a portion of the nucleic acid sequence of a neuroblastomas RAS viral oncogene homolog (NRAS) gene, the PNA blocker comprises the nucleic acid sequence of 5'-CAGCTGGACAAGAAGAG-TAC-KK-3'.

In an embodiment of the above-delineated system wherein the target nucleic acid comprises a portion of the nucleic acid sequence of a neuroblastomas RAS viral oncogene homolog (NRAS) gene, the LNA probe comprises the nucleic acid sequence of 5'-CTGG+AC+G+AG+AA+GAGTA-3', wherein nucleotides preceded by a "+" are LNA modified nucleotides.

In an embodiment of the above-delineated system wherein the target nucleic acid comprises a portion of the nucleic acid sequence of a neuroblastomas RAS viral oncogene homolog (NRAS) gene, the LNA probe comprises the nucleic acid sequence of 5'-CAG+CTGGA+A+A+AGAA+GA+GTA-3', wherein nucleotides preceded by a "+" are LNA modified nucleotides.

In an embodiment of the above-delineated system wherein the target nucleic acid comprises a portion of the nucleic acid sequence of a neuroblastomas RAS viral oncogene homolog (NRAS) gene, the LNA probe comprises the nucleic acid sequence of 5'-FAM-CTGG+AC+G+AG+AA+GAGTA-Dab-3', wherein nucleotides preceded by a "+" are LNA modified nucleotides, FAM is fluorescein moiety, and Dab is diaminobenzidine.

In an embodiment of the above-delineated system wherein the target nucleic acid comprises a portion of the nucleic acid sequence of a neuroblastomas RAS viral oncogene homolog (NRAS) gene, the LNA probe comprises the nucleic acid sequence of 5'-FAM-CAG+CTGGA+A+A+AGAA+GA+GTA-Dab-3', wherein nucleotides preceded by a "+" are LNA modified nucleotides, FAM is fluorescein moiety, and Dab is diaminobenzidine.

In an embodiment of the above-delineated system wherein the target nucleic acid comprises a portion of the nucleic acid sequence of a neuroblastomas RAS viral oncogene homolog (NRAS) gene, the LNA probe comprises the nucleic acid sequence of 5'-MAXN-CTGG+AC+G+AG+AA+GAGTA-Dab-3', wherein nucleotides preceded by a "+" are LNA modified nucleotides, MAXN is fluorescent moiety, and Dab is diaminobenzidine.

In an embodiment of the above-delineated system wherein the target nucleic acid comprises a portion of the nucleic acid sequence of a neuroblastomas RAS viral oncogene homolog (NRAS) gene, the LNA probe comprises the nucleic acid sequence of 5'-MAXN-CAG+CTGGA+A+A+AGAA+GA+GTA-Dab-3', wherein nucleotides preceded by a "+" are LNA modified nucleotides, MAXN is fluorescent moiety, and Dab is diaminobenzidine.

In an embodiment of the above-delineated system wherein the target nucleic acid comprises a portion of the nucleic acid sequence of a guanine nucleotide-binding protein G(q) subunit α (GNAQ) gene, the forward primer comprises the nucleic acid sequence of 5'-TTGGACCGCGTAGCTGACCCT-3'.

In an embodiment of the above-delineated system wherein the target nucleic acid comprises a portion of the nucleic acid sequence of a guanine nucleotide-binding protein G(q) subunit α (GNAQ) gene, the reverse primer comprises the nucleic acid sequence of 5'-GCTGGGAAATAGGTTTCATGGAC-3'.

In an embodiment of the above-delineated system wherein the target nucleic acid comprises a portion of the nucleic acid sequence of a guanine nucleotide-binding protein G(q) subunit α (GNAQ) gene, the PNA blocker comprises the nucleic acid sequence of 5'-TTAGAGTTC-GAGTCCCCA-3'.

In an embodiment of the above-delineated system wherein the target nucleic acid comprises a portion of the nucleic acid sequence of a guanine nucleotide-binding protein G(q) subunit α (GNAQ) gene, the LNA probe comprises the nucleic acid sequence of 5'-AGAGT+TC+A+AGT+CCCCAC-3', wherein nucleotides preceded by a "+" are LNA modified nucleotides.

In an embodiment of the above-delineated system wherein the target nucleic acid comprises a portion of the nucleic acid sequence of a guanine nucleotide-binding protein G(q) subunit α (GNAQ) gene, the LNA probe comprises the nucleic acid sequence of 5'-FAM-AGAGT+TC+A+AGT+CCCCAC-Dab-3', wherein nucleotides preceded by a "+" are LNA modified nucleotides, FAM is fluorescein moiety, and Dab is diaminobenzidine.

In an embodiment of the above-delineated system wherein the target nucleic acid comprises a portion of the nucleic acid sequence of a guanine nucleotide-binding protein G(q) subunit α (GNAQ) gene, the LNA probe comprises the nucleic acid sequence of 5'-MAXN-AGAGT+TC+A+AGT+CCCCAC-Dab-3', wherein nucleotides preceded by a "+" are LNA modified nucleotides, MAXN is fluorescent moiety, and Dab is diaminobenzidine.

In an embodiment of the above-delineated system wherein the target nucleic acid comprises a portion of the nucleic acid sequence of a guanine nucleotide-binding protein G(q) subunit α (GNAQ) gene, the forward primer comprises the nucleic acid sequence of 5'-CCCTAAGTTT-GTAAGTAGTGCTATA-3'.

In an embodiment of the above-delineated system wherein the target nucleic acid comprises a portion of the nucleic acid sequence of a guanine nucleotide-binding protein G(q) subunit α (GNAQ) gene, the reverse primer comprises the nucleic acid sequence of 5'-TCACTAAGCGCTACTAGAAACATG-3'.

In an embodiment of the above-delineated system wherein the target nucleic acid comprises a portion of the nucleic acid sequence of a guanine nucleotide-binding protein G(q) subunit α (GNAQ) gene, the PNA blocker comprises the nucleic acid sequence of 5'-GGGGC-CAAAGGTCAGAGA-3'.

In an embodiment of the above-delineated system wherein the target nucleic acid comprises a portion of the nucleic acid sequence of a guanine nucleotide-binding protein G(q) subunit α (GNAQ) gene, the LNA probe comprises the nucleic acid sequence of 5'-AGGGGCC+T+AAGGTCAGAG-3', wherein nucleotides preceded by a "+" are LNA modified nucleotides.

In an embodiment of the above-delineated system wherein the target nucleic acid comprises a portion of the nucleic acid sequence of a guanine nucleotide-binding protein G(q) subunit α (GNAQ) gene, the LNA probe comprises the nucleic acid sequence of 5'-GGGCC+C+AAGGTCA-GAGA-3', wherein nucleotides preceded by a "+" are LNA modified nucleotides.

In an embodiment of the above-delineated system wherein the target nucleic acid comprises a portion of the nucleic acid sequence of a guanine nucleotide-binding protein G(q) subunit α (GNAQ) gene, the LNA probe comprises the nucleic acid sequence of 5'-FAM-AGGGGCC+T+AAGGTCAGAG-Dab-3', wherein nucleotides preceded by a "+" are LNA modified nucleotides, FAM is fluorescein moiety, and Dab is diaminobenzidine.

In an embodiment of the above-delineated system wherein the target nucleic acid comprises a portion of the nucleic acid sequence of a guanine nucleotide-binding protein G(q) subunit α (GNAQ) gene, the LNA probe comprises the nucleic acid sequence of 5'-FAM-GGGCC+C+AAGGTCAGAGA-Dab-3', wherein nucleotides preceded by a "+" are LNA modified nucleotides, FAM is fluorescein moiety, and Dab is diaminobenzidine.

In an embodiment of the above-delineated system wherein the target nucleic acid comprises a portion of the nucleic acid sequence of a guanine nucleotide-binding protein G(q) subunit α (GNAQ) gene, the LNA probe comprises the nucleic acid sequence of 5'-MAXN-AGGGGCC+T+AAGGTCAGAG-Dab-3', wherein nucleotides preceded by a "+" are LNA modified nucleotides, MAXN is fluorescent moiety, and Dab is diaminobenzidine.

In an embodiment of the above-delineated system wherein the target nucleic acid comprises a portion of the nucleic acid sequence of a guanine nucleotide-binding protein G(q) subunit α (GNAQ) gene, the LNA probe comprises the nucleic acid sequence of 5'-MAXN-GGGCC+C+AAGGTCAGAGA-Dab-3', wherein nucleotides preceded by a "+" are LNA modified nucleotides, MAXN is fluorescent moiety, and Dab is diaminobenzidine.

In an embodiment of the above-delineated system wherein the target nucleic acid comprises a portion of the nucleic acid sequence of a guanine nucleotide-binding protein subunit α-11 (GNA11) gene, the forward primer comprises the nucleic acid sequence of 5'-GCAGATTGGGC-CTTGGGGCG-3'.

In an embodiment of the above-delineated system wherein the target nucleic acid comprises a portion of the nucleic acid sequence of a guanine nucleotide-binding protein subunit α-11 (GNA11) gene, the reverse primer comprises the nucleic acid sequence of 5'-TCGCTGAGGGC-GACGAGAAAC-3'.

In an embodiment of the above-delineated system wherein the target nucleic acid comprises a portion of the nucleic acid sequence of a guanine nucleotide-binding protein subunit α-11 (GNA11) gene, the PNA blocker comprises the nucleic acid sequence of 5'-GGGCCAGCG-GTCGGAGC-3'.

In an embodiment of the above-delineated system wherein the target nucleic acid comprises a portion of the nucleic acid sequence of a guanine nucleotide-binding protein subunit α-11 (GNA11) gene, the LNA probe comprises the nucleic acid sequence of 5'-GGG+CC+T+GCGGTCGG-3', wherein nucleotides preceded by a "+" are LNA modified nucleotides.

In an embodiment of the above-delineated system wherein the target nucleic acid comprises a portion of the nucleic acid sequence of a guanine nucleotide-binding protein subunit α-11 (GNA11) gene, the LNA probe comprises the nucleic acid sequence of 5'-FAM-GGG+CC+T+GCG-GTCGG-Dab-3', wherein nucleotides preceded by a "+" are LNA modified nucleotides, FAM is fluorescein moiety, and Dab is diaminobenzidine.

In an embodiment of the above-delineated system wherein the target nucleic acid comprises a portion of the nucleic acid sequence of a guanine nucleotide-binding protein subunit α-11 (GNA11) gene, the LNA probe comprises the nucleic acid sequence of 5'-MAXN-GGG+CC+T+GCG-GTCGG-Dab-3', wherein nucleotides preceded by a "+" are LNA modified nucleotides, MAXN is fluorescent moiety, and Dab is diaminobenzidine.

In an embodiment of the above-delineated system wherein the target nucleic acid comprises a portion of the nucleic acid sequence of a H3 histone, family 3A (H3F3A) gene, the forward primer comprises the nucleic acid sequence of 5'-CTGCCCGCAAATCGACCGGT-3'.

In an embodiment of the above-delineated system wherein the target nucleic acid comprises a portion of the nucleic acid sequence of a H3 histone, family 3A (H3F3A) gene, the reverse primer comprises the nucleic acid sequence of 5'-GGATACATACAAGAGAGACTTTGTC-3'.

In an embodiment of the above-delineated system wherein the target nucleic acid comprises a portion of the nucleic acid sequence of a H3 histone, family 3A (H3F3A) gene, the PNA blocker comprises the nucleic acid sequence of 5'-GCCGCTCGCAAGAGTGCGCC-3'.

In an embodiment of the above-delineated system wherein the target nucleic acid comprises a portion of the nucleic acid sequence of a H3 histone, family 3A (H3F3A) gene, the PNA blocker comprises the nucleic acid sequence of 5'-TTCTTCACCCCTCCAGTAG-3'.

In an embodiment of the above-delineated system wherein the target nucleic acid comprises a portion of the nucleic acid sequence of a H3 histone, family 3A (H3F3A) gene, the LNA probe comprises the nucleic acid sequence of 5'-CGCTCGC+A+T+GAGTG-3', wherein nucleotides preceded by a "+" are LNA modified nucleotides.

In an embodiment of the above-delineated system wherein the target nucleic acid comprises a portion of the nucleic acid sequence of a H3 histone, family 3A (H3F3A) gene, the LNA probe comprises the nucleic acid sequence of 5'-FAM-CGCTCGC+A+T+GAGTG-Dab-3', wherein nucleotides preceded by a "+" are LNA modified nucleotides, FAM is fluorescein moiety, and Dab is diaminobenzidine.

In an embodiment of the above-delineated system wherein the target nucleic acid comprises a portion of the nucleic acid sequence of a H3 histone, family 3A (H3F3A) gene, the LNA probe comprises the nucleic acid sequence of 5'-MAXN-CGCTCGC+A+T+GAGTG-Dab-3', wherein nucleotides preceded by a "+" are LNA modified nucleotides, MAXN is fluorescent moiety, and Dab is diaminobenzidine.

In an embodiment of the above-delineated system wherein the target nucleic acid comprises a portion of the nucleic acid sequence of a H3 histone, family 3A (H3F3A) gene, the LNA probe comprises the nucleic acid sequence of 5'-TACT+GGA+A+GG+GTGAAGA-3', wherein nucleotides preceded by a "+" are LNA modified nucleotides.

In an embodiment of the above-delineated system wherein the target nucleic acid comprises a portion of the nucleic acid sequence of a H3 histone, family 3A (H3F3A) gene, the LNA probe comprises the nucleic acid sequence of 5'-FAM-TACT+GGA+A+GG+GTGAAGA-Dab-3', wherein nucleotides preceded by a "+" are LNA modified nucleotides, FAM is fluorescein moiety, and Dab is diaminobenzidine.

In an embodiment of the above-delineated system wherein the target nucleic acid comprises a portion of the nucleic acid sequence of a H3 histone, family 3A (H3F3A) gene, the LNA probe comprises the nucleic acid sequence of 5'-MAXN-TACT+GGA+A+GG+GTGAAGA-Dab-3', wherein nucleotides preceded by a "+" are LNA modified nucleotides, MAXN is fluorescent moiety, and Dab is diaminobenzidine.

One aspect provides a kit comprising the system of any one or more of the above-delineated aspects and embodiments.

One aspect provides a method of using the system of any one or more of the above-delineated aspects and embodiments to detect or amplify one or more single nucleotide polymorphisms or somatic variants in a target nucleic acid with low sequence complexity and/or high GC content, in a sample from a subject comprising:
(a) isolating DNA from the sample;
(b) denaturing the isolated DNA;

(c) annealing the forward primer, the reverse primer, the LNA probe, and the PNA blocker to the DNA at the same temperature conditions; and (d) amplifying and detecting a DNA amplicon comprising the one or more single nucleotide polymorphisms, thereby detecting or amplifying one or more single nucleotide polymorphisms.

One aspect provides a method for establishing a molecular diagnosis in at least one cancer in a subject, the method comprising:

(a) isolating DNA from a sample from the subject;

(b) denaturing the DNA isolated from the sample and a control DNA template;

(c) annealing a forward primer that hybridizes to a first region on a sense strand of a first target nucleic acid, a reverse primer that hybridizes to a second region on an antisense strand of the first target nucleic acid, a locked nucleic acid (LNA) probe comprising an oligonucleotide with at least one LNA modification on at least one nucleotide, wherein the probe comprises a nucleic acid sequence that is complementary to a mutant allele of the first target nucleic acid, and a peptide nucleic acid (PNA) blocker that hybridizes to a wild-type allele of the first target nucleic acid;

(d) amplifying a DNA amplicon comprising the mutant allele in the first target nucleic acid;

(e) detecting the mutant allele in the first target nucleic acid in the sample; and (f) quantifying the amount of the mutant allele in the first target nucleic acid in the sample relative to the amount in a control, wherein a higher prevalence of the amount of mutant allele in the sample relative to the control indicates presence and/or stage of the cancer in the subject.

In an embodiment of the above-delineated method for establishing a molecular diagnosis, the sample comprises a tissue biopsy, blood, plasma, serum or cerebrospinal fluid from the subject.

In an embodiment of the foregoing method, the blood, plasma, serum or cerebrospinal fluid from the subject comprises one or more circulating cancer cells.

In an embodiment of the above-delineated method for establishing a molecular diagnosis, the sample comprises tissue from the subject.

In an embodiment of the foregoing method, the tissue from the subject comprises one or more cancer cells.

In an embodiment of the above-delineated method for establishing a molecular diagnosis, the amplifying is performed in the presence of a DNA polymerase.

In an embodiment of the foregoing, the DNA polymerase is a high-speed DNA polymerase.

In an embodiment, the high-speed DNA polymerase has an elongation rate of about 1 kb/second.

In another embodiment, the high-speed DNA polymerase is Kapa 2G FAST DNA Polymerase.

In an embodiment of the above-delineated method for establishing a molecular diagnosis, the cancer is a glioma.

In an embodiment of the foregoing, the glioma is selected from the group consisting of: high grade glioma, diffuse astrocytoma, oligodendroglioma, oligoastrocytoma, secondary glioblastoma, primary glioblastoma and diffuse intrinsic pontine glioma.

In an embodiment of the above-delineated method for establishing a molecular diagnosis, the cancer is a melanoma. In another embodiment of the method, the cancer is a glioma, high grade glioma, diffuse astrocytoma, oligodendroglioma, oligoastrocytoma, secondary glioblastoma, primary glioblastoma, diffuse intrinsic pontine glioma, a melanoma, or uveal melanoma.

In an embodiment of the method, the cancer is uveal melanoma.

In an embodiment of the above-delineated method for establishing a molecular diagnosis, the sample is from a skin biopsy or metastatic lesion.

In an embodiment of the above-delineated method, the control DNA template is derived from a melanoma cell or a melanoma cell line.

In an embodiment of the above-delineated method for establishing a molecular diagnosis, the first target nucleic acid comprises the nucleic acid sequence of a telomerase reverse transcriptase (TERT) gene promoter.

In an embodiment of the above-delineated method wherein the first target nucleic acid comprises the nucleic acid sequence of a telomerase reverse transcriptase (TERT) gene promoter, the mutant allele comprises variant C228T (hg19, chromosome 5:1,295,228) of the TERT gene promoter.

In an embodiment of the above-delineated method wherein the first target nucleic acid comprises the nucleic acid sequence of a telomerase reverse transcriptase (TERT) gene promoter, the mutant allele comprises variant C250T (hg19, chromosome 5:1,295,250) of the TERT gene promoter.

In an embodiment of the above-delineated method for establishing a molecular diagnosis, the control DNA template is derived from glioma cell line LN428.

In an embodiment of the above-delineated method for establishing a molecular diagnosis, the control DNA template is derived from glioma cell line LN443.

In another embodiment of the above-delineated method for establishing a molecular diagnosis, the first target nucleic acid comprises the nucleic acid sequence of an isocitrate dehydrogenase 1 (IDH1) gene.

In an embodiment of the above-delineated method wherein the first target nucleic acid comprises the nucleic acid sequence of an isocitrate dehydrogenase 1 (IDH1) gene, the mutant allele comprises a variant that encodes an IDH1 protein of variant R132H.

In an embodiment of the above-delineated method wherein the first target nucleic acid comprises the nucleic acid sequence of an isocitrate dehydrogenase 1 (IDH1) gene, the mutant allele comprises a variant that encodes an IDH1 protein of variant R132C.

In an embodiment of the above-delineated method wherein the first target nucleic acid comprises the nucleic acid sequence of an isocitrate dehydrogenase 1 (IDH1) gene, the mutant allele comprises a variant that encodes an IDH1 protein of variant R132G.

In an embodiment of the above-delineated method wherein the first target nucleic acid comprises the nucleic acid sequence of an isocitrate dehydrogenase 1 (IDH1) gene, the mutant allele comprises a variant that encodes an IDH1 protein of variant R132S.

In an embodiment of the above-delineated method wherein the first target nucleic acid comprises the nucleic acid sequence of an isocitrate dehydrogenase 1 (IDH1) gene, the mutant allele comprises a variant that encodes an IDH1 protein of variant R132L.

In another embodiment of the above-delineated method for establishing a molecular diagnosis, the first target nucleic acid comprises the nucleic acid sequence of a proto-oncogene B-raf (BRAF) gene.

In an embodiment of the above-delineated method wherein the first target nucleic acid comprises the nucleic acid sequence of a proto-oncogene B-raf (BRAF) gene, the mutant allele comprises a variant that encodes a BRAF protein of variant V600E.

In another embodiment of the above-delineated method for establishing a molecular diagnosis, the first target nucleic acid comprises the nucleic acid sequence of a neuroblastomas RAS viral oncogene homolog (NRAS) gene.

In an embodiment of the above-delineated method wherein the first target nucleic acid comprises the nucleic acid sequence of a neuroblastomas RAS viral oncogene homolog (NRAS), the mutant allele comprises a variant that encodes an NRAS protein of variant Q61R.

In an embodiment of the above-delineated method wherein the first target nucleic acid comprises the nucleic acid sequence of a neuroblastomas RAS viral oncogene homolog (NRAS), the mutant allele comprises a variant that encodes an NRAS protein of variant Q61K.

In another embodiment of the above-delineated method for establishing a molecular diagnosis, the first target nucleic acid comprises the nucleic acid sequence of a guanine nucleotide-binding protein G(q) subunit α (GNAQ) gene.

In an embodiment of the above-delineated method wherein the first target nucleic acid comprises the nucleic acid sequence of a guanine nucleotide-binding protein G(q) subunit α (GNAQ) gene, the mutant allele comprises a variant that encodes an GNAQ protein of variant R183Q.

In an embodiment of the above-delineated method wherein the first target nucleic acid comprises the nucleic acid sequence of a guanine nucleotide-binding protein G(q) subunit α (GNAQ) gene, the mutant allele comprises a variant that encodes an GNAQ protein of variant Q209L.

In an embodiment of the above-delineated method wherein the first target nucleic acid comprises the nucleic acid sequence of a guanine nucleotide-binding protein G(q) subunit α (GNAQ) gene, the mutant allele comprises a variant that encodes an GNAQ protein of variant Q209P.

In another embodiment of the above-delineated method for establishing a molecular diagnosis, the first target nucleic acid comprises the nucleic acid sequence of a guanine nucleotide-binding protein subunit α-11 (GNA11) gene.

In an embodiment of the above-delineated method wherein the first target nucleic acid comprises the nucleic acid sequence of a guanine nucleotide-binding protein subunit α-11 (GNA11) gene, the mutant allele comprises a variant that encodes an GNA11 protein of variant Q209L.

In another embodiment of the above-delineated method for establishing a molecular diagnosis, the first target nucleic acid comprises the nucleic acid sequence of a H3 histone, family 3A (H3F3A) gene.

In an embodiment of the above-delineated method wherein the first target nucleic acid comprises the nucleic acid sequence of a H3 histone, family 3A (H3F3A) gene, the mutant allele comprises a variant that encodes an H3F3A protein of variant K27M.

In an embodiment of the above-delineated method wherein the first target nucleic acid comprises the nucleic acid sequence of a H3 histone, family 3A (H3F3A) gene, the mutant allele comprises a variant that encodes an H3F3A protein of variant G34R.

In another embodiment of the above-delineated method for establishing a molecular diagnosis, the control DNA template is derived from primary glioma cell line BT142.

In an embodiment of the above-delineated method wherein the first target nucleic acid comprises the nucleic acid sequence of a telomerase reverse transcriptase (TERT) gene promoter, the forward primer comprises the nucleic acid sequence of 5'-CACGTGCGCAGCAGGACGCAG-3'.

In an embodiment of the above-delineated method wherein the first target nucleic acid comprises the nucleic acid sequence of a telomerase reverse transcriptase (TERT) gene promoter, the reverse primer comprises the nucleic acid sequence of 5'-CTTCACCTTCCAGCTCCGCCTC-3'.

In an embodiment of the above-delineated method wherein the first target nucleic acid comprises the nucleic acid sequence of a telomerase reverse transcriptase (TERT) gene promoter, the PNA blocker comprises the nucleic acid sequence of 5'-CCCAGCCCCTCCGGGCCC-3'.

In an embodiment of the above-delineated method wherein the first target nucleic acid comprises the nucleic acid sequence of a telomerase reverse transcriptase (TERT) gene promoter, the PNA blocker comprises the nucleic acid sequence of 5'-CCGACCCCTCCCGGGTCCC-3'.

In an embodiment of the above-delineated method wherein the first target nucleic acid comprises the nucleic acid sequence of a telomerase reverse transcriptase (TERT) gene promoter, the LNA probe comprises the nucleic acid sequence of 5'-CCCAGCCCC+T+TCCGGGCCC-3', wherein nucleotides preceded by a "+" are LNA modified nucleotides.

In an embodiment of the above-delineated method wherein the first target nucleic acid comprises the nucleic acid sequence of a telomerase reverse transcriptase (TERT) gene promoter, the LNA probe comprises the nucleic acid sequence of 5'-CCGACCCC+T+TCCGGGTCCC-3', wherein nucleotides preceded by a "+" are LNA modified nucleotides.

In an embodiment of the above-delineated method wherein the first target nucleic acid comprises the nucleic acid sequence of a telomerase reverse transcriptase (TERT) gene promoter, the LNA probe comprises the nucleic acid sequence of 5'-FAM-CCCAGCCCC+T+TCCGGGCCC-Dab-3', wherein nucleotides preceded by a "+" are LNA modified nucleotides, FAM is fluorescein moiety, and Dab is diaminobenzidine.

In an embodiment of the above-delineated method wherein the first target nucleic acid comprises the nucleic acid sequence of a telomerase reverse transcriptase (TERT) gene promoter, the LNA probe comprises the nucleic acid sequence of 5'-FAM-CCGACCCC+T+TCCGGGTCCC-Dab-3', wherein nucleotides preceded by a "+" are LNA modified nucleotides, FAM is fluorescein moiety, and Dab is diaminobenzidine.

In an embodiment of the above-delineated method wherein the first target nucleic acid comprises the nucleic acid sequence of an isocitrate dehydrogenase 1 (IDH1) gene, the forward primer comprises the nucleic acid sequence of 5'-CCGGCTTGTGAGTGGATGGGTAAAACCT-3'.

In an embodiment of the above-delineated method wherein the first target nucleic acid comprises the nucleic acid sequence of an isocitrate dehydrogenase 1 (IDH1) gene, the reverse primer comprises the nucleic acid sequence of 5'-CATTATTGCCAACATGACTTACTTGATCCCC-3'.

In an embodiment of the above-delineated method wherein the first target nucleic acid comprises the nucleic acid sequence of an isocitrate dehydrogenase 1 (IDH1) gene, the PNA blocker comprises the nucleic acid sequence of 5'-AGGTCGTCATGC-3'.

In an embodiment of the above-delineated method wherein the first target nucleic acid comprises the nucleic acid sequence of an isocitrate dehydrogenase 1 (IDH1) gene, the LNA probe comprises the nucleic acid sequence of 5'-AGG+T+C+A+T+CAT+GC-3', wherein nucleotides preceded by a "+" are LNA modified nucleotides.

In an embodiment of the above-delineated method wherein the first target nucleic acid comprises the nucleic acid sequence of an isocitrate dehydrogenase 1 (IDH1) gene, the LNA probe comprises the nucleic acid sequence of 5'-AGG+T+T+G+T+C+ATGC-3', wherein nucleotides preceded by a "+" are LNA modified nucleotides.

In an embodiment of the above-delineated method wherein the first target nucleic acid comprises the nucleic acid sequence of an isocitrate dehydrogenase 1 (IDH1) gene, the LNA probe comprises the nucleic acid sequence of 5'-AGGT+G+G+T+CAT+GC-3', wherein nucleotides preceded by a "+" are LNA modified nucleotides.

In an embodiment of the above-delineated method wherein the first target nucleic acid comprises the nucleic acid sequence of an isocitrate dehydrogenase 1 (IDH1) gene, the LNA probe comprises the nucleic acid sequence of 5'-AGGT+A+G+T+CA+T+GC-3' wherein nucleotides preceded by a "+" are LNA modified nucleotides.

In an embodiment of the above-delineated method wherein the first target nucleic acid comprises the nucleic acid sequence of an isocitrate dehydrogenase 1 (IDH1) gene, the LNA probe comprises the nucleic acid sequence of 5'-AGG+T+C+T+T+CAT+GC-3' wherein nucleotides preceded by a "+" are LNA modified nucleotides.

In an embodiment of the above-delineated method wherein the first target nucleic acid comprises the nucleic acid sequence of an isocitrate dehydrogenase 1 (IDH1) gene, the LNA probe comprises the nucleic acid sequence of 5'-FAM-AGG+T+C+A+T+CAT+GC-Dab-3', wherein nucleotides preceded by a "+" are LNA modified nucleotides, FAM is fluorescein moiety, and Dab is diaminobenzidine.

In an embodiment of the above-delineated method wherein the first target nucleic acid comprises the nucleic acid sequence of an isocitrate dehydrogenase 1 (IDH1) gene, the LNA probe comprises the nucleic acid sequence of 5'-MAXN-AGG+T+T+G+T+C+ATGC-Dab-3', wherein nucleotides preceded by a "+" are LNA modified nucleotides, MAXN is fluorescent moiety, and Dab is diaminobenzidine.

In an embodiment of the above-delineated method wherein the first target nucleic acid comprises the nucleic acid sequence of an isocitrate dehydrogenase 1 (IDH1) gene, the LNA probe comprises the nucleic acid sequence of 5'-MAXN-AGGT+G+G+T+CAT+GC-Dab-3', wherein nucleotides preceded by a "+" are LNA modified nucleotides, MAXN is fluorescent moiety, and Dab is diaminobenzidine.

In an embodiment of the above-delineated method wherein the first target nucleic acid comprises the nucleic acid sequence of an isocitrate dehydrogenase 1 (IDH1) gene, the LNA probe comprises the nucleic acid sequence of 5'-MAXN-AGGT+A+G+T+CA-T+GC-Dab-3 ', wherein nucleotides preceded by a "+" are LNA modified nucleotides, MAXN is fluorescent moiety, and Dab is diaminobenzidine.

In an embodiment of the above-delineated method wherein the first target nucleic acid comprises the nucleic acid sequence of an isocitrate dehydrogenase 1 (IDH1) gene, the LNA probe comprises the nucleic acid sequence of 5'-MAXN-AGG+T+C+T+T+CAT+GC-Dab-3' wherein nucleotides preceded by a "+" are LNA modified nucleotides, MAXN is fluorescent moiety, and Dab is diaminobenzidine.

In an embodiment of the above-delineated method wherein the first target nucleic acid comprises the nucleic acid sequence of a proto-oncogene B-raf (BRAF) gene, the forward primer comprises the nucleic acid sequence of 5'-ACAGGGCATGGAGAGTGGGTC-3'.

In an embodiment of the above-delineated method wherein the first target nucleic acid comprises the nucleic acid sequence of a proto-oncogene B-raf (BRAF) gene, the reverse primer comprises the nucleic acid sequence of 5'-CAAACTGATGGGACCCACTCCAT-3'.

In an embodiment of the above-delineated method wherein the first target nucleic acid comprises the nucleic acid sequence of a proto-oncogene B-raf (BRAF) gene, the PNA blocker comprises the nucleic acid sequence of 5'-CATCGAGATTTCACTGTAGCTAGA-3'.

In an embodiment of the above-delineated method wherein the first target nucleic acid comprises the nucleic acid sequence of a proto-oncogene B-raf (BRAF) gene, the LNA probe comprises the nucleic acid sequence of 5'-AGA+TT+T+C+T+CT+GT+AG+C-3', wherein nucleotides preceded by a "+" are LNA modified nucleotides.

In an embodiment of the above-delineated method wherein the first target nucleic acid comprises the nucleic acid sequence of a proto-oncogene B-raf (BRAF) gene, the LNA probe comprises the nucleic acid sequence of 5'-FAM-AGA+TT+T+C+T+CT+GT+AG+C-Dab-3', wherein nucleotides preceded by a "+" are LNA modified nucleotides, FAM is fluorescein moiety, and Dab is diaminobenzidine.

In an embodiment of the above-delineated method wherein the first target nucleic acid comprises the nucleic acid sequence of a proto-oncogene B-raf (BRAF) gene, the LNA probe comprises the nucleic acid sequence of 5'-MAXN-AGA+TT+T+C+T+CT+GT+AG+C-Dab-3', wherein nucleotides preceded by a "+" are LNA modified nucleotides, MAXN is fluorescent moiety, and Dab is diaminobenzidine.

In an embodiment of the above-delineated method wherein the first target nucleic acid comprises the nucleic acid sequence of a neuroblastomas RAS viral oncogene homolog (NRAS), the forward primer comprises the nucleic acid sequence of 5'-AGTGGTTATAGATGGTGAAAC-CTG-3'.

In an embodiment of the above-delineated method wherein the first target nucleic acid comprises the nucleic acid sequence of a neuroblastomas RAS viral oncogene homolog (NRAS), the reverse primer comprises the nucleic acid sequence of 5'-ACAGAGGAAGCCTTCGCCTG-3'.

In an embodiment of the above-delineated method wherein the first target nucleic acid comprises the nucleic acid sequence of a neuroblastomas RAS viral oncogene homolog (NRAS), the PNA blocker comprises the nucleic acid sequence of 5'-CAGCTGGACAAGAAGAGTAC-KK-3'.

In an embodiment of the above-delineated method wherein the first target nucleic acid comprises the nucleic acid sequence of a neuroblastomas RAS viral oncogene homolog (NRAS), the LNA probe comprises the nucleic acid sequence of 5'-CTGG+AC+G+AG+AA+GAGTA-3', wherein nucleotides preceded by a "+" are LNA modified nucleotides.

In an embodiment of the above-delineated method wherein the first target nucleic acid comprises the nucleic acid sequence of a neuroblastomas RAS viral oncogene homolog (NRAS), the LNA probe comprises the nucleic acid sequence of 5'-CAG+CTGGA+A+A+AGAA+GA+GTA-3', wherein nucleotides preceded by a "+" are LNA modified nucleotides.

In an embodiment of the above-delineated method wherein the first target nucleic acid comprises the nucleic acid sequence of a neuroblastomas RAS viral oncogene homolog (NRAS), the LNA probe comprises the nucleic acid sequence of 5'-FAM-CTGG+AC+G+AG+AA+GAGTA-Dab-3', wherein nucleotides preceded by a "+" are LNA modified nucleotides, FAM is fluorescein moiety, and Dab is diaminobenzidine.

In an embodiment of the above-delineated method wherein the first target nucleic acid comprises the nucleic acid sequence of a neuroblastomas RAS viral oncogene homolog (NRAS), the LNA probe comprises the nucleic acid sequence of 5'-FAM-CAG+CTGGA+A+A+AGAA+GA+GTA-Dab-3', wherein nucleotides preceded by a "+" are LNA modified nucleotides, FAM is fluorescein moiety, and Dab is diaminobenzidine.

In an embodiment of the above-delineated method wherein the first target nucleic acid comprises the nucleic acid sequence of a neuroblastomas RAS viral oncogene homolog (NRAS), the LNA probe comprises the nucleic acid sequence of 5'-MAXN-CTGG+AC+G+AG+AA+GAGTA-Dab-3', wherein nucleotides preceded by a "+" are LNA modified nucleotides, MAXN is fluorescent moiety, and Dab is diaminobenzidine.

In an embodiment of the above-delineated method wherein the first target nucleic acid comprises the nucleic acid sequence of a neuroblastomas RAS viral oncogene homolog (NRAS), the LNA probe comprises the nucleic acid sequence of 5'-MAXN-CAG+CTGGA+A+A+AGAA+GA+GTA-Dab-3', wherein nucleotides preceded by a "+" are LNA modified nucleotides, MAXN is fluorescent moiety, and Dab is diaminobenzidine.

In an embodiment of the above-delineated method wherein the first target nucleic acid comprises the nucleic acid sequence of a guanine nucleotide-binding protein G(q) subunit α (GNAQ) gene, the forward primer comprises the nucleic acid sequence of 5'-TTGGACCGCGTAGCTGAC-CCT-3'.

In an embodiment of the above-delineated method wherein the first target nucleic acid comprises the nucleic acid sequence of a guanine nucleotide-binding protein G(q) subunit α (GNAQ) gene, the reverse primer comprises the nucleic acid sequence of 5'-GCTGGGAAATAG-GTTTCATGGAC-3'.

In an embodiment of the above-delineated method wherein the first target nucleic acid comprises the nucleic acid sequence of a guanine nucleotide-binding protein G(q) subunit α (GNAQ) gene, the PNA blocker comprises the nucleic acid sequence of 5'-TTAGAGTTCGAGTCCCCA-3'.

In an embodiment of the above-delineated method wherein the first target nucleic acid comprises the nucleic acid sequence of a guanine nucleotide-binding protein G(q) subunit α (GNAQ) gene, the LNA probe comprises the nucleic acid sequence of 5'-AGAGT+TC+A+AGT+CCCCAC-3', wherein nucleotides preceded by a "+" are LNA modified nucleotides.

In an embodiment of the above-delineated method wherein the first target nucleic acid comprises the nucleic acid sequence of a guanine nucleotide-binding protein G(q) subunit α (GNAQ) gene, the LNA probe comprises the nucleic acid sequence of 5'-FAM-AGAGT+TC+A+AGT+CCCCAC-Dab-3', wherein nucleotides preceded by a "+" are LNA modified nucleotides, FAM is fluorescein moiety, and Dab is diaminobenzidine.

In an embodiment of the above-delineated method wherein the first target nucleic acid comprises the nucleic acid sequence of a guanine nucleotide-binding protein G(q) subunit α (GNAQ) gene, the LNA probe comprises the nucleic acid sequence of 5'-MAXN-AGAGT+TC+A+AGT+CCCCAC-Dab-3', wherein nucleotides preceded by a "+" are LNA modified nucleotides, MAXN is fluorescent moiety, and Dab is diaminobenzidine.

In an embodiment of the above-delineated method wherein the first target nucleic acid comprises the nucleic acid sequence of a guanine nucleotide-binding protein G(q) subunit α (GNAQ) gene, the forward primer comprises the nucleic acid sequence of 5'-CCCTAAGTTTGTAAGTAGT-GCTATA-3'.

In an embodiment of the above-delineated method wherein the first target nucleic acid comprises the nucleic acid sequence of a guanine nucleotide-binding protein G(q) subunit α (GNAQ) gene, the reverse primer comprises the nucleic acid sequence of 5'-TCACTAAGCGCTACTA-GAAACATG-3'.

In an embodiment of the above-delineated method wherein the first target nucleic acid comprises the nucleic acid sequence of a guanine nucleotide-binding protein G(q) subunit α (GNAQ) gene, the PNA blocker comprises the nucleic acid sequence of 5'-GGGGCCAAAGGTCAGAGA-3'.

In an embodiment of the above-delineated method wherein the first target nucleic acid comprises the nucleic acid sequence of a guanine nucleotide-binding protein G(q) subunit α (GNAQ) gene, the LNA probe comprises the nucleic acid sequence of 5'-AGGGGCC+T+AAGGTCA-GAG-3', wherein nucleotides preceded by a "+" are LNA modified nucleotides.

In an embodiment of the above-delineated method wherein the first target nucleic acid comprises the nucleic acid sequence of a guanine nucleotide-binding protein G(q) subunit α (GNAQ) gene, the LNA probe comprises the nucleic acid sequence of 5'-GGGCC+C+AAGGTCA-GAGA-3', wherein nucleotides preceded by a "+" are LNA modified nucleotides.

In an embodiment of the above-delineated method wherein the first target nucleic acid comprises the nucleic acid sequence of a guanine nucleotide-binding protein G(q) subunit α (GNAQ) gene, the LNA probe comprises the nucleic acid sequence of 5'-FAM-AGGGGCC+T+AAGGTCAGAG-Dab-3', wherein nucleotides preceded by a "+" are LNA modified nucleotides, FAM is fluorescein moiety, and Dab is diaminobenzidine.

In an embodiment of the above-delineated method wherein the first target nucleic acid comprises the nucleic acid sequence of a guanine nucleotide-binding protein G(q) subunit α (GNAQ) gene, the LNA probe comprises the nucleic acid sequence of 5'-FAM-GGGCC+C+AAGGTCA-GAGA-Dab-3', wherein nucleotides preceded by a "+" are LNA modified nucleotides, FAM is fluorescein moiety, and Dab is diaminobenzidine.

In an embodiment of the above-delineated method wherein the first target nucleic acid comprises the nucleic acid sequence of a guanine nucleotide-binding protein G(q) subunit α (GNAQ) gene, the LNA probe comprises the nucleic acid sequence of 5'-MAXN-AGGGGCC+T+AAGGTCAGAG-Dab-3', wherein nucleotides preceded by a "+" are LNA modified nucleotides, MAXN is fluorescent moiety, and Dab is diaminobenzidine.

In an embodiment of the above-delineated method wherein the first target nucleic acid comprises the nucleic acid sequence of a guanine nucleotide-binding protein G(q) subunit α (GNAQ) gene, the LNA probe comprises the nucleic acid sequence of 5'-MAXN-GGGCC+C+AAGGTCAGAGA-Dab-3', wherein nucleotides preceded by a "+" are LNA modified nucleotides, MAXN is fluorescent moiety, and Dab is diaminobenzidine.

In an embodiment of the above-delineated method wherein the first target nucleic acid comprises the nucleic acid sequence of a guanine nucleotide-binding protein subunit α-11 (GNA11) gene, the forward primer comprises the nucleic acid sequence of 5'-GCAGATTGGGCCT-TGGGGCG-3'.

In an embodiment of the above-delineated method wherein the first target nucleic acid comprises the nucleic acid sequence of a guanine nucleotide-binding protein subunit α-11 (GNA11) gene, the reverse primer comprises the nucleic acid sequence of 5'-TCGCTGAGGGCGACGA-GAAAC-3'.

In an embodiment of the above-delineated method wherein the first target nucleic acid comprises the nucleic acid sequence of a guanine nucleotide-binding protein subunit α-11 (GNA11) gene, the PNA blocker comprises the nucleic acid sequence of 5'-GGGCCAGCGGTCGGAGC-3'.

In an embodiment of the above-delineated method wherein the first target nucleic acid comprises the nucleic acid sequence of a guanine nucleotide-binding protein subunit α-11 (GNA11) gene, the LNA probe comprises the nucleic acid sequence of 5'-GGG+CC+T+GCGGTCGG-3', wherein nucleotides preceded by a "+" are LNA modified nucleotides.

In an embodiment of the above-delineated method wherein the first target nucleic acid comprises the nucleic acid sequence of a guanine nucleotide-binding protein subunit α-11 (GNA11) gene, the LNA probe comprises the nucleic acid sequence of 5'-FAM-GGG+CC+T+GCG-GTCGG-Dab-3', wherein nucleotides preceded by a "+" are LNA modified nucleotides, FAM is fluorescein moiety, and Dab is diaminobenzidine.

In an embodiment of the above-delineated method wherein the first target nucleic acid comprises the nucleic acid sequence of a guanine nucleotide-binding protein subunit α-11 (GNA11) gene, the LNA probe comprises the nucleic acid sequence of 5'-MAXN-GGG+CC+T+GCG-GTCGG-Dab-3', wherein nucleotides preceded by a "+" are LNA modified nucleotides, MAXN is fluorescent moiety, and Dab is diaminobenzidine.

In an embodiment of the above-delineated method wherein the first target nucleic acid comprises the nucleic acid sequence of a H3 histone, family 3A (H3F3A) gene, the forward primer comprises the nucleic acid sequence of 5'-CTGCCCGCAAATCGACCGGT-3'.

In an embodiment of the above-delineated method wherein the first target nucleic acid comprises the nucleic acid sequence of a H3 histone, family 3A (H3F3A) gene, the reverse primer comprises the nucleic acid sequence of 5'-GGATACATACAAGAGAGACTTTGTC-3'.

In an embodiment of the above-delineated method wherein the first target nucleic acid comprises the nucleic acid sequence of a H3 histone, family 3A (H3F3A) gene, the PNA blocker comprises the nucleic acid sequence of 5'-GC-CGCTCGCAAGAGTGCGCC-3'.

In an embodiment of the above-delineated method wherein the first target nucleic acid comprises the nucleic acid sequence of a H3 histone, family 3A (H3F3A) gene, the LNA probe comprises the nucleic acid sequence of 5'-CGCTCGC+A+T+GAGTG-3', wherein nucleotides preceded by a "+" are LNA modified nucleotides.

In an embodiment of the above-delineated method wherein the first target nucleic acid comprises the nucleic acid sequence of a H3 histone, family 3A (H3F3A) gene, the LNA probe comprises the nucleic acid sequence of 5'-FAM-CGCTCGC+A+T+GAGTG-Dab-3', wherein nucleotides preceded by a "+" are LNA modified nucleotides, FAM is fluorescein moiety, and Dab is diaminobenzidine.

In an embodiment of the above-delineated method wherein the first target nucleic acid comprises the nucleic acid sequence of a H3 histone, family 3A (H3F3A) gene, the LNA probe comprises the nucleic acid sequence of 5'-MAXN-CGCTCGC+A+T+GAGTG-Dab-3', wherein nucleotides preceded by a "+" are LNA modified nucleotides, MAXN is fluorescent moiety, and Dab is diaminobenzidine.

In an embodiment of the above-delineated method wherein the first target nucleic acid comprises the nucleic acid sequence of a H3 histone, family 3A (H3F3A) gene, the PNA blocker comprises the nucleic acid sequence of TTCT-TCACCCCTCCAGTAG In an embodiment of the above-delineated method wherein the first target nucleic acid comprises the nucleic acid sequence of a H3 histone, family 3A (H3F3A) gene, the LNA probe comprises the nucleic acid sequence of TACT+GGA+A+GG+GTGAAGA, wherein nucleotides preceded by a "+" are LNA modified nucleotides.

In an embodiment of the above-delineated method wherein the first target nucleic acid comprises the nucleic acid sequence of a H3 histone, family 3A (H3F3A) gene, the LNA probe comprises the nucleic acid sequence of 5'-FAM-TACT+GGA+A+GG+GTGAAGA-Dab-3', wherein nucleotides preceded by a "+" are LNA modified nucleotides, FAM is fluorescein moiety, and Dab is diaminobenzidine.

In an embodiment of the above-delineated method wherein the first target nucleic acid comprises the nucleic acid sequence of a H3 histone, family 3A (H3F3A) gene, the LNA probe comprises the nucleic acid sequence of 5'-MAXN-TACT+GGA+A+GG+GTGAAGA-Dab-3', wherein nucleotides preceded by a "+" are LNA modified nucleotides, FAM is fluorescein moiety, and Dab is diaminobenzidine.

One aspect provides a method of any one or more of the above-delineated methods and embodiments, wherein two or more mutant alleles of TERT, IDH BRAF, NRAS, GNAQ, GNA11 and/or H3F3A are detected simultaneously.

In another embodiment of the above-delineated method for establishing a molecular diagnosis, the method further comprises calculating tumor burden or tumor purity in the sample, based on quantitative amount of mutant allele detected.

In an embodiment of the foregoing method, the calculating of tumor burden or tumor purity of the sample is based on the quantitative amount of mutant allele detected relative to a standard curve generated from serial dilutions of control DNA.

In another embodiment of the above-delineated method for establishing a molecular diagnosis, sample from the subject is taken from a concurrent surgical procedure involving the subject and a surgeon, wherein the sample from the subject is obtained in rapid fashion, and wherein results of the method are available to the surgeon to guide further treatment of the subject during the surgical procedure.

In another embodiment of the above-delineated method for establishing a molecular diagnosis, the method further comprises subsequent resection of a glioma tumor in the subject.

In another embodiment of the above-delineated method for establishing a molecular diagnosis, the method further comprises inserting a therapeutic drug-coated wafer into a central cavity of a tumor in the subject.

In another embodiment of the above-delineated method for establishing a molecular diagnosis, the denaturing is initially done in about 1 round of incubation at about 95° C. for 2-5 minutes, and the annealing and amplifying are done in about 45 rounds of incubation at 95° C. for 1-12 seconds followed by about 62.5° C. to 64.5° C. for about 10-25 seconds.

In another embodiment of the above-delineated method for establishing a molecular diagnosis, the annealing and amplifying are done in about 40-50 rounds of incubation at 95° C. for 1-12 seconds followed by about 62.5° C. to about 64.5° C. for about 10-25 seconds.

In another embodiment of the above-delineated method for establishing a molecular diagnosis, the annealing and amplifying are done in about 35-45 rounds of incubation at 95° C. for 1-12 seconds followed by about 62.5° C. to about 64.5° C. for about 10-25 seconds.

In another embodiment of the above-delineated method for establishing a molecular diagnosis, the annealing and amplifying are done in about 40-45 rounds of incubation at 95° C. for 1-12 seconds followed by about 62.5° C. to about 64.5° C. for about 10-25 seconds.

In another embodiment of the above-delineated method for establishing a molecular diagnosis, the melting temperatures of the forward primer, reverse primer, LNA probe and PNA blocker are about 62.5° C. to about 64.5° C.

In another embodiment of the above-delineated method for establishing a molecular diagnosis, the melting temperatures of the forward primer, reverse primer, LNA probe and PNA blocker are about 63.5° C.

In another embodiment of the above-delineated method for establishing a molecular diagnosis, the amplicon is less than 70-300 nt in length.

In another embodiment of the above-delineated method for establishing a molecular diagnosis, the denaturing, annealing and amplifying steps are performed in a thermocycler with a ramping rate of at least 1.6-3.1° C. per second.

In another embodiment of any of the above-delineated methods and embodiments thereof, the mutant allele has an allelic frequency of 0.1% of the nucleic acid extracted from the sample.

In another embodiment of any of the above-delineated methods and embodiments thereof, the sample comprises archival tissue.

In an embodiment of the foregoing, the archival tissue is formalin-fixed paraffin embedded.

In another embodiment of any of the above-delineated methods and embodiments thereof, the method further comprises validation of genome editing in cell culture or in an animal model.

The present invention is not to be limited in scope by the specific embodiments described herein. Indeed, various modifications in addition to those described herein will become apparent to those skilled in the art from the foregoing description and the accompanying figures. Such modifications are intended to fall within the scope of the appended claims.

---

What is claimed is:

1. A method for establishing a molecular diagnosis in at least one cancer in a subject, the method comprising:
   (a) isolating DNA from a sample from the subject;
   (b) denaturing the DNA isolated from the sample and a control DNA template;
   (c) annealing a forward primer that hybridizes to a first region on a sense strand of a first target nucleic acid, a reverse primer that hybridizes to a second region on an antisense strand of the first target nucleic acid, a locked nucleic acid (LNA) probe comprising an oligonucleotide with at least one LNA modification on at least one nucleotide, wherein the probe comprises a nucleic acid sequence that is complementary to a mutant allele of the first target nucleic acid, and a peptide nucleic acid (PNA) blocker that hybridizes to a wild-type allele of the first target nucleic acid;
   (d) amplifying a DNA amplicon comprising the mutant allele in the first target nucleic acid;
   (e) detecting the mutant allele in the first target nucleic acid in the sample; and
   (f) quantifying the amount of the mutant allele in the first target nucleic acid in the sample relative to the amount in a control, wherein a higher prevalence of the amount of mutant allele in the sample relative to the control indicates presence and/or stage of the cancer in the subject.

2. The method of claim 1, wherein the sample comprises a tissue biopsy, blood, plasma, serum, cerebrospinal fluid, or one or more circulating cancer cells from the subject.

3. The method of claim 1, wherein the sample comprises tissue from the subject, or one or more cancer cells from the subject.

4. The method of claim 1, wherein the cancer is a glioma, high grade glioma, diffuse astrocytoma, oligodendroglioma, oligoastrocytoma, secondary glioblastoma, primary glioblastoma, diffuse intrinsic pontine glioma, a melanoma, or uveal melanoma.

5. The method of claim 1, wherein the sample is from a skin biopsy or metastatic lesion.

6. The method of claim 1, wherein the first target nucleic acid comprises the nucleic sequence of a telomerase reverse transcriptase (TERT) gene promoter.

7. The method of claim 1, wherein the first target nucleic acid comprises the nucleic acid sequence of an isocitrate dehydrogenase 1 (IDH1) gene.

8. The method of claim 1, wherein the first target nucleic acid comprises the nucleic acid sequence of a proto-oncogene B-raf (BRAF) gene.

9. The method of claim 1, wherein the first target nucleic acid comprises the nucleic acid sequence of a neuroblastomas RAS viral oncogene homolog (NRAS) gene.

10. The method of claim 1, wherein the first target nucleic acid comprises the nucleic acid sequence of a guanine nucleotide-binding protein G(q) subunit α (GNAQ) gene.

11. The method of claim 1, wherein the first target nucleic acid comprises the nucleic acid sequence of a guanine nucleotide-binding protein subunit α-11 (GNA11) gene.

12. The method of claim 1, wherein the first target nucleic acid comprises the nucleic acid sequence of a H3 histone, family 3A (H3F3A) gene.

13. The method of claim 1, wherein sample from the subject is taken from a concurrent surgical procedure involving the subject and a surgeon, wherein the sample from the subject is obtained in rapid fashion, and wherein results of the method are available to the surgeon to guide further treatment of the subject during the surgical procedure.

14. The method of claim 1, further comprising subsequent resection of a glioma tumor in the subject.

15. The method of claim 1, further comprising inserting a therapeutic drug-coated wafer into a central cavity of a tumor in the subject.

16. A system for detection or amplification of a single nucleotide polymorphism (SNP) or somatic nucleotide alteration in a target nucleic acid in a sample, the system comprising:
(a) a sample comprising a target nucleic acid;
(b) a forward primer that hybridizes to a first region on a sense strand of the target nucleic acid sequence in the sample, wherein the target nucleic acid comprises a single nucleotide polymorphism (SNP) or somatic nucleotide alteration compared to a corresponding wild-type nucleic acid which does not comprise the SNP or somatic nucleotide alteration;
(c) a reverse primer that hybridizes to a second region on an antisense strand of the target nucleic acid;
(d) a locked nucleic acid (LNA) probe comprising an oligonucleotide with at least one LNA modification on at least one nucleotide, wherein the LNA probe comprises a nucleic acid sequence that is complementary to the target nucleic acid comprising the SNP or somatic nucleotide alteration and is located within the nucleic acid region amplified by the forward primer and the reverse primer;
(e) a peptide nucleic acid (PNA) blocker that hybridizes to a wild-type allele of the target nucleic acid, the blocker comprising peptide nucleic acid oligonucleotides that block amplification of the wild-type allele, and do not block amplification of the target nucleic acid comprising the SNP or somatic nucleotide alteration, wherein the PNA blocker hybridizes to a nucleic acid sequence located within the region amplified by the forward primer and the reverse primer; and
(f) a reaction buffer;
wherein the forward primer, the reverse primer, the LNA probe, and the PNA blocker recognize their target nucleic acids under same temperature conditions.

17. The system of claim 16, wherein the mutant allele comprises a single nucleotide polymorphism or somatic variant.

18. The system of claim 16, wherein the sample comprises tissue from a model organism, a cell from a tissue biopsy obtained from a subject, a cancer cell, nucleated cell obtained from blood obtained from a subject, or a circulating cancer cell.

19. A kit comprising the system of claim 16.

20. The system of claim 16 wherein the SNP or somatic nucleotide alteration in a target nucleic acid in the sample is detected or amplified by a method comprising:
(a) isolating DNA from the sample;
(b) denaturing the isolated DNA;
(c) annealing the forward primer, the reverse primer, the LNA probe, and the PNA blocker to the DNA at the same temperature conditions; and
(d) amplifying and detecting a DNA amplicon comprising the one or more single nucleotide polymorphisms, thereby detecting or amplifying one or more single nucleotide polymorphisms.

21. The system of claim 16, wherein the target nucleic acid comprises a single nucleotide polymorphism (SNP) or somatic nucleotide alteration in the nucleic acid sequence of a telomerase reverse transcriptase (TERT) gene promoter; the nucleic acid sequence of an isocitrate dehydrogenase 1 (IDH1) gene; the nucleic acid sequence of a proto-oncogene B-raf (BRAF) gene; the nucleic acid sequence of a neuroblastomas RAS viral oncogene homolog (NRAS) gene; the nucleic acid sequence of a guanine nucleotide-binding protein G(q) subunit α (GNAQ) gene; the nucleic acid sequence of a guanine nucleotide-binding protein subunit α-11 (GNA11) gene; or the nucleic acid sequence of a H3 histone, family 3A (H3F3A) gene compared with a corresponding nucleic acid sequence which does not comprise the single nucleotide polymorphism (SNP) or somatic nucleotide alteration.

22. The system of claim 16, wherein the target nucleic acid comprises the single nucleotide polymorphism (SNP) or somatic nucleotide alteration in a coding and/or regulatory region of a gene or allele.

23. The system of claim 16, wherein the target nucleic acid comprises a GC content of 60% or greater.

* * * * *